United States Patent
Kumar et al.

(10) Patent No.: US 11,883,469 B2
(45) Date of Patent: Jan. 30, 2024

(54) METHOD OF TREATING SPINAL CORD INJURY

(71) Applicant: UNIVERSITY OF THE WITWATERSRAND, JOHANNESBURG, Johannesburg (ZA)

(72) Inventors: Pradeep Kumar, Johannesburg (ZA); Viness Pillay, Johannesburg (ZA); Yahya Essop Choonara, Johannesburg (ZA); Girish Modi, Johannesburg (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 562 days.

(21) Appl. No.: 16/956,935

(22) PCT Filed: Dec. 19, 2018

(86) PCT No.: PCT/IB2018/060345
§ 371 (c)(1),
(2) Date: Jun. 22, 2020

(87) PCT Pub. No.: WO2019/123317
PCT Pub. Date: Jun. 27, 2019

(65) Prior Publication Data
US 2020/0405821 A1 Dec. 31, 2020

(30) Foreign Application Priority Data
Dec. 21, 2017 (ZA) .............................. ZA2017/08733

(51) Int. Cl.
| | | |
|---|---|---|
| A61K 38/39 | (2006.01) | |
| A61K 47/58 | (2017.01) | |
| A61K 47/64 | (2017.01) | |
| A61P 25/00 | (2006.01) | |
| A61K 9/00 | (2006.01) | |
| A61K 9/70 | (2006.01) | |
| A61K 47/18 | (2017.01) | |
| A61L 27/18 | (2006.01) | |
| A61L 27/22 | (2006.01) | |
| A61L 27/24 | (2006.01) | |
| A61L 27/56 | (2006.01) | |

(52) U.S. Cl.
CPC ............ *A61K 38/39* (2013.01); *A61K 9/0024* (2013.01); *A61K 9/70* (2013.01); *A61K 47/183* (2013.01); *A61K 47/58* (2017.08); *A61K 47/6435* (2017.08); *A61L 27/18* (2013.01); *A61L 27/227* (2013.01); *A61L 27/24* (2013.01); *A61L 27/56* (2013.01); *A61P 25/00* (2018.01); *A61L 2430/32* (2013.01)

(58) Field of Classification Search
CPC ....... A61K 9/0024; A61K 38/39; A61P 25/00; C08L 33/20
See application file for complete search history.

(56) References Cited

U.S. PATENT DOCUMENTS

| | | | |
|---|---|---|---|
| 2006/0210594 A1* | 9/2006 | Trieu ...................... | A61F 2/442 264/109 |
| 2010/0093093 A1* | 4/2010 | Leong ..................... | A61L 27/60 521/149 |
| 2010/0222881 A1* | 9/2010 | Prewett ................... | A61L 31/10 623/11.11 |
| 2012/0045651 A1* | 2/2012 | Myung ................ | C08G 18/831 525/127 |

FOREIGN PATENT DOCUMENTS

WO   2016/040961 A1   3/2016

OTHER PUBLICATIONS

Yudin et al (Fibre Chemistry, 1973, vol. 5, pp. 348-349) (Year: 1973).*
Buttafoco et al (Biomaterials, 2006, vol. 27, pp. 724-734) (Year: 2006).*
Miranda-Nieves et al (ACS Biomater. Sci. Eng., Published Jul. 2016, vol. 3, pp. 694-711) (Year: 2016).*
ISR for International Application PCT/IB2018/060345.
Written Opinion ISR for International Application PCT/IB2018/060345.
Ji Enchen et al.; "Tissue engineering is a promising method for the repair of spinal cord injuries (Review)", Experimental and Therapeutic Medicine, vol. 7, No. 3, Dec. 18, 2013 (Dec. 18, 2013), p. 523-528.
Jain Ra, et al; "Macroporous interpenetrating cryogel network of poly(acrylonitrile) and gelatin for biomedical applications", Journal of Materials Science: Materials in Medicine, Kluwer Academic Publishers, Bo,vol. 20, No. 1, Jul. 3, 2008 (Jul. 3, 2008), p. 173-179.
Suri Shalu, etal.; "Cell-Laden Hydrogel Constructs of Hyaluronic Acid, Collagen, and Laminin for Neural Tissue Engineering", Tissue Engineering Part A,vol. 16, No. 5, May 1, 2010 (May 1, 2010), p. 1703-1716.

* cited by examiner

*Primary Examiner* — Mark V Stevens
(74) *Attorney, Agent, or Firm* — LADAS & PARRY LLP

(57) ABSTRACT

A polyacrylonitrile (PANi) based pharmaceutical composition providing a porous implant for use in treating spinal cord trauma and/or spinal cord injury. Particularly a pharmaceutical composition including polyacrylonitrile (PANi) and/or elastin (E) and/or collagen (C) to form a PANi-E and/or PANi-C and/or a PANi-EC polymer network. Particularly, a pharmaceutical composition including polyacrylonitrile (PANi), elastin (E), and collagen (C) together forming a polyacrylonitrile (PANi), elastin (E), collagen (C) polymer network (PANi-E-C), wherein the polyacrylonitrile (PANi) may be crosslinked to form a crosslinked interpenetrating polyacrylonitrile (PANi), elastin (E) and collagen (C) polymer network (xpi-PANi-E-C), and wherein secondary protein structures of elastin (E) and collagen (C) reorientate. The disclosure extends to use of the pharmaceutical composition in the treatment of spinal cord trauma and/or spinal cord injury.

4 Claims, 36 Drawing Sheets

FIGURE 1 A and B

FIGURE 7 A and B

FIGURE 15 A AND B

FIGURE 17 A AND B

METHOD OF TREATING SPINAL CORD INJURY

RELATED APPLICATION

This application is an application under 35 U.S.C. 371 of International Application No. PCT/IB2018/060345 filed on 19 Dec. 2018, which claims priority from ZA Application No. 2017/08733 filed on 21 Dec. 2017, the disclosures of which are incorporated in their entirety by reference herein.

FIELD

This disclosure relates to a pharmaceutical composition, typically the pharmaceutical composition for use in the treatment of spinal cord trauma and/or spinal cord injury in a human or animal body, and a method of producing same. Particularly, this disclosure relates to a polyacrylonitrile (PANi) based pharmaceutical composition providing a porous implant for use in the treatment of spinal cord trauma and/or spinal cord injury. Further particularly, this disclosure relates to a pharmaceutical composition comprising polyacrylonitrile (PANi), elastin (E), and collagen (C) together forming a polyacrylonitrile (PANi), elastin (E), collagen (C) polymer network (PANi-E-C), wherein the polyacrylonitrile (PANi) may be crosslinked to form a crosslinked interpenetrating polyacrylonitrile (PANi), elastin (E) and collagen (C) polymer network (xpi-PANi-E-C), and wherein secondary protein structures of elastin (E) and collagen (C) reorientate. The invention extends to use of the pharmaceutical composition in the treatment of spinal cord trauma and/or spinal cord injury, and further extends to methods of treating spinal cord trauma and/or spinal cord injury.

BACKGROUND

Spinal cord injury (SCI) and particularly traumatic spinal cord injury (TSCI) are often devastating to a human or animal, resulting in paralysis or partial-paralysis. SCI and TSCI provide for numerous and complicated interventional challenges including, for example, extensive inflammation, axonal tethering, scar formation, neuronal degeneration and functional loss that need to be addressed before even a marginal neuronal recovery may be achieved.

It is said that there are between 223 and 755 persons per million in a human population that suffer from the after effects of SCI and/or TSCI, and that there are about between 10.4 and 83 persons per million in the population that suffer a SCI and/or TSCI per year. It is further notable that the average person living with a SCI/TSCI will live almost as long as a person without. As such, there is a desperate need to improve treatment and/or repair and/or recovery outcomes for persons having suffered a SCI/TSCI.

Injury to the spinal cord triggers, and involves, several bio-molecular and biochemical events including, for example, migration of macrophages, microglial processes, precursors of oligodendrocytic cells, and astrocytes into the site of injury. The penetration of such molecules into a site of spinal cord lesion in turn produces biomolecules such as myelin-associated glycoprotein and chondroitin sulphate proteoglycans. These are inhibitory molecules that facilitate the formation of scar tissue at the lesion site, and typically include astroglial structures. The scar tissue marks the failure of regrowth in the ensuing lesioned axons.

Currently, available neurotherapeutic strategies are not sufficient, even when applied a few hours after SCI/TSCI. For effective regeneration of the neuronal tissue, the damaged axons must surpass cystic cavities to repair the chronically damaged cord for the restoration of neurological function requiring reuniting the injury gap. Repair of the SCI necessitates bridging of the injury gap. There has been research directed toward employing biomaterials to act as nerve conduits to allow directed axonal growth, however, there has been little success in providing an effective repair means.

A pharmaceutical composition and/or an implant which can facilitate nerve repair will need to provide chemical and/or physical cues in order to allow neurons, neuronal tissue and/or axons to regenerate and/or proliferate within an artificial environment of said pharmaceutical composition and/or implant.

Some of the challenges in providing an effective pharmaceutical composition and/or implant for use in the treatment of spinal cord injury include, for example: (i) producing a biocompatible and concomitantly biodegradable composition that will minimize inflammation and limit neuronal death; (ii) providing a composition that is patient compliant by limiting the number of surgical interventions; (iii) providing a composition that limits the amount of surgical interference with surrounding healthy tissue; (iv) providing a composition that will allow, during surgery, the preservation of the blood-spinal barrier; (v) providing a composition which facilitates reduction in glial scar tissue formation; (vi) providing a composition having physicochemical properties that will facilitate adhesion and/or proliferation sites for neuronal growth and/or repair facilitating extension of neuronal processes into the lesion site; and (vii) providing a composition having physico-chemical properties mimicking human or animal spinal cord to decrease inflammation and/or rejection and to facilitate growth and repair of neuronal tissue.

There remains an urgent need for the development of a pharmaceutical composition and/or an implant for use in the treatment of spinal cord injury which can at least ameliorate or partially address one of the above mentioned or other challenges known in the prior art.

SUMMARY

In broad terms, and in accordance with a first aspect of this disclosure there is provided a pharmaceutical composition comprising polyacrylonitrile (PANi) and/or elastin (E) and/or collagen (C), together forming a polyacrylonitrile (PANi) and/or elastin (E) and/or collagen (C) polymer network in the form of PANi-E and/or PANi-C and/or PANi-E-C, respectively.

The pharmaceutical composition wherein the polyacrylonitrile (PANi) may be crosslinked via a crosslinking agent such that the PANi-E and/or PANi-C and/or PANi-E-C may form a crosslinked, porous, semi-interpenetrating (or interpenetrating) polymer network (xpi), wherein the crosslinked polyacrylonitrile (PANi) associates and/or bonds and/or connects with the elastin (E) and/or collagen (C) facilitating reorientation of the secondary structure of proteins elastin (E) and collagen (C).

The association and/or bond formation and/or connection between polyacrylonitrile (PANi) and/or elastin (E) and/or collagen (C) may be via covalent and/or non-covalent and/or non-bonding interactions. The covalent interactions may include for example: σ-bonds and/or π-bonds. The non-covalent interactions may include for example: ionic, ion-dipole, hydrogen bonding, dipole-dipole, van der Waals, dipole-induced-dipole, London dispersion, π-π interactions, π-stacking, cation-π interactions and anion-π interactions.

The non-bonding interactions may arise from the stretching, bending and torsional strain experienced by PANi molecules in close vicinity of proteins elastin (E) and/or collagen (C) and vice versa.

The Applicant unexpectedly and surprisingly found that the reorientation of the secondary structure of protein elastin (E) within PANi-E resulted in the concentration dependent secondary structure of protein elastin (E) being such that the concentration of random coils>β-sheets>α-helix>β-turns. The symbol ">" denotes the term "greater than" throughout this specification.

The Applicant unexpectedly and surprisingly found that the reorientation of the secondary structure of proteins collagen (C) within PANi-C resulted in the concentration dependent secondary structure of protein collagen (C) being such that the concentration of α-helix>random coils>β-turns>β-sheets.

The Applicant unexpectedly and surprisingly found that the reorientation of the secondary structure of proteins elastin (E) and collagen (C) within PANi-E-C resulted in the concentration dependent secondary structure of proteins elastin (E) and collagen (C) being such that the concentration of random coils>α-helix>β-sheets>β-turns.

The concentration dependent secondary structure of elastin (E) alone, prior to reorientation, is such that the concentration of β-sheets>random coils>α-helix>β-turns.

The concentration dependent secondary structure of collagen (C) alone, prior to reorientation, is such that the concentration of β-sheets>α-helix>random coils>β-turns.

The reorientation of elastin (E) and/or collagen (C) provides for the reorientated secondary structure of proteins elastin (E) and/or collagen (C) to approximate, or to be in, their native or natural form as naturally found in the extra cellular matrix (ECM) of a human or animal, providing spinomimetic properties (i.e. mimicking human or animal spinal cord).

The reorientation may be further facilitated by self-assembly.

The reorientation imparts to pharmaceutical composition unique and/or advantageous chemico-physical properties, including, but not limited to, providing elasticity and/or mechanical strength and/or deformation energy and/or rigidity and/or stiffness and/or firmness and/or resilience mimicking human or animal spinal cord tissue, and therein providing a spinomimetic pharmaceutical composition.

The pharmaceutical composition may be provided with a network of channels and/or tunnels imparting sponge-like characteristics thereto. The sponge-like pharmaceutical composition may be a neurosponge. The term "neurosponge" may be abbreviated where appropriate to "NS".

When the pharmaceutical composition is in use implanted into a human or animal body at, near, adjacent to, or in connection with, a spinal cord of said human or animal body, the channels and/or tunnels provide a pathway and/or route and/or conduit for nerve tissue and/or axonal growth and/or repair.

The channels and/or tunnels may include along their inner surfaces raised formations or protrusions. The raised formations or protrusions provide an anchoring means for nerve tissue or neuronal tissue, particularly axons, facilitating growth and/or repair. The protrusions inside the channels and/or tunnels facilitate providing a fibrous channeled and/or tunnel polymeric architecture which mimics human or animal spinal cord.

In accordance with a preferred embodiment of the first aspect of this disclosure there is provided a pharmaceutical composition comprising polyacrylonitrile (PANi), elastin (E), and collagen (C) together forming a polyacrylonitrile (PANi), elastin (E), collagen (C) polymer network (PANi-E-C).

The pharmaceutical composition wherein the polyacrylonitrile (PANi) may be crosslinked via a crosslinking agent to form a crosslinked, porous, semi-interpenetrating (or interpenetrating) polyacrylonitrile (PANi), elastin (E) and collagen (C) polymer network (xpi-PANi-E-C), wherein the crosslinked polyacrylonitrile (PANi) associates and/or bonds and/or connects with the elastin (E) and collagen (C) facilitating reorientation of the secondary structure of proteins elastin (E) and collagen (C).

The association and/or bond formation and/or connection between polyacrylonitrile (PANi) and elastin (E) and collagen (C) may be via covalent and/or non-covalent and/or non-bonding interactions. The covalent interactions may include for example: σ-bonds and/or π-bonds. The non-covalent interactions may include for example: ionic, ion-dipole, hydrogen bonding, dipole-dipole, van der Waals, dipole-induced-dipole, London dispersion, π-π interactions, π-stacking, cation-π interactions and anion-π interactions. The non-bonding interactions may arise from the stretching, bending and torsional strain experienced by PANi molecules in close vicinity of proteins elastin (E) and collagen (C) and vice versa.

The Applicant unexpectedly and surprisingly found that the reorientation of the secondary structure of proteins elastin (E) and collagen (C) within xpi-PANi-E-C resulted in the concentration dependent secondary structure of proteins elastin (E) and collagen (C) being such that the concentration of random coils>α-helix>β-sheets>β-turns.

The concentration dependent secondary structure of elastin (E) alone, prior to forming part of the xpi-PANi-E-C, is such that the concentration of β-sheets>random coils>α-helix>β-turns.

The concentration dependent secondary structure of collagen (C) alone, prior to forming part of the xpi-PANi-E-C, is such that the concentration of β-sheets>α-helix>random coils>β-turns.

The reorientation of both elastin (E) and collagen (C) provides for the reorientated secondary structure of proteins elastin (E) and collagen (C) to approximate, or to be in, their native or natural form as naturally found in the extra cellular matrix (ECM) of a human or animal.

The reorientation may be further facilitated by self-assembly.

The reorientation imparts to the xpi-PANi-E-C unique and/or advantageous chemico-physical properties, including, but not limited to, providing elasticity and/or mechanical strength and/or deformation energy and/or rigidity and/or stiffness and/or firmness and/or resilience mimicking human or animal spinal cord tissue, and therein providing a spinomimetic pharmaceutical composition.

The Applicant was surprised that the association and/or bond formation and/or connection between chemically neutral polyacrylonitrile (PANi) and elastin (E) and collagen (C), and subsequent reorientation of elastin (E) and collagen (C), would result in xpi-PANi-E-C having spinomimetic properties.

The crosslinking agent may be, but is not limited to, methylenebisacrylamide (MBAAm).

The xpi-PANi-E-C pharmaceutical composition may be provided with a network of channels and/or tunnels imparting sponge-like characteristics to the xpi-PANi-E-C. The sponge-like xpi-PANi-E-C may be a neurosponge. The term "neurosponge" may be abbreviated where appropriate to "NS".

When the xpi-PANi-E-C-NS/pharmaceutical composition is in use implanted into a human or animal body at, near, adjacent to, or in connection with, a spinal cord of said human or animal body, the channels and/or tunnels provides a pathway and/or route and/or conduit for nerve tissue and/or axonal growth and/or repair.

The channels and/or tunnels may include along their inner surfaces raised formations or protrusions. The raised formations or protrusions provide an anchoring means for nerve tissue or neuronal tissue, particularly axons, facilitating growth and/or repair. The protrusions inside the channels and/or tunnels facilitate providing a fibrous channeled and/or tunnel polymeric architecture which mimics human or animal spinal cord.

In accordance with a second aspect of this disclosure there is provided a pharmaceutical composition for use in the treatment of a spinal cord injury, the pharmaceutical composition for implantation into a human or animal body at, near, adjacent to, or in connection with, a spinal cord of said human or animal body, said pharmaceutical composition being according to the first aspect of the disclosure.

In accordance with a third aspect of this disclosure there is provided an implant for implantation into a human or animal body at, near, adjacent to, or in connection with, a spinal cord of said human or animal body, said implant comprising the pharmaceutical composition according to the first aspect of the disclosure.

The implant may further include a carrier and/or an excipient.

In accordance with a fourth aspect of this disclosure there is provided an implant for use in the treatment of a spinal cord injury, the implant being for implantation into a human or animal body at, near, adjacent to, or in connection with, a spinal cord of said human or animal body, said implant comprising the pharmaceutical composition according to the first aspect of the disclosure.

The implant may further include a carrier and/or excipient.

In accordance with a fifth aspect of this disclosure there is provided a use of polyacrylonitrile (PANi), elastin (E), and collagen (C), in the manufacture of a pharmaceutical composition to treat spinal cord injury in a human and/or animal.

The pharmaceutical composition may be according to the first aspect of the disclosure.

In accordance with a sixth aspect of this disclosure there is provided a method of producing the pharmaceutical composition according to the first aspect of this disclosure, the method comprising the following steps:
(i) dissolving elastin (E) and/or collagen (C) in an acidic aqueous medium to form a first solution;
(ii) adding acrylonitrile to the first solution and mixing to form a second solution, which second solution may be agitated/mixed until homogenous; and
(iii) allowing polymerization and/or crosslinking to take place to form a crosslinked, porous, interpenetrating polyacrylonitrile (PANi), and/or elastin (E) and/or collagen (C) polymer network.

In accordance with a preferred embodiment of the sixth aspect of this disclosure there is provided a method of producing the pharmaceutical composition according to the preferred first aspect of this disclosure, the method comprising the following steps:
(i) dissolving elastin (E) and/or collagen (C) in an acidic aqueous medium to form a first solution;
(ii) adding acrylonitrile to the first solution and mixing to form a second solution, which second solution may be agitated/mixed until homogenous;
(iii) adding a initiator, for example, but not limited to, ammonium persulphate (APS), to the homogenous second solution,
wherein the initiator initiates free radical polymerization of the acrylonitrile to form an interpenetrating polyacrylonitrile (PANi), elastin (E) and collagen (C) polymer network (iPANi-E-C); and
(iv) adding a crosslinking agent, for example, but not limited to methylenebisacrylamide (MBAAm),
wherein the crosslinking agent crosslinks the polyacrylonitrile (PANi) to form a crosslinked, porous, interpenetrating polyacrylonitrile (PANi), elastin (E) and collagen (C) polymer network (xpi-PANi-E-C).

Steps (i) to (iv) may take place in sequence beginning at Step (i) and ending in Step (iv).

Within the sequence, Steps (iii) and (iv) may take place concomitantly.

The method may further include Step (v): adding an accelerant, for example, tetramethylethylenediamine (TEMED), wherein Step (v) takes place after Step (iv).

The acidic aqueous medium of Step (i) may be an aqueous acetic acidic medium. Step (i) may include the addition of excess glacial acetic acid to prevent precipitation of elastin (E) and/or collagen (C) from the first solution.

The method may further include Step (vi): pouring the xpi-PANi-E-C into moulds, preferably, polyethylene moulds, and allowing the same to set (wherein further polymerization takes place) forming a porous xpi-PANi-E-C sponge. Preferably the xpi-PANi-E-C is allowed to set overnight, further preferably, under room temperature conditions.

The method may further include Step (vii): washing the porous xpi-PANi-E-C sponge, preferably with double distilled water.

The method may further include Step (viii): freezing the washed xpi-PANi-E-C sponge between about −80° C. and −60° C., preferably for a time period of between about 8 to 12 hours.

The method may further include Step (ix): lyophilizing the xpi-PANi-E-C sponge, preferably at about 25 mmtorr for about 24 hours.

There is provided any one of the first to sixth aspects of this disclosure substantially as herein described, illustrated and/or exemplified with reference to any one of the accompanying figures and/or examples.

BRIEF DESCRIPTION

Embodiments of the disclosure will be described below by way of non-limiting examples only, and with reference to the accompany drawings in which:

FIG. 1 shows a typical force-distance profile representing the compression mechanical testing performed on the spinomimetic scaffolds. a) the area between anchors 1 and 2 (shaded part of the figure) represents the deformation energy while the gradient corresponds to rigidity gradient. The highest point in the curve corresponds to the maximum load experienced by the sample under the applied strain. b) the ratio of area 2 (between anchor 2 and 3) and area 1 (between area 1 and 2) represents matrix resilience of the scaffold.

Figure 13:
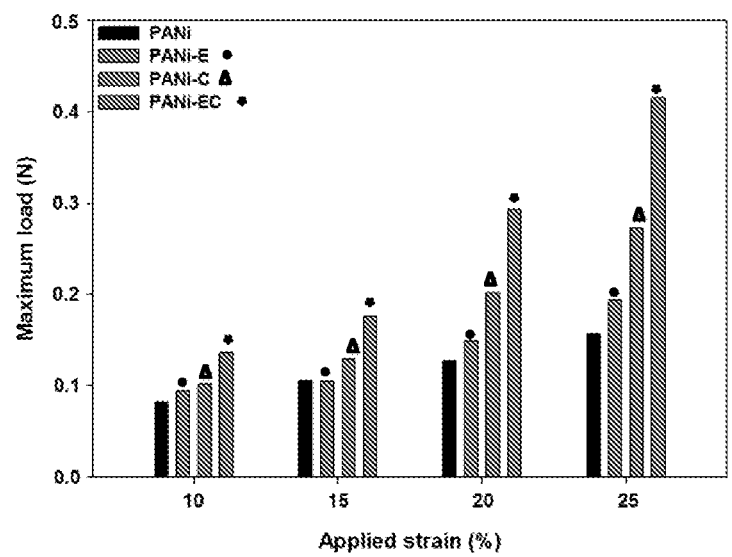
Figure 13:
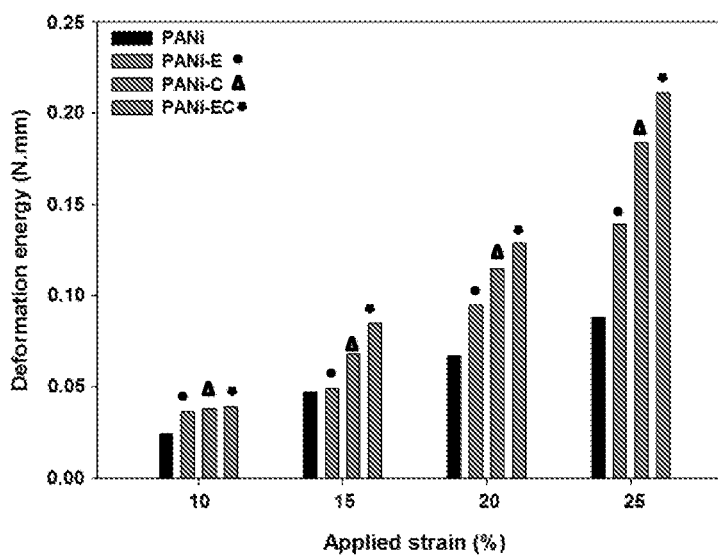
Figure 13:
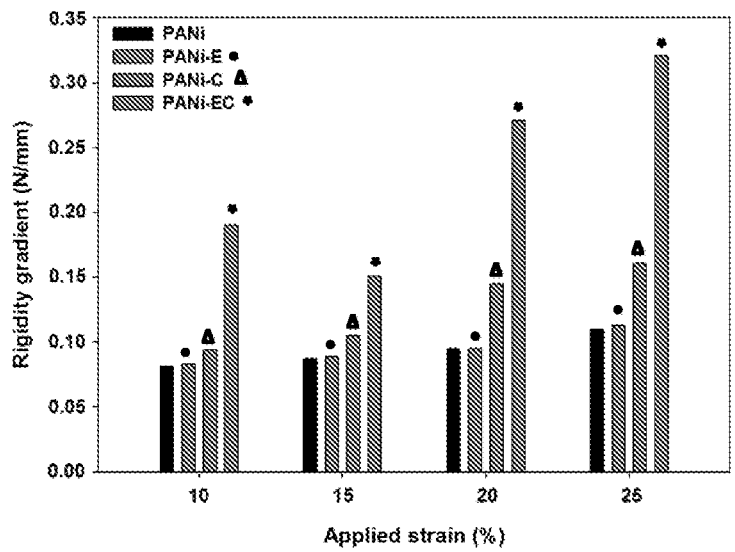
Figure 13:
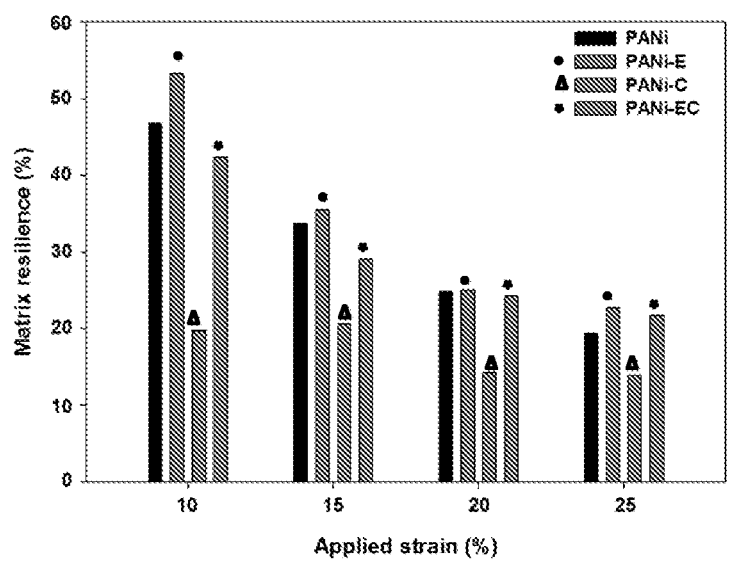

FIG. 13 shows physico-mechanical properties of the PANi neurosponge, the PANi-E neurosponge, the PANi-C neurosponge and the xpi-PANi-E-C neurosponge (labelled as PANi-EC) according to this disclosure under partial applied strain values of 10-25% ($SD_{(ML)} \leq 0.04$; $SD_{(DE)} \leq 0.05$; $SD_{(RG)} \leq 0.08$; $SD_{(MR)} \leq 9.2$; n=3), wherein (a) shows maximum load, (b) shows deformation energy, (c) shows rigidity gradient, and (d) shows matrix resilience.

Figure 14:
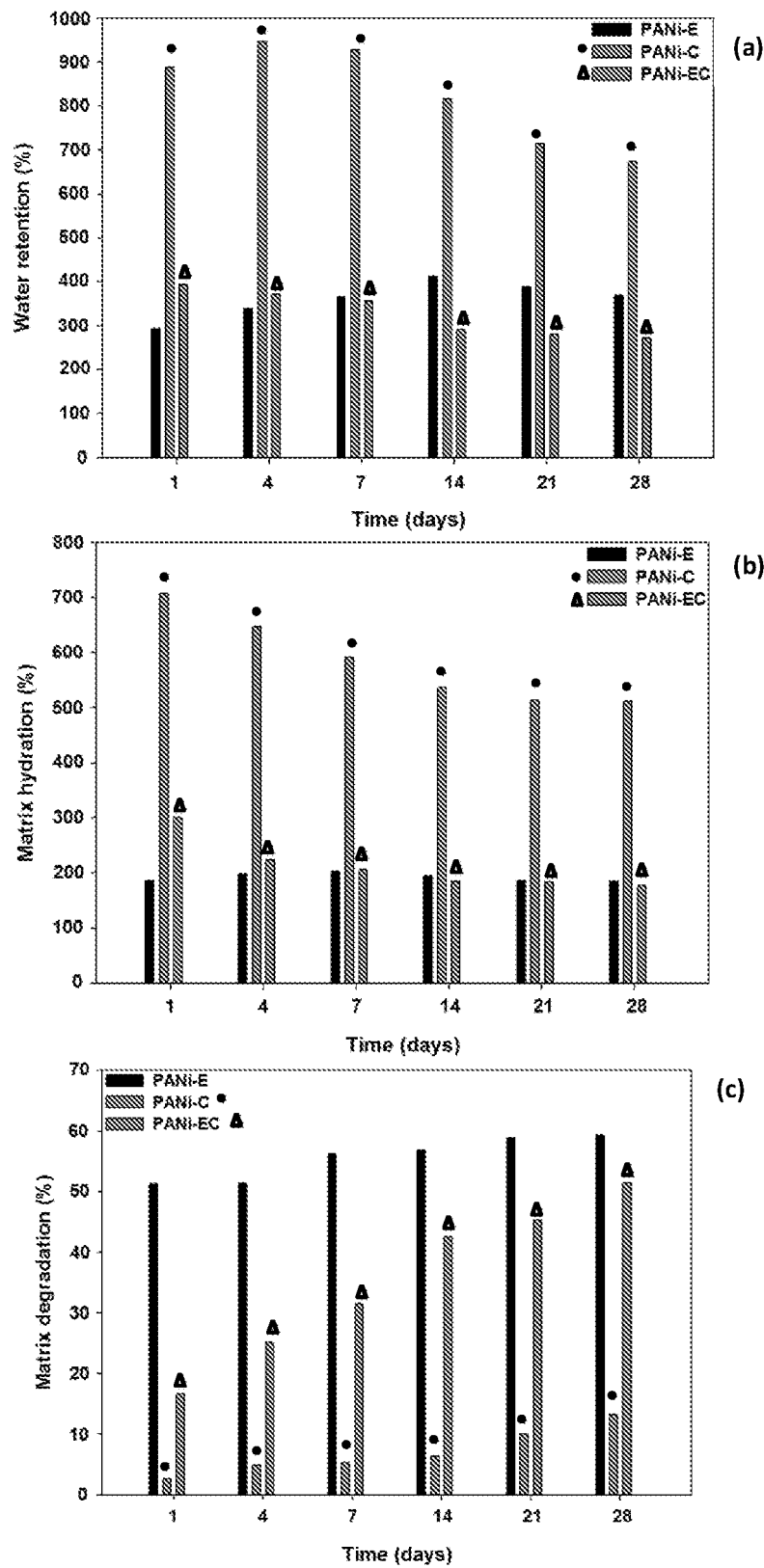

FIG. 14 shows a bar chart depicting matrix hydration and degradation profiles of the PANi-E neurosponge, the PANi-C neurosponge and the xpi-PANi-E-C neurosponge (labelled as PANi-EC) ($SD_{(WR)} \leq 202$; $SD_{(MH)} \leq 118$; $SD_{(MD)} \leq 6$; n=3), wherein (a) shows water retention, (b) shows matrix hydration, and (c) shows matrix degradation.

Figure 15:
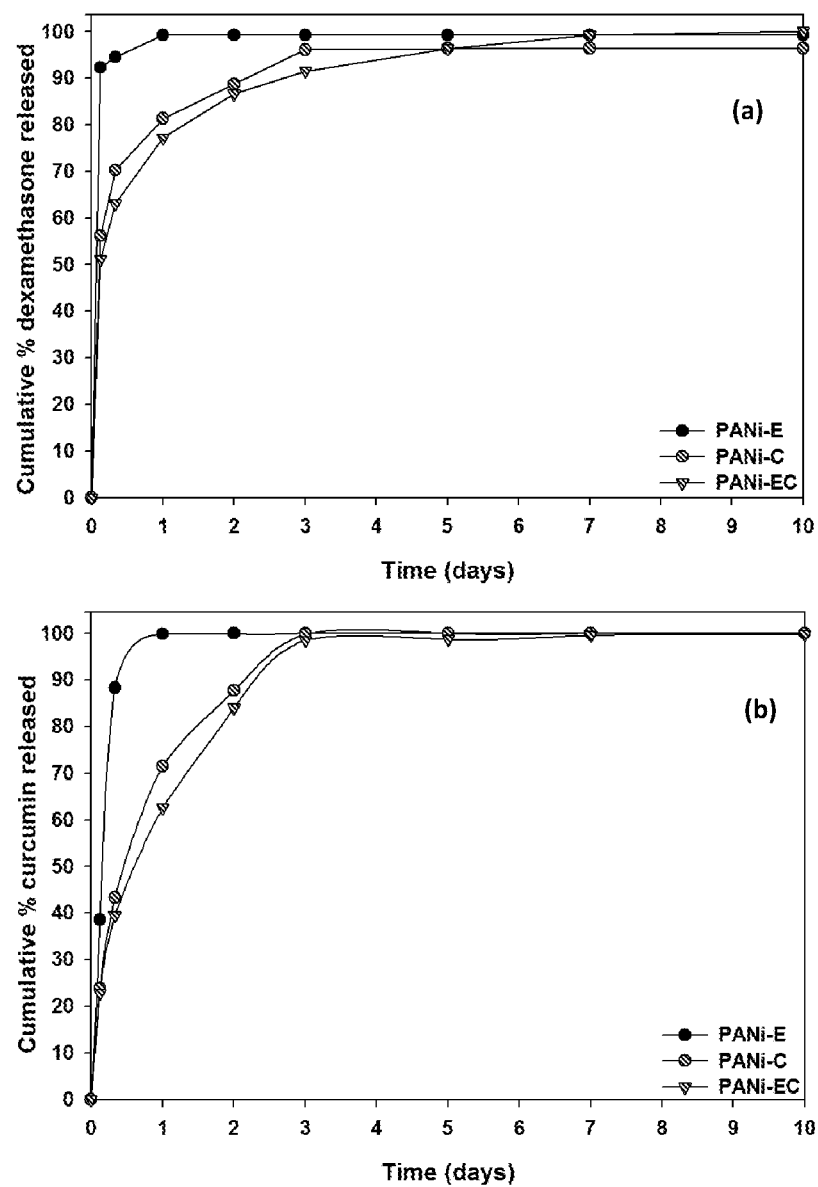

FIG. 15 shows drug release profiles of the PANi-E neurosponge, the PANi-C neurosponge and the xpi-PANi-E-C neurosponge (labelled as PANi-EC) ($SD_{(DEX)} \leq 6.6$; $SD_{(CURC)} \leq 4.3$; n=3), wherein (a) shows dexamethasone release and (b) shows curcumin release.

Figure 16:
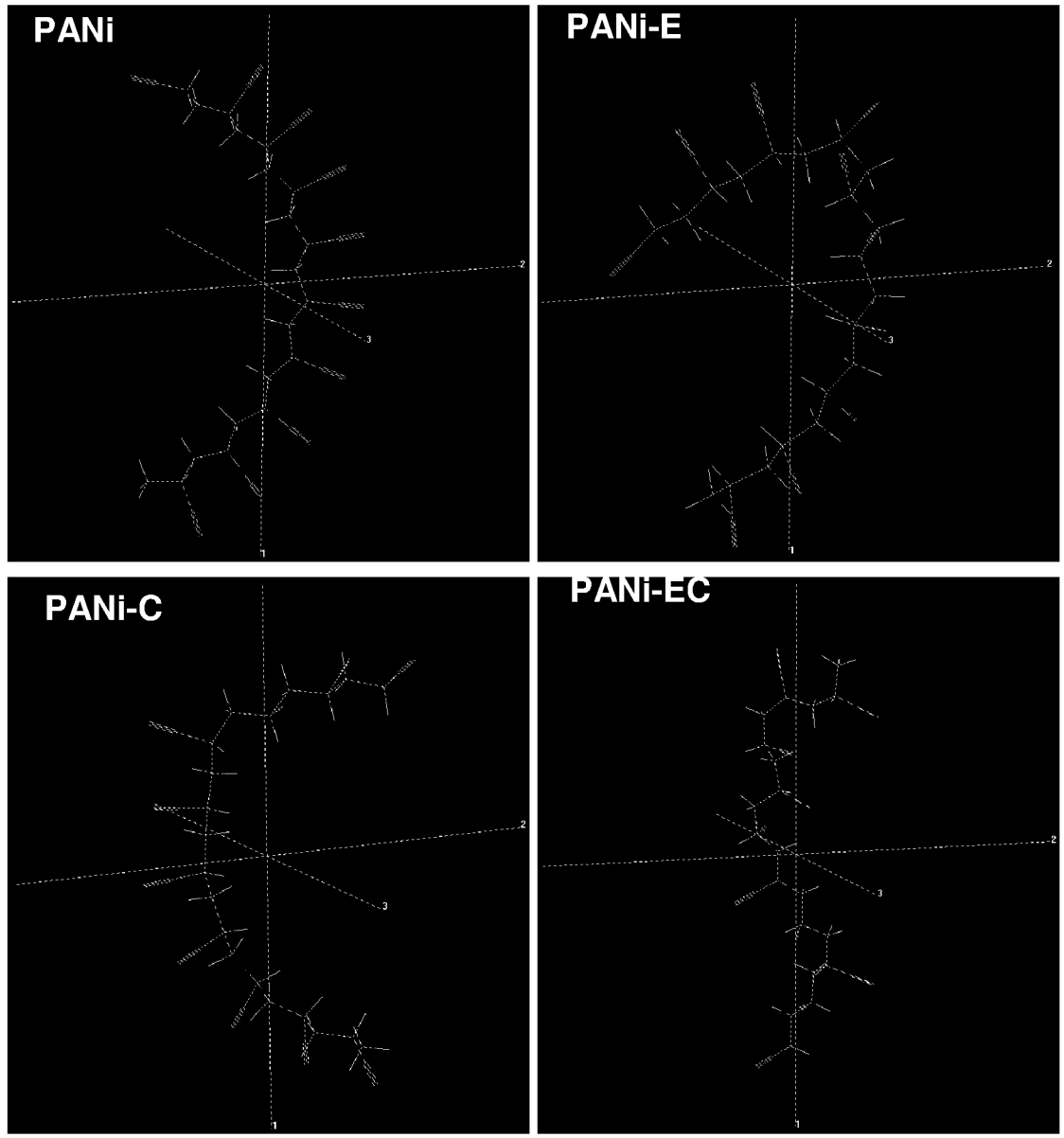

FIG. 16 indicates visualization of inertial axes of PANi in vicinity of the peptide molecules from molecular mechanics simulations showing PANi (top left), PANi-E (top right), PANi-C (bottom left), xpi-PANi-E-C (bottom left) (labelled as PANi-EC).

Figure 17:
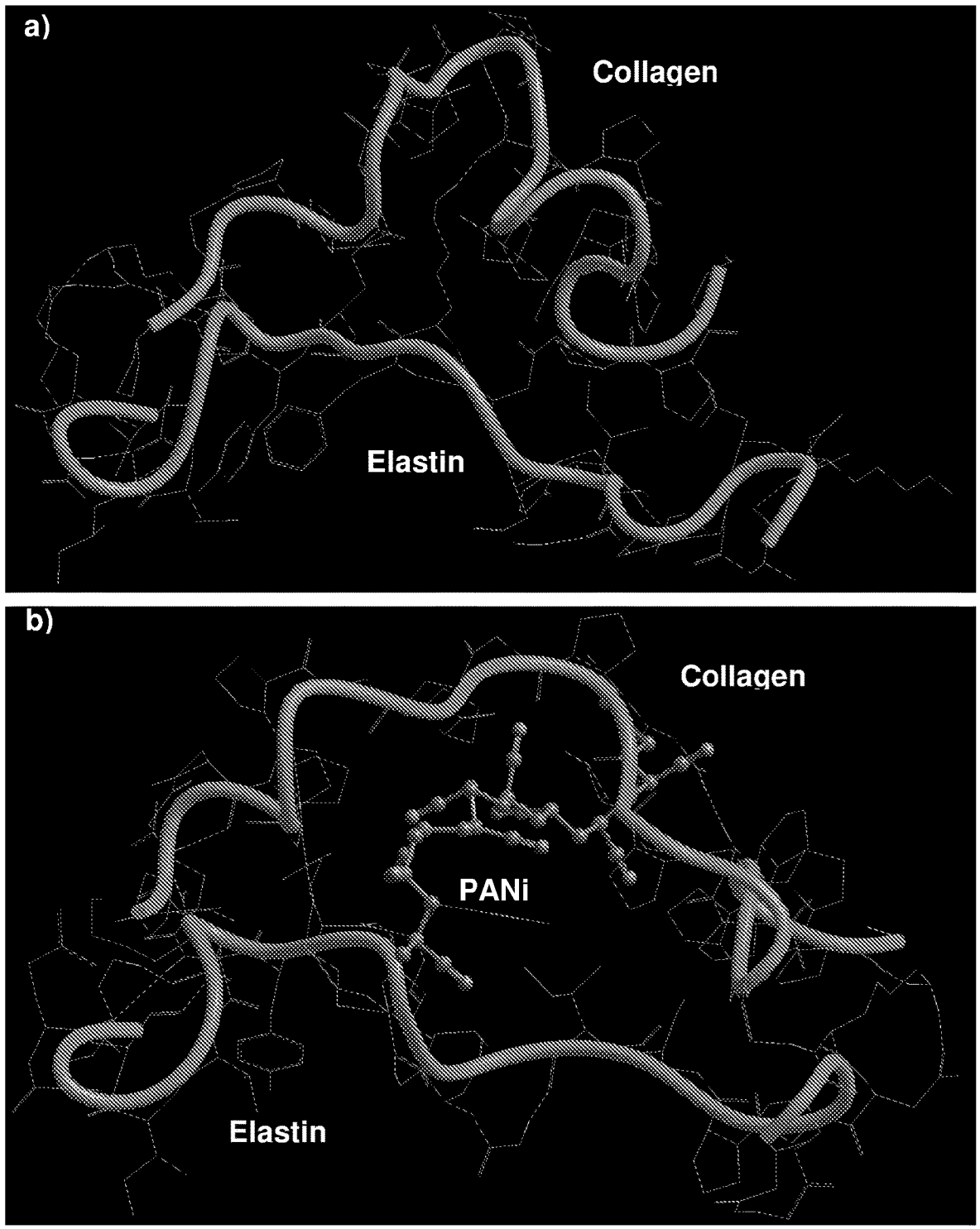

FIG. 17 indicates visualization of geometrical preferences of a) collagen-elastin; and b) PANi-collagen-elastin molecular complexes after energy minimization in vacuum. PANi showed in ball-and-stick rendering.

Figure 18:
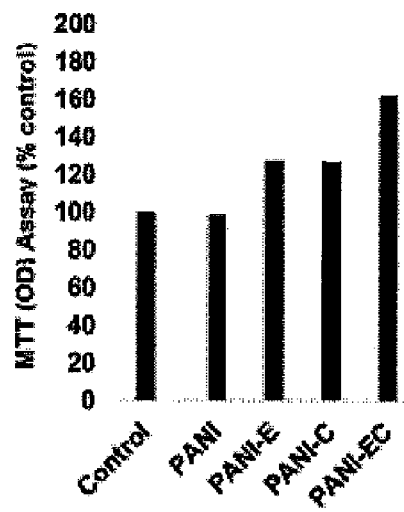

FIG. 18 shows a representation of the 3-(4,5-dimethylthiazol-2-yl)-2,5-diphenyltetrazolium bromide (MTT) assay showing the proliferative studies (SD≤14; n=3).

Figure 19:
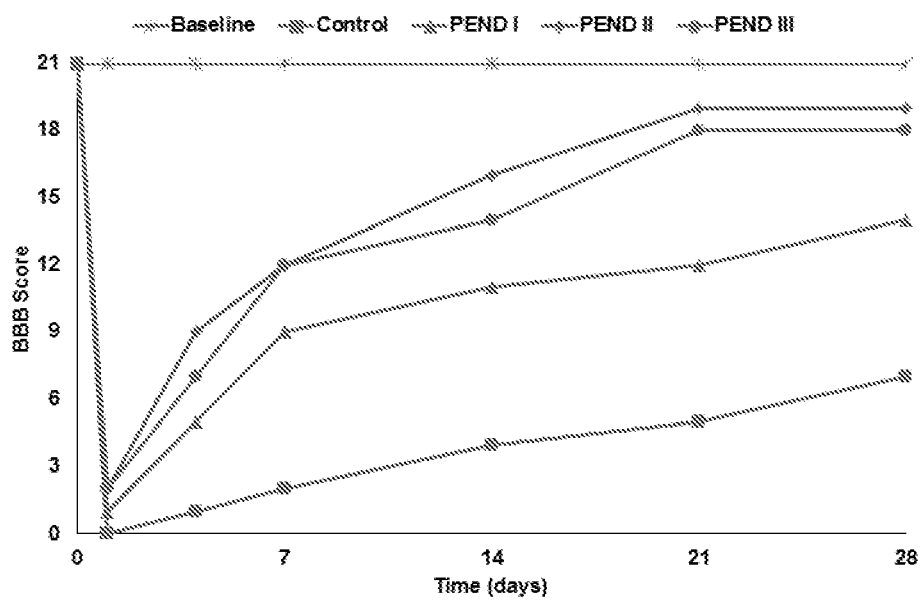

FIG. 19 Line graph showing changes in Basso, Beattie, Bresnahan (BBB) locomotor scores for both treatment groups post-treatment (SD≤1; n≥3).

Figure 20:
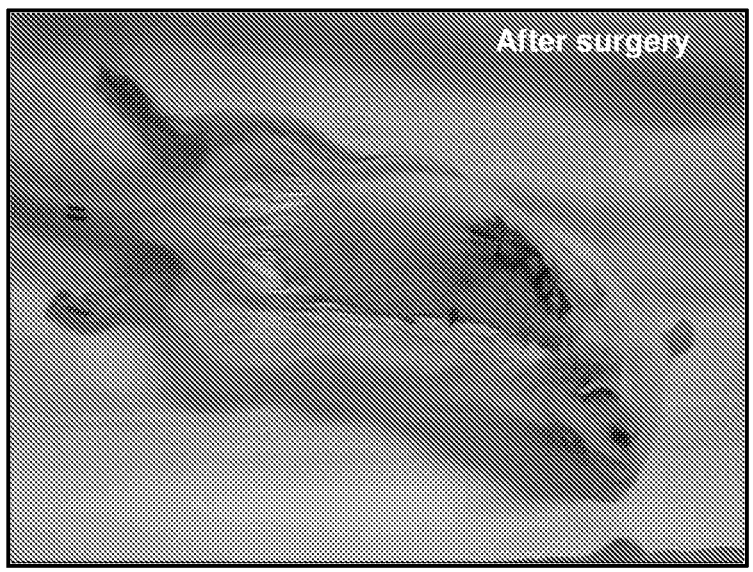
Figure 20:
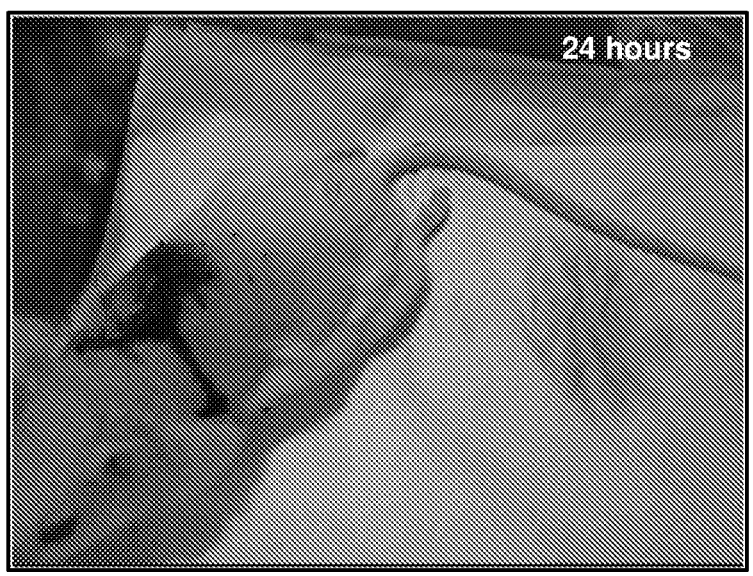
Figure 20:
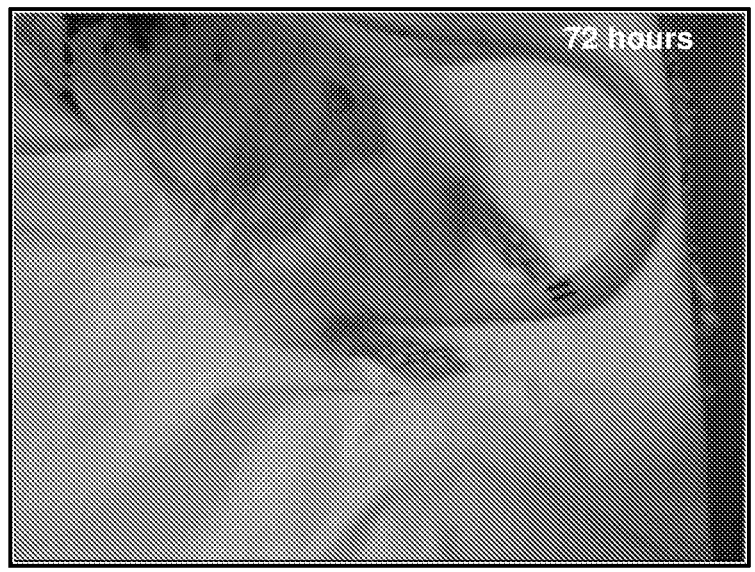
Figure 20:
Figure 20:
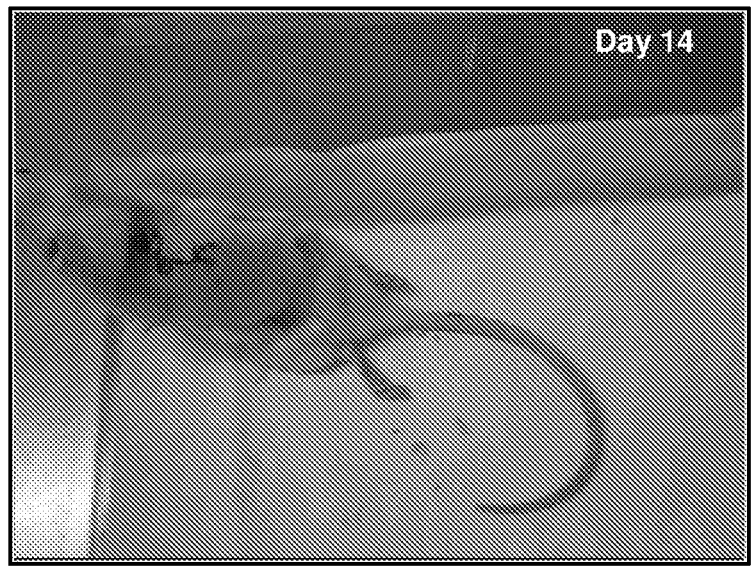
Figure 20:
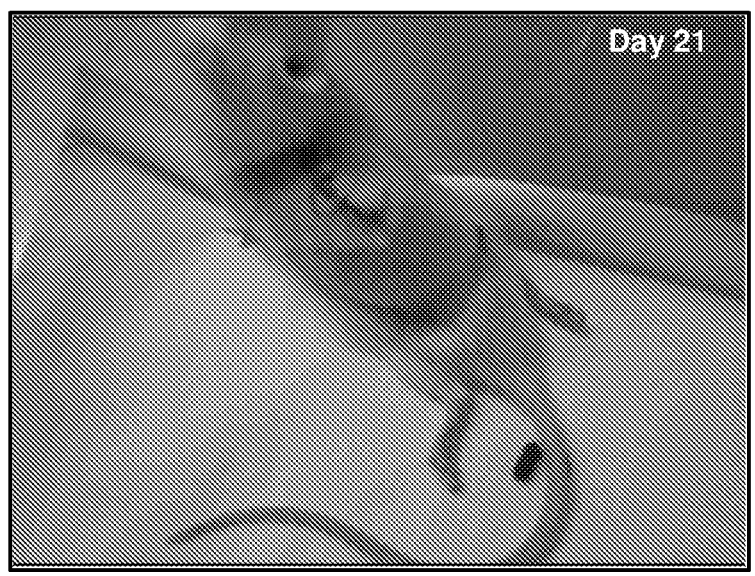
Figure 20:
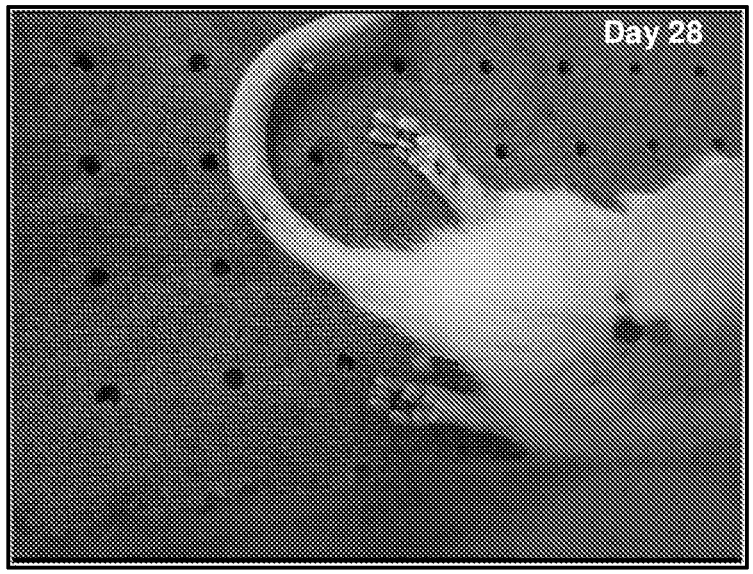
Figure 20:
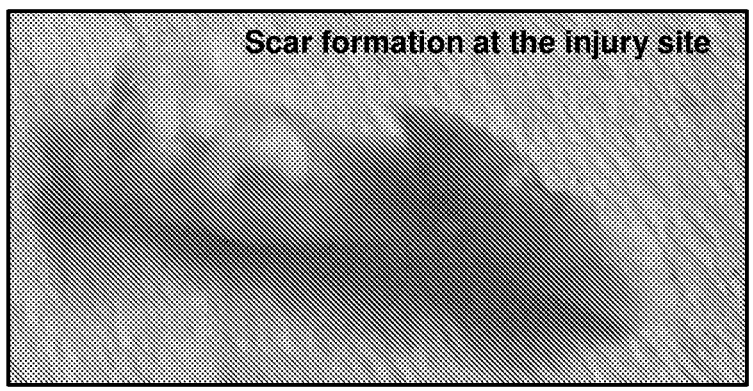

FIG. 20 shows sequential presentation (A) to (H) of the extent of functional recovery over a 28-day duration post-spinal cord injury (SCI) in the control group (Group 0)

Figure 21:
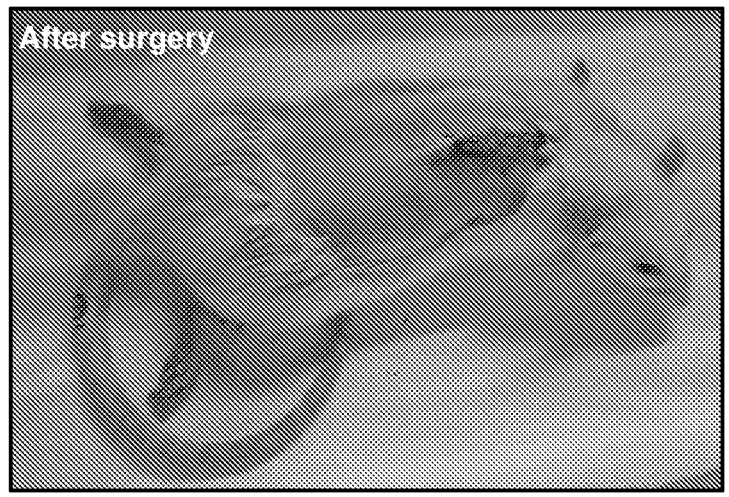
Figure 21:
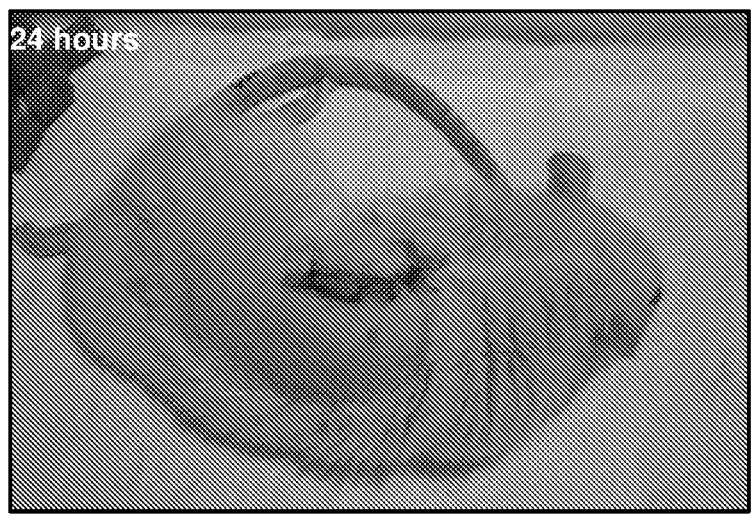
Figure 21:
Figure 21:
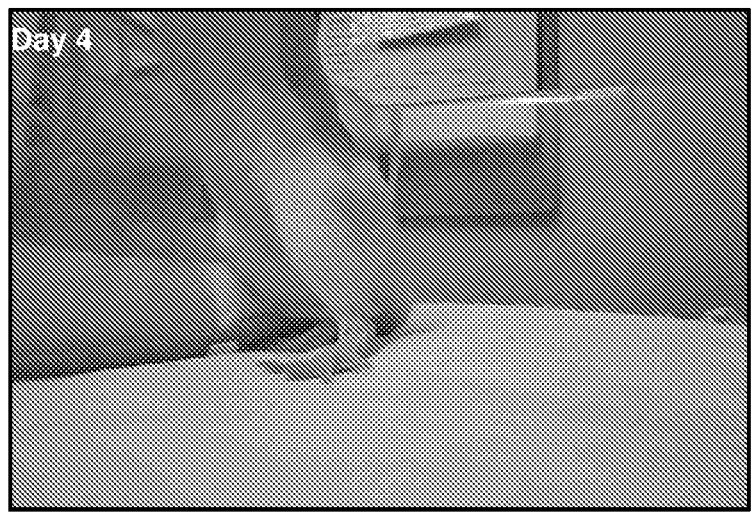
Figure 21:
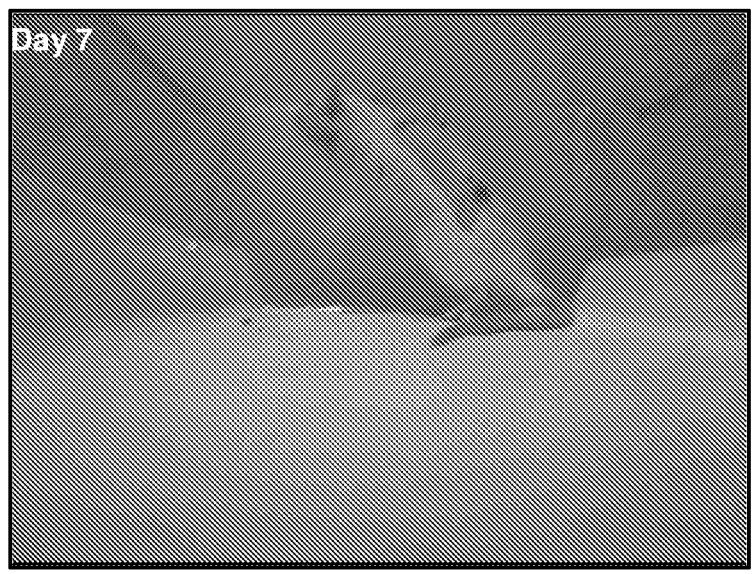
Figure 21:
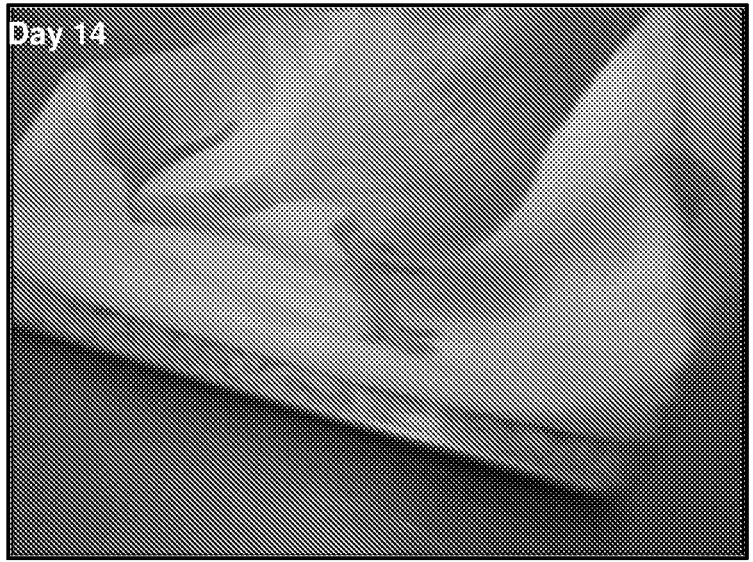
Figure 21:
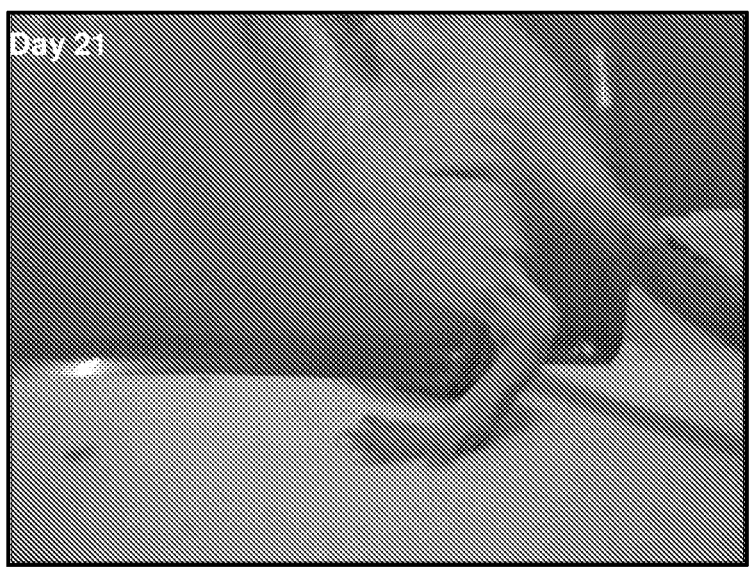
Figure 21:
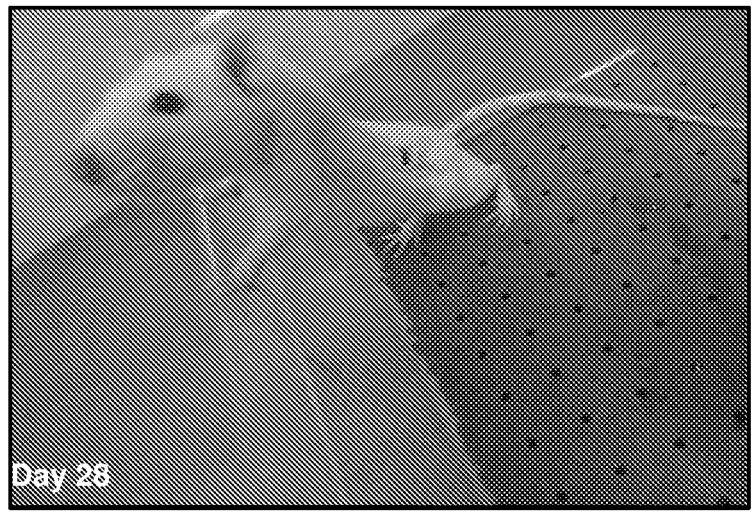
Figure 21:

FIG. 21 shows sequential presentation (A) to (I) of the extent of functional recovery over a 28-day duration post-SCI in the xpi-PANi-E-C group.

Figure 22:
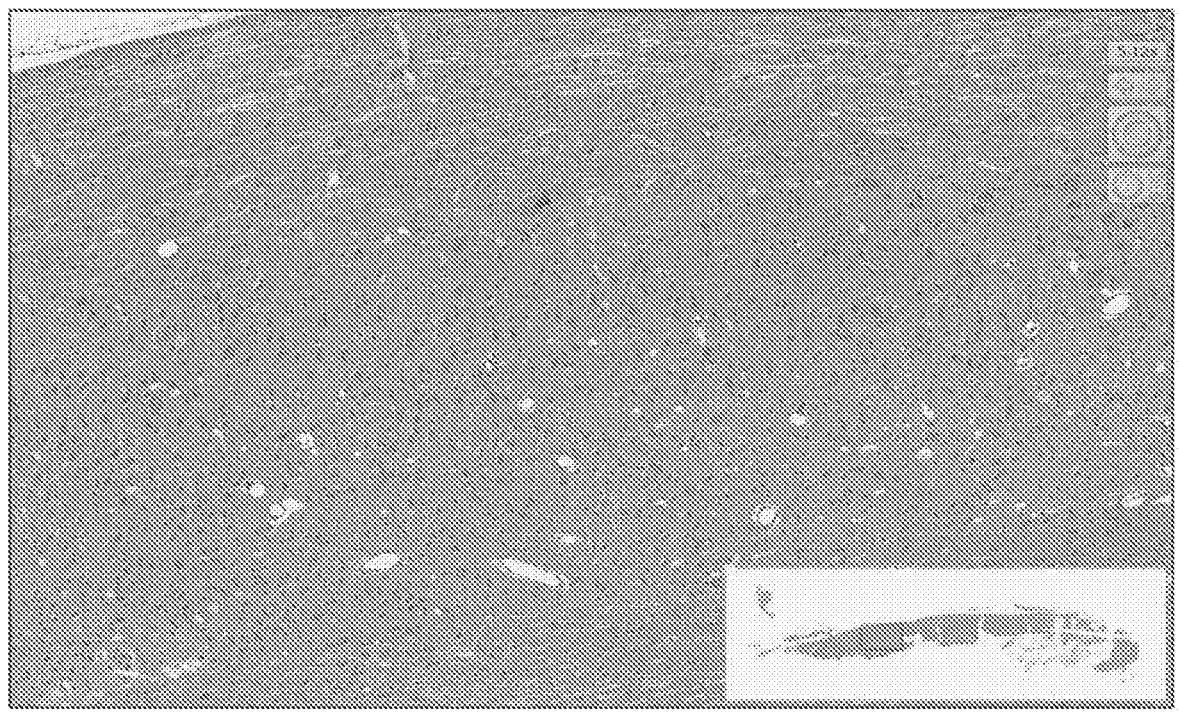

FIG. 22 shows a hematoxylin & eosin (H&E) specimen baseline; L2. 5× Objective: NAD, highlighting the morphologically unremarkable spinal cord specimen.

Figure 23:
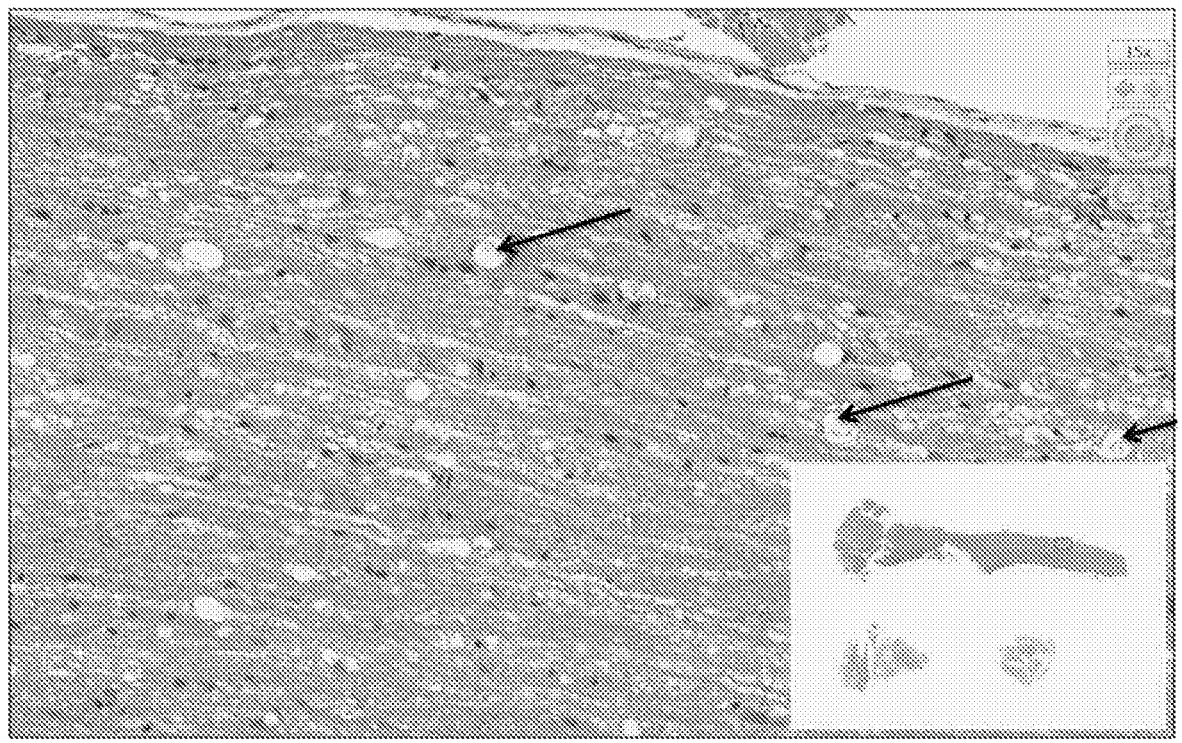

FIG. 23 shows an H&E specimen—xpi-PANi-E-C-B; L2. 30× Objective: Grade 2, highlighting numerous degenerate nerve fibres (arrows).

Figure 24:
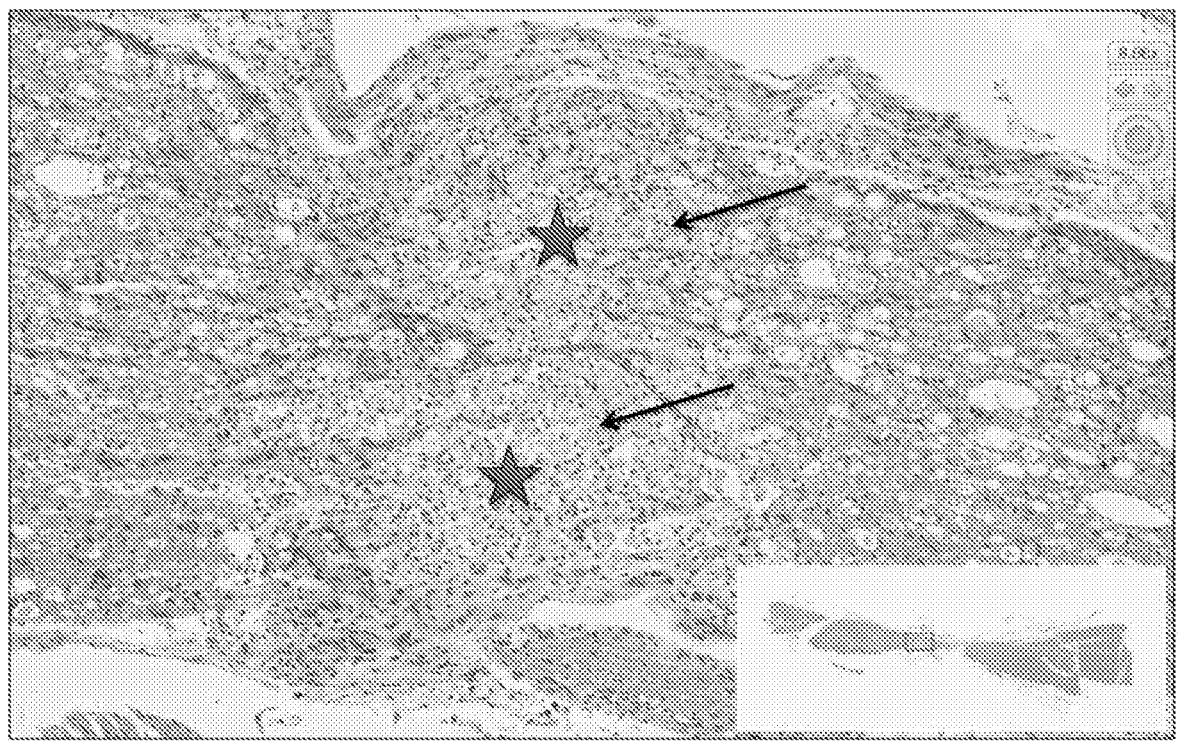

FIG. 24 shows an H&E specimen—control; L3. 8× Objective: Grade 4. Note the total transverse transection of nerve, with numerous degenerate nerve fibres, area of total architectural disruption/loss (stars) and replacement by vacuolated gitter cells (arrows).

Figure 25:
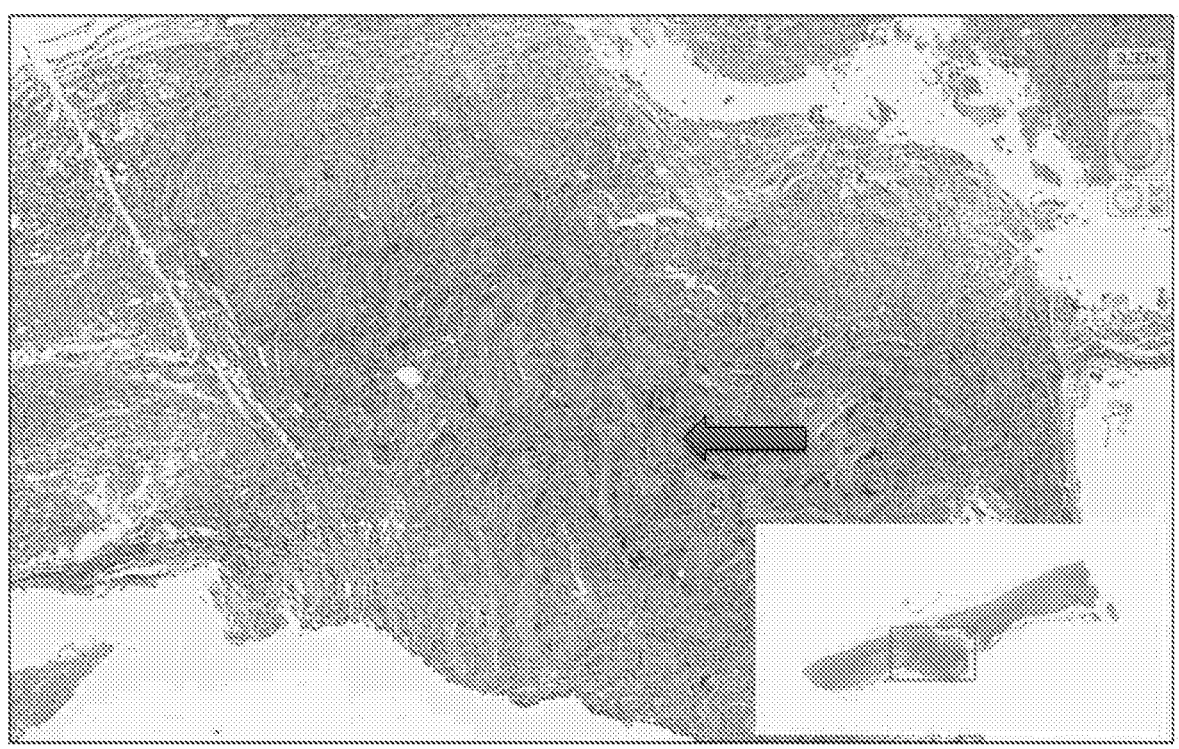

FIG. 25 shows an H&E specimen xpi-PANi-E-C-A; L3. 3× Objective: Grade 5. Note the total transverse transection of nerve and replacement by a mass of (presumptive) regenerating neuroblasts (thick arrow).

Figure 26:
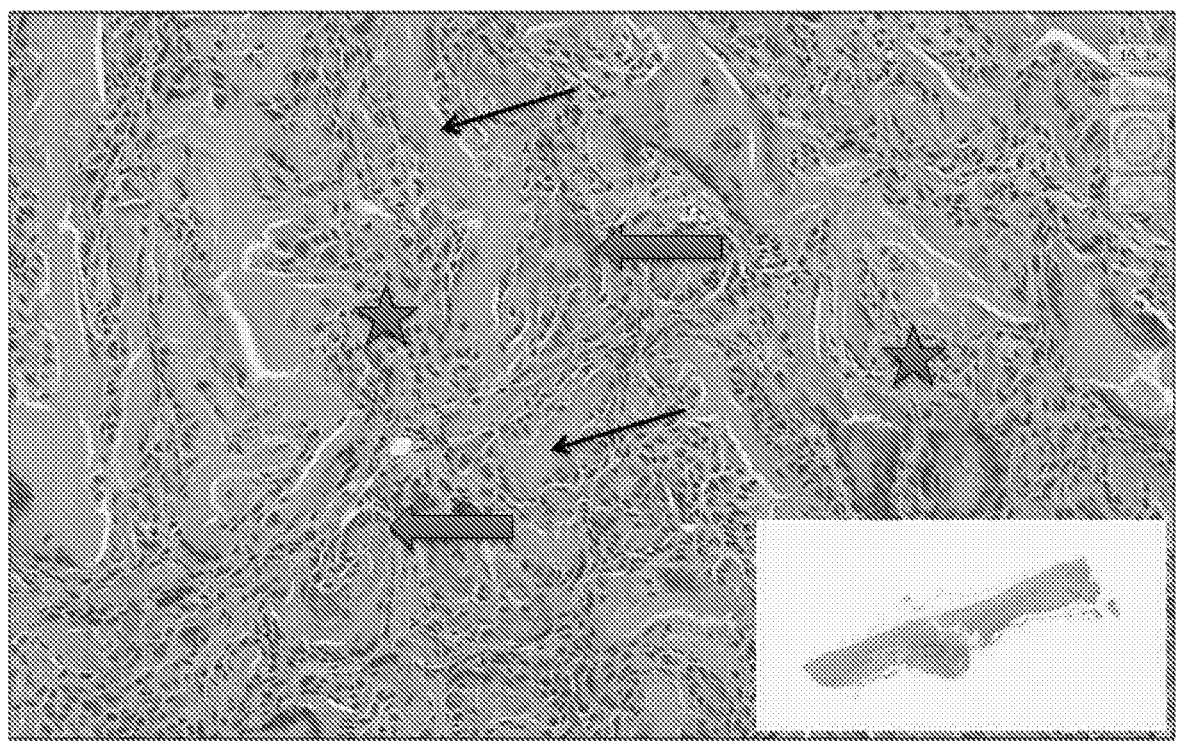

FIG. 26 shows an H&E specimen xpi-PANi-E-C-A; L3. 16× Objective: Grade 5. Note the total transverse transection of nerve, with numerous degenerate nerve fibres, area of total architectural disruption/loss (stars), and replacement by eosinophilic extra-cellular matrix (arrows) and multinucleate (presumptive) regenerate neuroblasts (large arrows).

Figure 27:
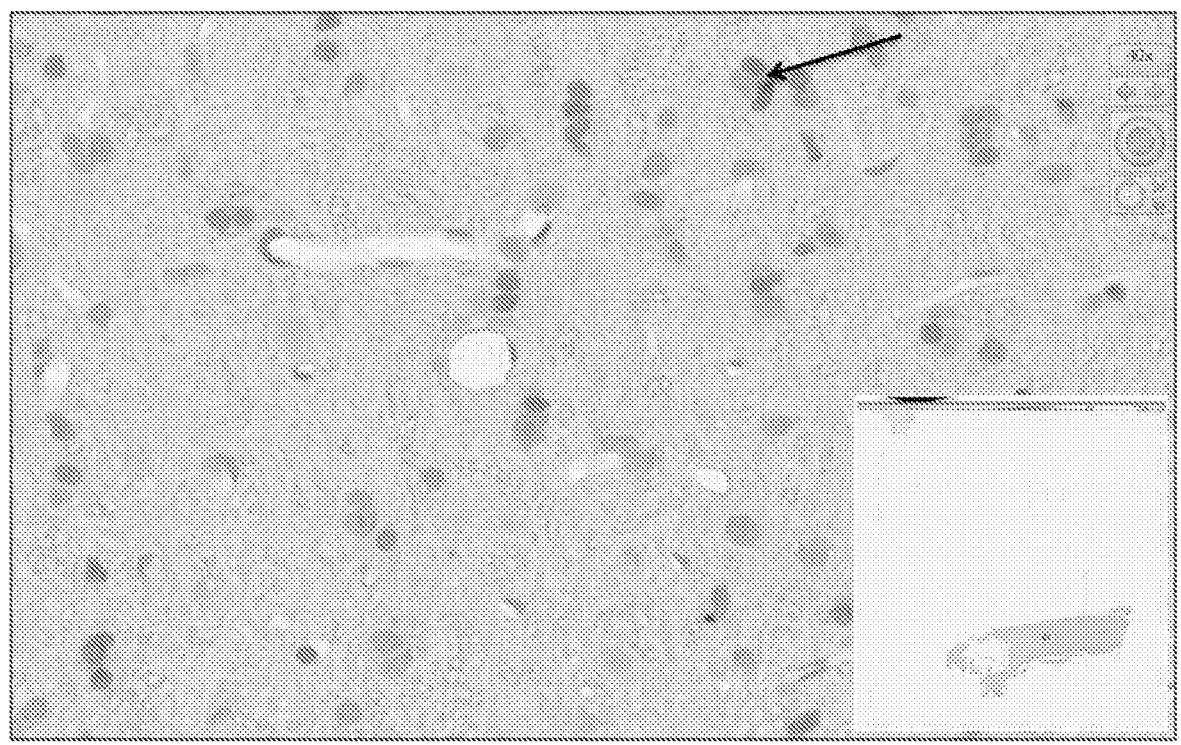

FIG. 27 shows an ED1 specimen Baseline; L2. 40× Objective: Grade 0. Note the low number of scattered positive glial cells (arrow).

Figure 28:
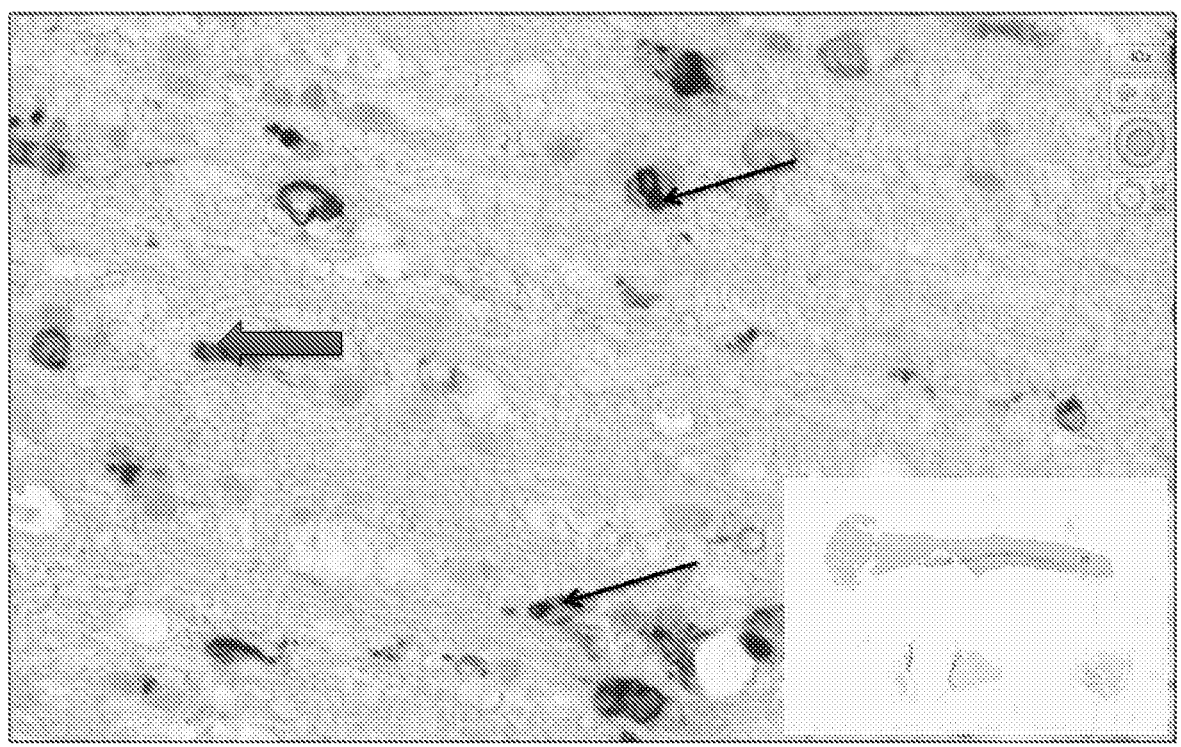

FIG. 28 shows an ED1 specimen xpi-PANi-E-C-B; L1. 40× Objective: Grade 2. Note the positive glial cells (arrows) and endothelial cell (thick arrow).

Figure 29:
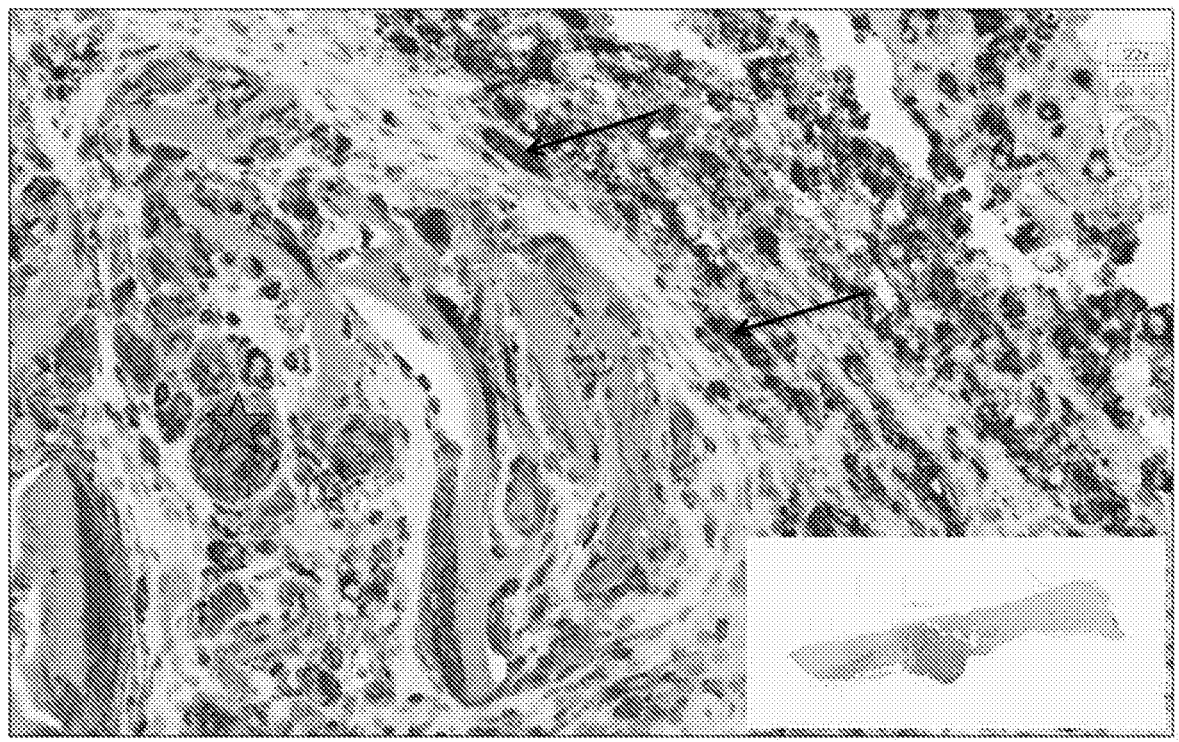

FIG. 29 shows an ED1 specimen xpi-PANi-E-C-A; L1. 40× Objective: Grade 4. Note the myriad and often degenerate/degenerating positive glial cells (arrows), in addition to the presence of positive multinucleate cells (star), indicating the presence of histiocytic marker expression within multinucleate gitter cells and/or primitive neuroblasts.

Figure 30:
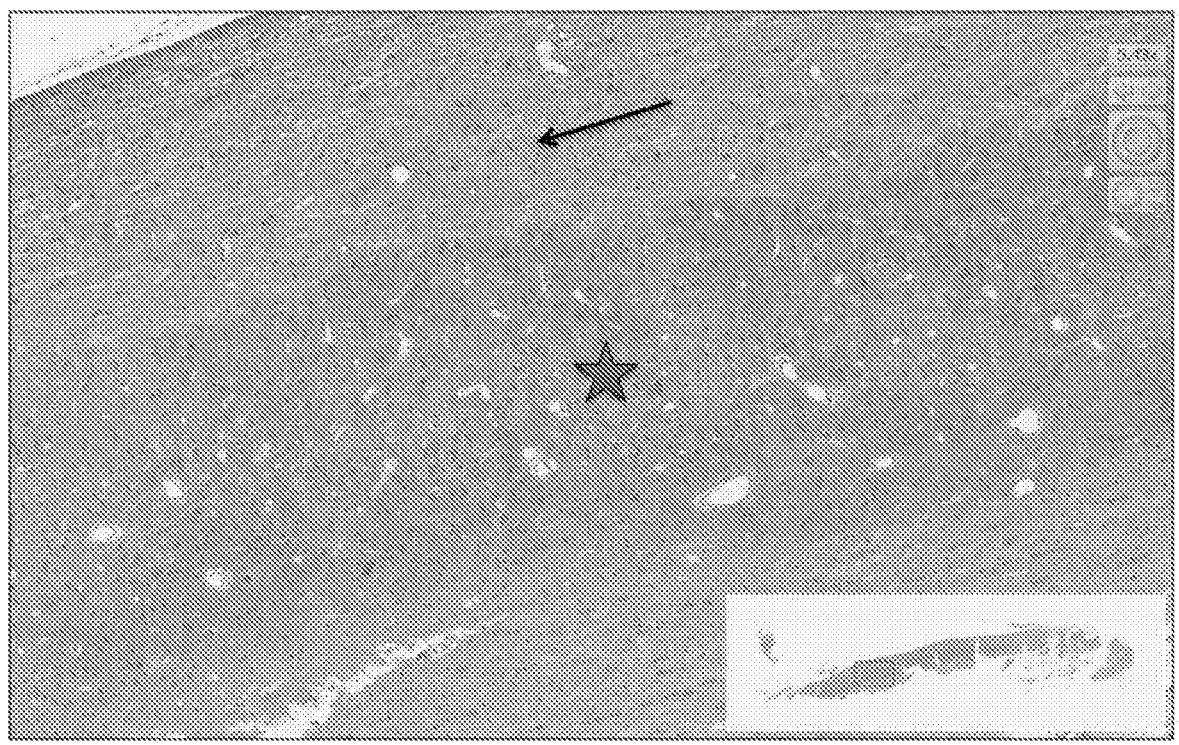

FIG. 30 shows an inducible nitric oxide synthase (iNOS) specimen Baseline; L2. 5× Objective: Grade 0. Note the baseline level of staining throughout intra- and extra-cellular components of the white (arrow) and grey (star) matter.

Figure 31:
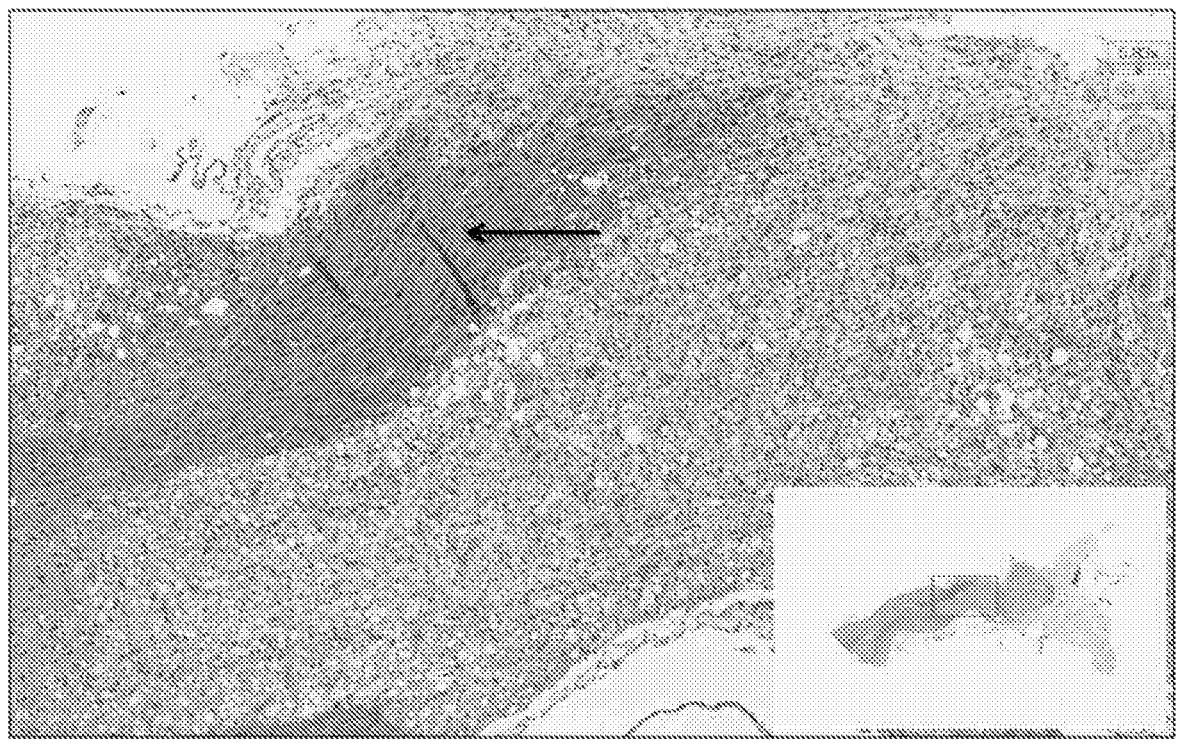

FIG. 31 shows an iNOS specimen xpi-PANi-E-C-C; L2. 5× Objective: Grade 2. Note the increased intensity of staining within intact and extra-lesional white matter (arrow).

Figure 32:
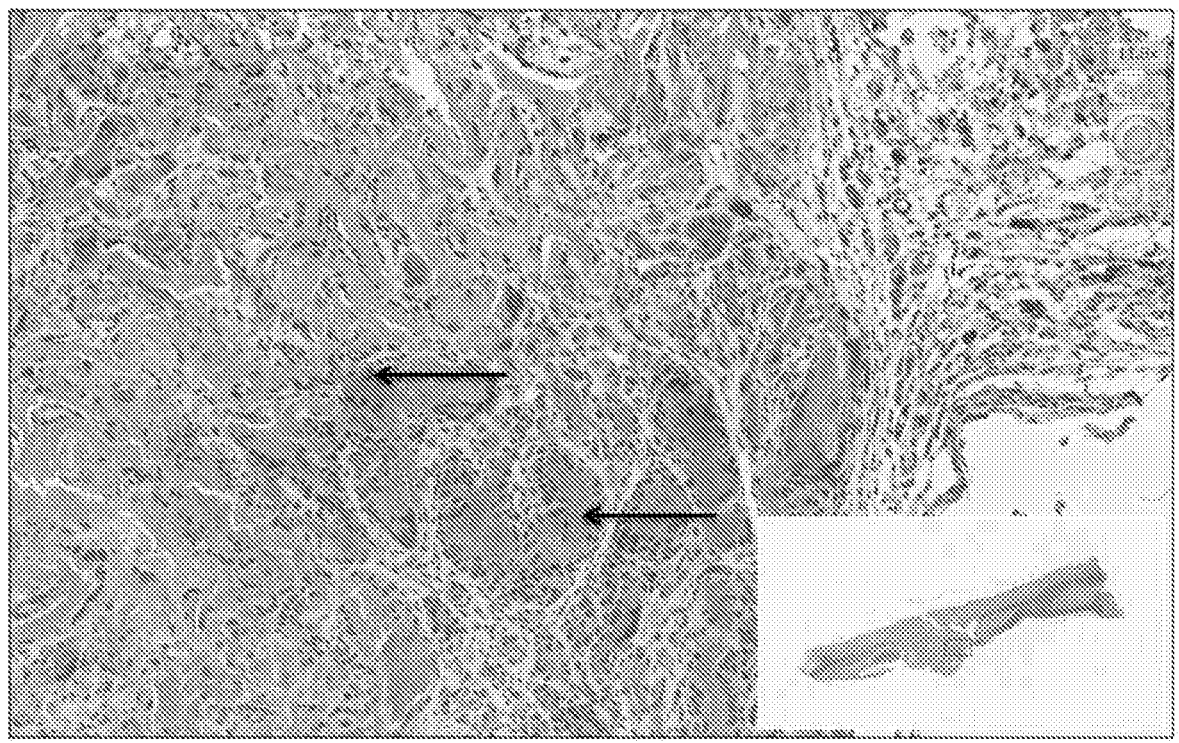

FIG. 32 shows a calcium-activated nonlysosomal neutral proteases (calpain) specimen xpi-PANi-E-C-A; L1. 10× Objective: Grade 1. Note the minimal presence of intra-cellular staining (red) within multinucleate giant cells (arrows).

Figure 33:
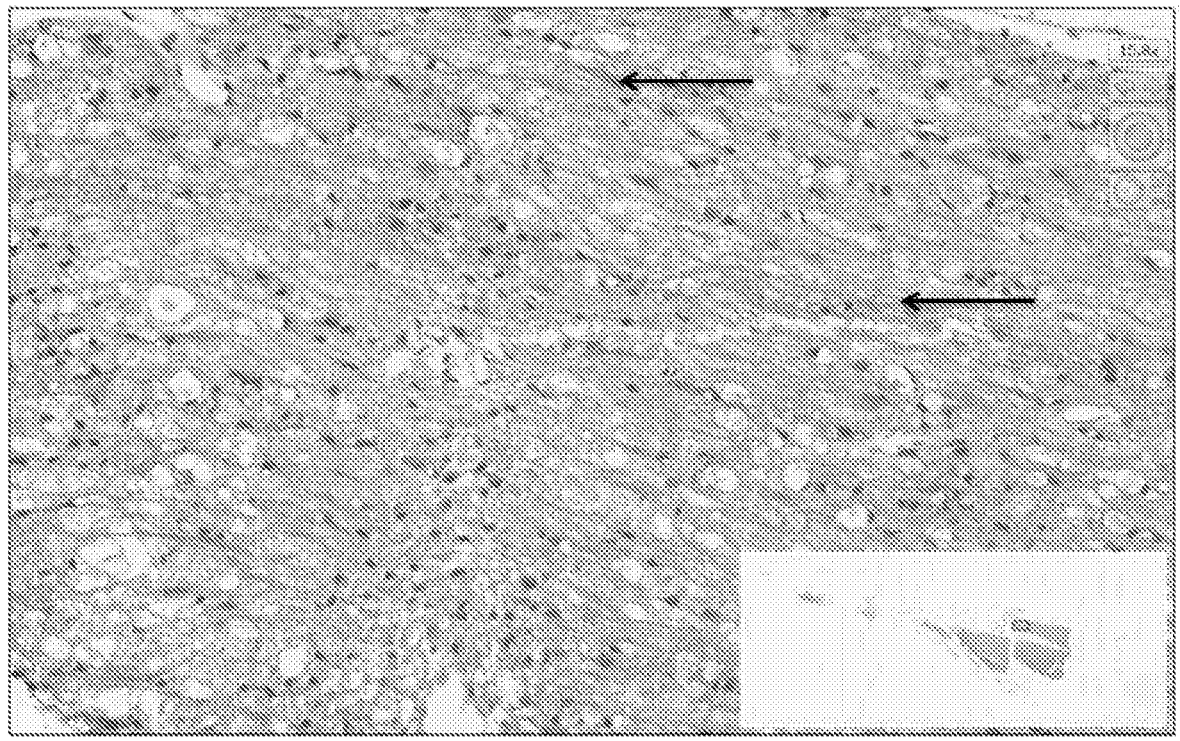

FIG. 33 shows a calpain specimen Control; L. 15× Objective: Grade 1. Note the minimal presence of intra-/extra cellular staining (red) within damaged cord (arrows).

Figure 34:
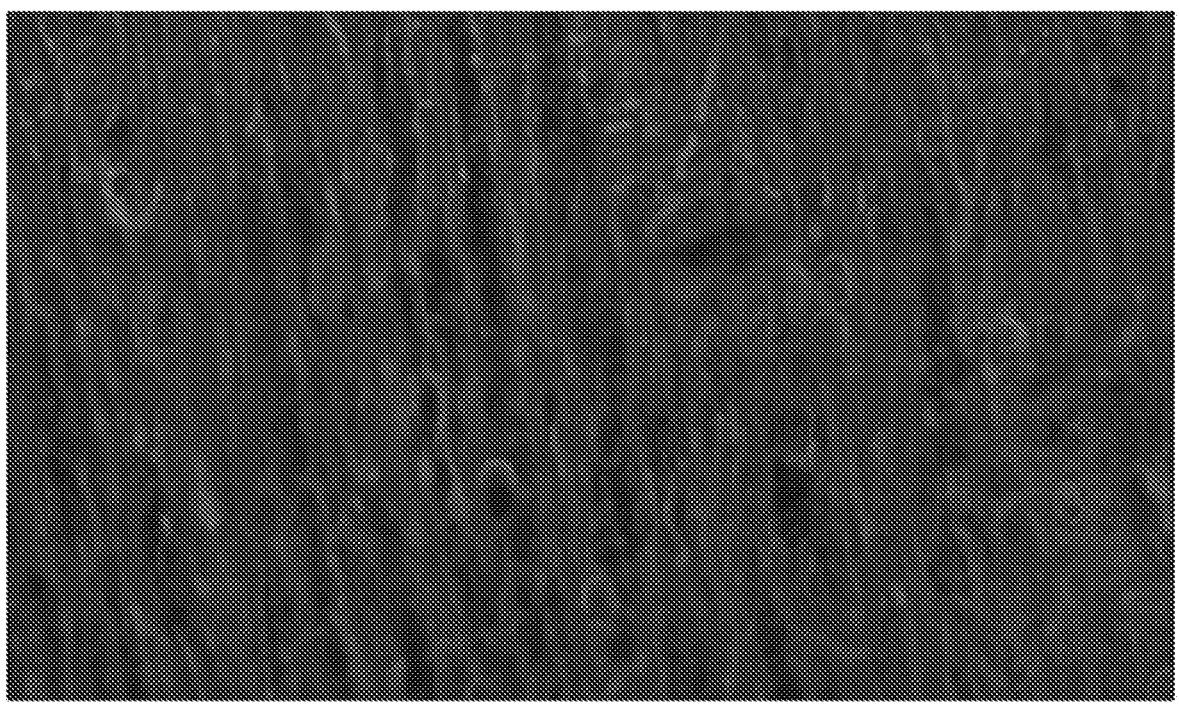

FIG. 34 shows a glial fibrillary acidic protein/neurofilament-200 (GFAP/NF-200) specimen Baseline; L1. 60× Objective: Grade 0. Note the diffuse and fine reticular GFAP-positive structural network (red) and variably-sized, linear, NF-200-positive tubular network (green). Note—nuclei stain blue.

Figure 35:
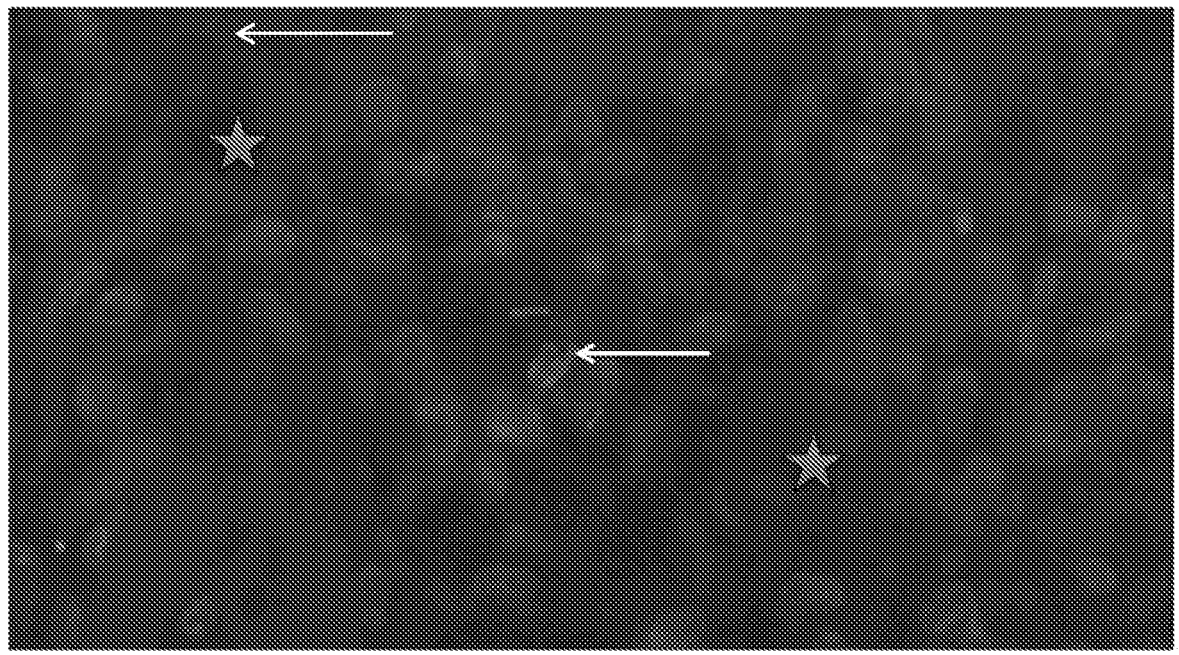

FIG. 35 shows a GFAP/NF-200 specimen xpi-PANi-E-C-A; L1. 60× Objective: Grade 4. Note the total loss of the fine reticular GFAP-positive structural network with replacement by a diffuse and homogeneous GFAP-positive protein deposit (stars). Residual and scant NF-200-positive material is represented by condensed globular deposits (arrow).

Figure 36:
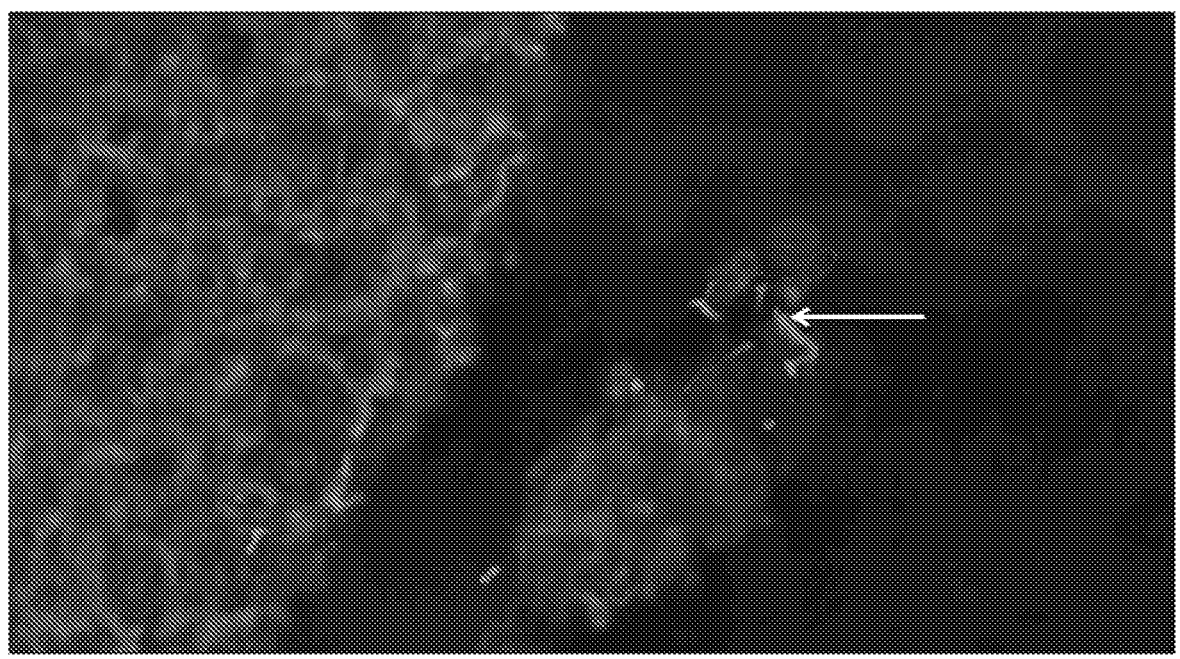

FIG. 36 shows a GFAP/NF-200 specimen xpi-PANi-E-C-A; L1. 60× Objective: Grade 4; marginal zone. Note the marginal rounding and thickening of GFAP-positive protein at the margin of the reparative lesion (arrow).

DETAILED DESCRIPTION

Specific, but non-limiting embodiments of the disclosure will now be described. The content of the Summary above, is repeated hereunder by way of reference thereto, and to avoid lengthy repetition.

Generally, and in accordance with a first aspect of this disclosure there is provided a pharmaceutical composition comprising polyacrylonitrile (PANi) and/or elastin (E) and/or collagen (C), together forming a polyacrylonitrile (PANi) and/or elastin (E) and/or collagen (C) polymer network in the form of PANi-E and/or PANi-C and/or PANi-E-C. Typically, the polyacrylonitrile (PANi) is crosslinked via a crosslinking agent such that the PANi-E and/or PANi-C and/or PANi-E-C may form a crosslinked, porous, semi-interpenetrating (or interpenetrating) polymer network (xpi). The crosslinked polyacrylonitrile (PANi) associates and/or bonds and/or connects with the elastin (E) and/or collagen (C) facilitating reorientation of the secondary structure of proteins elastin (E) and collagen (C).

The association and/or bond formation and/or connection between polyacrylonitrile (PANi) and/or elastin (E) and/or collagen (C) may be via covalent and/or non-covalent and/or non-bonding interactions. The covalent interactions may include for example: α-bonds and/or π-bonds. The non-covalent interactions may include for example: ionic, ion-dipole, hydrogen bonding, dipole-dipole, van der Waals, dipole-induced-dipole, London dispersion, π-π interactions, π-stacking, cation-π interactions and anion-π interactions. The non-bonding interactions may arise from the stretching, bending and torsional strain experienced by PANi molecules in close vicinity of proteins elastin (E) and/or collagen (C) and vice versa.

The Applicant unexpectedly and surprisingly found that the reorientation of the secondary structure of proteins elastin (E) within PANi-E resulted in the concentration dependent secondary structure of protein elastin (E) being such that the concentration of random coils>β-sheets>α-helix>β-turns.

The Applicant unexpectedly and surprisingly found that the reorientation of the secondary structure of proteins collagen (C) within PANi-C resulted in the concentration dependent secondary structure of protein collagen (C) being such that the concentration of α-helix>random coils>β-turns>β-sheets.

The Applicant unexpectedly and surprisingly found that the reorientation of the secondary structure of proteins elastin (E) and collagen (C) within PANi-E-C resulted in the concentration dependent secondary structure of proteins elastin (E) and collagen (C) being such that the concentration of random coils>α-helix>β-sheets>β-turns.

The concentration dependent secondary structure of elastin (E) alone, prior to reorientation, is such that the concentration of β-sheets>random coils>α-helix>β-turns. The concentration dependent secondary structure of collagen (C) alone, prior to reorientation, is such that the concentration of β-sheets>α-helix>random coils>β-turns. The reorientation of elastin (E) and/or collagen (C) provides for the reorientated secondary structure of proteins elastin (E) and/or collagen (C) to approximate, or to be in, their native or natural form as naturally found in the extra cellular matrix (ECM) of a human or animal, providing spinomimetic properties. The reorientation is further facilitated by self-assembly.

The pharmaceutical composition includes a network of channels and/or tunnels imparting sponge-like characteristics thereto. The sponge-like pharmaceutical composition is termed a neurosponge. The term "neurosponge" is abbreviated where appropriate to "NS".

When the pharmaceutical composition is in use implanted into a human or animal body at, near, adjacent to, or in connection with, a spinal cord of said human or animal body, the channels and/or tunnels provides a pathway and/or route and/or conduit for nerve tissue and/or axonal growth and/or repair.

The channels and/or tunnels include along their surfaces (their inner surfaces) raised formations or protrusions. The raised formations or protrusions provide an anchoring means for nerve tissue or neuronal tissue, particularly axons, facilitating growth and/or repair. The protrusions inside the channels and/or tunnels facilitate providing a fibrous channeled and/or tunnel polymeric architecture which mimics human or animal spinal cord.

In accordance with a preferred embodiment of the first aspect of this disclosure there is provided a pharmaceutical composition comprising polyacrylonitrile (PANi), elastin (E), and collagen (C). Together the PANi, elastin (E) and collagen (C) forms a polyacrylonitrile (PANi), elastin (E), collagen (C) polymer network (PANi-E-C).

The polyacrylonitrile (PANi) is typically crosslinked via a crosslinking agent to form a crosslinked, porous, interpenetrating polyacrylonitrile (PANi), elastin (E) and collagen (C) polymer network (xpi-PANi-E-C). The crosslinked polyacrylonitrile (PANi) associates and/or bonds and/or connects with the elastin (E) and collagen (C) facilitating reorientation of the secondary structure of proteins elastin (E) and collagen (C). The reorientation is to a secondary structure form that more closely mimics their native or naturally occurring form in the extra cellular matrix (ECM) of a human or animal body.

The association and/or bond formation and/or connection between polyacrylonitrile (PANi) and elastin (E) and collagen (C) may be via covalent and/or non-covalent and/or non-bonding interactions. The covalent interactions may include for example: α-bonds and/or π-bonds. The non-covalent interactions may include for example: ionic, ion-dipole, hydrogen bonding, dipole-dipole, van der Waals, dipole-induced-dipole, London dispersion, π-π interactions, π-stacking, cation-π interactions and anion-n interactions. The non-bonding interactions may arise from the stretching, bending and torsional strain experienced by PANi molecule in close vicinity of elastin (E) and collagen (C) and vice versa. Without being limited to theory, the non-covalent interactions such as hydrogen bonding and non-bonding interactions are the greatest contributors toward effective reorientation of the elastin (E) and collagen (C) secondary protein structure.

A chemical bond may be formed between two atoms or groups of atoms from among crosslinked polyacrylonitrile (PANi), elastin (E), and collagen (C) such that the forces acting between them are such as to lead to the formation of an aggregate with sufficient stability to define the resulting interpenetrating polymer network as an independent molecular species.

The Applicant unexpectedly and surprisingly found that the reorientation of the secondary structure of proteins elastin (E) and collagen (C) within xpi-PANi-E-C-NS resulted in the concentration dependent secondary structure of proteins elastin (E) and collagen (C) being such that the concentration of random coils>α-helix>β-sheets>β-turns. The symbol ">" denotes the term "greater than" throughout this specification.

The concentration dependent secondary structure of elastin (E) alone, prior to forming part of the xpi-PANi-E-C-NS, is such that the concentration of β-sheets>random coils>α-helix>β-turns. The concentration dependent secondary structure of collagen (C) alone, prior to forming part of the xpi-PANi-E-C-NS, is such that the concentration of β-sheets>α-helix>random coils>β-turns. The reorientation of both elastin (E) and collagen (C) provides for the reorientated secondary structure of proteins elastin (E) and collagen (C) to approximate, or to be in, their native or natural form as naturally found in the extra cellular matrix (ECM) of a human or animal. The reorientation is be further facilitated by self-assembly.

The reorientation imparts to the xpi-PANi-E-C pharmaceutical composition/NS unique and/or advantageous chemico-physical properties/mechanico-physical properties, including, but not limited to, providing elasticity and/or mechanical strength and/or deformation energy and/or rigidity and/or stiffness and/or firmness and/or resilience mimicking human or animal spinal cord tissue, and therein providing a spinomimetic pharmaceutical composition.

The Applicant was surprised that the association and/or bond formation and/or connection between chemically neutral polyacrylonitrile (PANi) and elastin (E) and collagen (C), and subsequent reorientation of elastin (E) and collagen (C), would result in xpi-PANi-E-C having spinomimetic properties.

The crosslinking agent is typically methylenebisacrylamide (MBAAm).

The xpi-PANi-E-C pharmaceutical composition is produced as having a network of channels and/or tunnels imparting sponge-like characteristics to the xpi-PANi-E-C. The sponge-like xpi-PANi-E-C may be a neurosponge (NS).

When the xpi-PANi-E-C pharmaceutical composition/NS is in use implanted into a human or animal body at, near, adjacent to, or in connection with, a spinal cord of said human or animal body, the channels and/or tunnels provides a pathway and/or route and/or conduit for nerve tissue and/or axonal growth and/or repair.

The channels and/or tunnels include along their surfaces raised formations or protrusions. The raised formations or protrusions provide an anchoring means for nerve tissue or neuronal tissue, particularly axons, facilitating growth and/or repair. The protrusions inside the channels and/or tunnels facilitate providing a fibrous channeled and/or tunnel polymeric architecture which mimics human or animal spinal cord. Predicting the presence of said channels and/or tunnels and further predicting the presence of the raised formations based on the component chemical compounds of the pharmaceutical composition was not possible.

The second to fifth aspects are repeated herein as per the Summary above.

The general method of producing the PANi-E, PANi-C and/or PANi-E-C pharmaceutical compositions according to the broad first aspect of this disclosure is provided further below in the examples.

In accordance with a preferred embodiment of the sixth aspect of this disclosure there is provided a method of producing the pharmaceutical composition according to the first aspect of this disclosure, the method comprising the following steps:
(i) dissolving elastin (E) and collagen (C) in an acidic aqueous medium to form a first solution;
(ii) adding acrylonitrile to the first solution and mixing to form a second solution, which second solution may be agitated/mixed until homogenous;
(iii) adding a initiator, for example, but not limited to, ammonium persulphate (APS), to the homogenous second solution,
    wherein the initiator initiates free radical polymerization of the acrylonitrile to form an interpenetrating polyacrylonitrile (PANi), elastin (E) and collagen (C) polymer network (iPANi-E-C); and
(iv) adding a crosslinking agent, for example, but not limited to methylenebisacrylamide (MBAAm),
    wherein the crosslinking agent crosslinks the polyacrylonitrile (PANi) to form a crosslinked, porous, interpenetrating polyacrylonitrile (PANi), elastin (E) and collagen (C) polymer network (xpi-PANi-E-C).

Steps (i) to (iv) take place in sequence beginning at Step (i) and ending in Step (iv). Within the sequence, Steps (iii) and (iv) takes place concomitantly.

The method further includes Step (v): adding an accelerant, for example, tetramethylethylenediamine (TEMED), wherein Step (v) takes place after Step (iv).

The acidic aqueous medium of Step (i) is an aqueous acetic acidic medium. Step (i) may include the addition of excess glacial acetic acid to prevent precipitation of elastin (E) and/or collagen (C) from the first solution.

The method further includes Step (vi): pouring the xpi-PANi-E-C into moulds, preferably, polyethylene moulds, and allowing the same to set (wherein further polymerization takes place) forming a porous xpi-PANi-E-C neurosponge. Preferably the xpi-PANi-E-C is allowed to set overnight, further preferably, under room temperature conditions.

The method further includes Step (vii): washing the porous xpi-PANi-E-C-NS, preferably with double distilled water. The method further includes Step (viii): freezing the washed xpi-PANi-E-C-NS between about −80° C. and −60° C., preferably for a time period of between about 8 to 12 hours. The method further includes Step (ix): lyophilizing the xpi-PANi-E-C-NS, preferably at about 25 mmtorr for about 24 hours. The lyophilization process may further contribute to channel and/or tunnel formation and therein may facilitate imparting porosity.

The Applicant unexpectedly and surprisingly found that the xpi-PANi-E-C pharmaceutical composition or neurosponge according to this disclosure provides unique physico-chemical properties allowing for its efficient and successful use in the treatment of spinal cord injury in a human or animal.

For example, several of the challenges highlighted in the prior art are met by the xpi-PANi-E-C pharmaceutical composition/neurosponge. The xpi-PANi-E-C pharmaceutical composition/neurosponge provides a biocompatible and/or biodegradable composition by mimicking human or animal spinal cord therein minimizing inflammation and/or neuronal death.

The xpi-PANi-E-C pharmaceutical composition/neurosponge provides a composition that limits the amount of surgical interventions, as it was seen (see Animal Studies below) that one surgical intervention was sufficient. The xpi-PANi-E-C pharmaceutical composition/neurosponge also allows for preservation of the blood-spinal barrier, facilitates reduction in glial scar tissue formation, promotes and facilitates adhesion of, and proliferation of, neuronal tissue, and mimics human or animal spinal cord. The xpi-PANi-E-C pharmaceutical composition/neurosponge provides an almost linear degradation profile over the 4-weeks period ($R^2$=0.9802) with ≈50% matrix degradation at day 28 which is particularly advantageous for use as a surgical implant in spinal cord injury treatment protocols.

The Applicant unexpectedly and surprisingly found that the reorientation of the secondary structure of proteins elastin (E) and collagen (C) within xpi-PANi-E-C-NS resulted in the concentration dependent secondary structure of proteins elastin (E) and collagen (C) being such that the concentration of random coils>α-helix>β-sheets>β-turns.

The concentration dependent secondary structure of elastin (E) alone, prior to forming part of the xpi-PANi-E-C, is such that the concentration of β-sheets>random coils>α-helix>β-turns. The concentration dependent secondary structure of collagen (C) alone, prior to forming part of the xpi-PANi-E-C-NS, is such that the concentration of β-sheets>α-helix>random coils>β-turns.

The reorientation of both elastin (E) and collagen (C) provides for the reorientated secondary structure of proteins elastin (E) and collagen (C) to be in their native or natural form as naturally found in the extra cellular matrix (ECM) of a human or animal. The reorientation imparts to the xpi-PANi-E-C unique and/or advantageous chemico-physical properties, including, but not limited to, providing elasticity and/or mechanical strength and/or deformation energy and/or rigidity and/or stiffness and/or firmness and/or resilience mimicking human or animal spinal cord tissue, and therein providing a spinomimetic pharmaceutical composition.

Without being limited to theory, the method of producing the pharmaceutical composition provides for and/or facilitates the reorientation of elastin (E) and collagen (C), and further provides for and/or facilitates formation of channels/tunnels and protrusions, all important aspects that contribute to providing advantages when in use.

The pharmaceutical composition of this disclosure at least ameliorates some of the disadvantages of the prior art.

While the disclosure has been described in detail with respect to specific embodiment and/or examples (see further below), it will be appreciated that those skilled in the art, upon attaining an understanding of the foregoing may readily conceive of alterations to, variations of and equivalents to these embodiments. Accordingly, the scope of the present invention should be assessed as that of the appended claims, which claims are appended hereto.

EXAMPLES—PREPARATION & CHARACTERIZATION

Non-limiting examples of the disclosure are provided hereunder. The content of the Summary above, is repeated hereunder by way of reference thereto, and to avoid lengthy repetition.

Materials and Methods
Materials

Acrylamide (AAm) and acrylonitrile (ANi) monomers, potassium persulphate (KPS), ammonium persulphate (APS), methylene bisacrylamide (MBAAm), tetramethylethylenediamine (TEMED), collagen Type IV. Elastin peptide was obtained from Elastin Products Company, Inc., Owensville, MO, USA. The bioactives, curcumin and dexamethasone disodium salt, was obtained from Sigma-Aldrich, St. Louise, MO, USA. All other reagents used were of analytical grade and were used as received.

Preparation of Xpi-PANi-E-C Pharmaceutical Composition/Neurosponge

The crosslinked, interpenetrating polyacrylonitrile (PANi), elastin (E) and collagen (C) polymer network (xpi-PANi-E-C) pharmaceutical composition was obtained by simultaneous crosslinking and polymerization of polyacrylonitrile and forming an interpenetrating polymer network with, and in the presence of, collagen and/or elastin in an aqueous acetic acid medium (Table 1). The xpi-PANi-E-C pharmaceutical composition is also termed herein xpi-PANi-E-C spinomimetic neurosponge or xpi-PANi-E-C neurosponge. The term "neurosponge" is abbreviated where appropriate to "NS". In the accompanying figures that relate to the experimental work herein labels for xpi-PANi-E-C may be shown as PANi-EC.

Briefly, collagen and elastin were dissolved in specified quantities in an aqueous acetic acidic medium and to it acrylonitrile was added. The solution was then observed for precipitation of the peptide content, if any. In the case of peptide precipitation, excess glacial acetic acid was added to the above mixture to maintain the required pH for peptide solubility. After a homogenous mixture was obtained, an initiator such as ammonium persulphate (APS), a crosslinker such as methylenebisacrylamide (MBAAm) and an accelerant such as tetramethylethylenediamine (TEMED) were added in sequence. The above mixture was then poured into polyethylene syringe moulds and allowed to polymerize overnight under room temperature conditions. The xpi-PANi-E-C neurosponge matrices so obtained were washed with excess double distilled water and were frozen overnight at −80° C. This was followed by lyophilisation (25 mtorr for 24 hours) to remove constituent water and acetic acid and a three dimensional (3D) neurosponge matrix was obtained.

The Applicant used the same abovementioned experimental protocol to prepare the following by omitting either elastin (E), collagen (C) or both: a PANi neurosponge; a PANi-E neurosponge; and a PANi-C neurosponge. The PANi-E-NS, PANi-C-NS were as such also crosslinked and provide an interpenetrating or semi-interpenetrating polymer network. PANi-E-NS and PANi-C-NS also provide chemico-physical properties for use in the treatment of spinal cord injury, and form part of the broad first aspect of this disclosure. The Applicant also utilized the PANi PANi-E, and PANi-C neurosponges for comparative purposes, as more fully described and/or exemplified further below. The term "neurosponge" is abbreviated where appropriate to "NS".

TABLE 1

Formulation constituents of the xpi-PANi-E-C pharmaceutical composition and comparative neurosponges (NS).

| Constituent | PANi-NS | PANi-E-NS | PANi-C-NS | xpi-PANi-EC-NS |
|---|---|---|---|---|
| Acetic acid (3% $^v/_v$) | 8 mL | — | — | — |
| Collagen (0.5% $^w/_v$) | — | — | 8 mL | 8 mL |
| Elastin powder | — | 1 g | — | 1 g |
| Acrylonitrile | 1 mL | 1 mL | 1 mL | 1 mL |
| Acetic acid (glacial) | — | 0.7 mL | 0.7 mL | 0.7 mL |
| Methylene bisacrylamide (MBAAm) | 200 mg | 200 mg | 200 mg | 200 mg |

TABLE 1-continued

Formulation constituents of the xpi-PANi-E-C pharmaceutical composition and comparative neurosponges (NS).

| Constituent | PANi-NS | PANi-E-NS | PANi-C-NS | xpi-PANi-EC-NS |
|---|---|---|---|---|
| Ammonium persulphate (APS) | 50 mg | 50 mg | 50 mg | 50 mg |
| Tetramethylethylenediamine (TEMED) | 0.1 mL | 0.1 mL | 0.1 mL | 0.1 mL |

Collectively, the neurosponges that were produced (PANi neurosponge; PANi-E neurosponge; PANi-C neurosponge; and xpi-PANi-E-C) are referred to as scaffold matrices below.

The comparative experimental protocols highlight surprising unique and advantageous chemico-physical properties of xpi-PANi-E-C-NS which could not have been predicted upon an analysis of the chemico-physical properties of PANi-NS, PANi-E-NS, PANi-C-NS nor from an analysis of the chemico-physical properties of their component chemical compounds such as polyacrylonitrile (PANi), elastin (E), and collagen (E).

The xpi-PANi-E-C-NS provided unique and/or advantageous chemico-physical properties, including, but not limited to, providing elasticity and/or mechanical strength and/or deformation energy and/or rigidity and/or stiffness and/or firmness and/or resilience mimicking human or animal spinal cord tissue, and therein providing a spinomimetic pharmaceutical composition.

When considering xpi-PANi-E-C, the presence of crosslinked polyacrylonitrile (xPANi) and its consequent association and/or bond formation and/or connection with the elastin (E) and collagen (C) facilitates reorientation of the secondary structure of proteins elastin (E) and collagen (C). This aforesaid reorientation provides for the xpi-PANi-E-C pharmaceutical composition/NS that includes chemico-physical properties mimicking human or animal spinal cord i.e. it is spinomimetic. Without the reorientation of the secondary structure of proteins elastin (E) and collagen (C), the pharmaceutical composition would not have chemico-physical properties mimicking human or animal spinal cord i.e. it would not be spinomimetic. The reorientation is such that the reorientated secondary structure of proteins elastin (E) and collagen (C) approximates, to a greater degree, native and/or naturally occurring elastin (E) and/or collagen (C) when compared to commercially available equivalents of elastin (E) and/or collagen (C).

The Applicant unexpectedly and surprisingly found that the reorientation of the secondary structure of proteins elastin (E) and collagen (C) within xpi-PANi-E-C resulted in the concentration dependent secondary structure of proteins elastin (E) and collagen (C) being such that the concentration of random coils>α-helix>β-sheets>β-turns.

The concentration dependent secondary structure of elastin (E) alone, prior to forming part of the xpi-PANi-E-C, is such that the concentration of β-sheets>random coils>α-helix>β-turns. The concentration dependent secondary structure of collagen (C) alone, prior to forming part of the xpi-PANi-E-C, is such that the concentration of β-sheets>α-helix>random coils>β-turns.

Morphological Analysis and Image Processing

For morphological analysis, the scaffold matrices (including the PANi neurosponge, PANi-E neurosponge, PANi-C neurosponge, and the xpi-PANi-E-C neurosponge according to this disclosure) were sputter coated with carbon and/or chromium and photomicrographs was captured at various magnifications using FEI Quanta 200 ESEM or FEI Nova Nanolab 600 SEM (FEI, Hillsboro, Oregon, USA). The micrographs so obtained were extensively analyzed and quantified using Diameter) and ND plugins created for ImageJ and FIJI (image processing software). Diameter) plugin is a "nanofiber diameter measurement tool" and was created "using existing algorithms for centerline determination, Euclidean distance transforms and a novel pixel transformation technique" (Hotaling et al., 2015). A unique algorithm combining the segmentation tool of Diameter) and the Image Threshold Adjustment function of ImageJ was developed for the processing of SEM micrographs. The processed images were then analysed for pore area and fractional roundity. Some SEM images were quantitatively processed on Mathematica™ 8.0 (Wolfram Research, Champaign, IL, USA) using a sequential procedure of blurring, colour-quantizing and generating an image histogram. Initially, the area of interest was restricted to image content of the scaffold.

Porositometric Analysis of the PANi Neurosponge, PANi-E Neurosponge, PANi-C Neurosponge, and the Xpi-PANi-E-C According to this Disclosure Porositometric analysis was performed on the neurosponges using a porosity analyser (Micromeritics ASAP 2020, Norcross, GA, USA). The neurosponge (scaffold matrix) samples were cut with a razor blade and accurately weighed before adding to the samples tube. Given the high and multilevel porosity of the scaffolds, the scaffolds were degassed for 22 hours at 40 C. After degassing, the sample was transferred to the analysis port and a data report incorporating surface area, pore volume, and pore size related to adsorption and desorption isotherms. Both BJH and BET computations were evaluated. The linear isotherm plots obtained were compared with the guidelines as prescribed by the IUPAC (Sing et al., 1985).

Polymeric Structural Variation Analysis

Attenuated Total Reflectance-Fourier Transform Infra-Red (ATR-FTIR) analysis was performed on the component chemical compounds and the final scaffolds including the PANi neurosponge, PANi-E neurosponge, PANi-C neurosponge, and the xpi-PANi-E-C neurosponge according to this disclosure to evaluate, ascertain and compare structural transformations. ATR-FTIR spectra were recorded on a Perkin Elmer Spectrum 2000 FTIR spectrometer with a MIRTGS detector (PerkinElmer Spectrum 100, Llantrisant, Wales, UK), using an ATR-FTIR cell and a diamond crystal internal reflection element. Samples were analyzed at a wavenumber range of 650-4000 $cm^1$ with a resolution of 4 $cm^{-1}$ and 64 scans per spectrum.

Exothermic and Endothermic Mapping of the Grafted Polymers

Comparative differential scanning calorimetry (DSC) analyses were performed on the native polymers, and the final scaffolds/neurosponges using a Mettler Toledo, DSC1, STAR$^e$ System (Schwerzenback, Switzerland) at a heating rate of 5-10° C./min from −10 to 325° C. under a constant flow of $N_2$ gas. Accurately weighed samples (5-10 mg±0.1 mg) were placed into a covered aluminium sample holder with a central pin hole. Indium metal (99.99%) was used to calibrate the DSC modulus in relation to temperature and enthalpy. An empty sample holder was used as reference and experimental runs were performed by heating the samples from 10° C. up to 125° C. with a constant isotherm for 15 min. New samples were re-weighed and heated from 10° C. up to 250° C. DSC thermograms were subsequently compared for transitions in thermal events.

Figure 1:
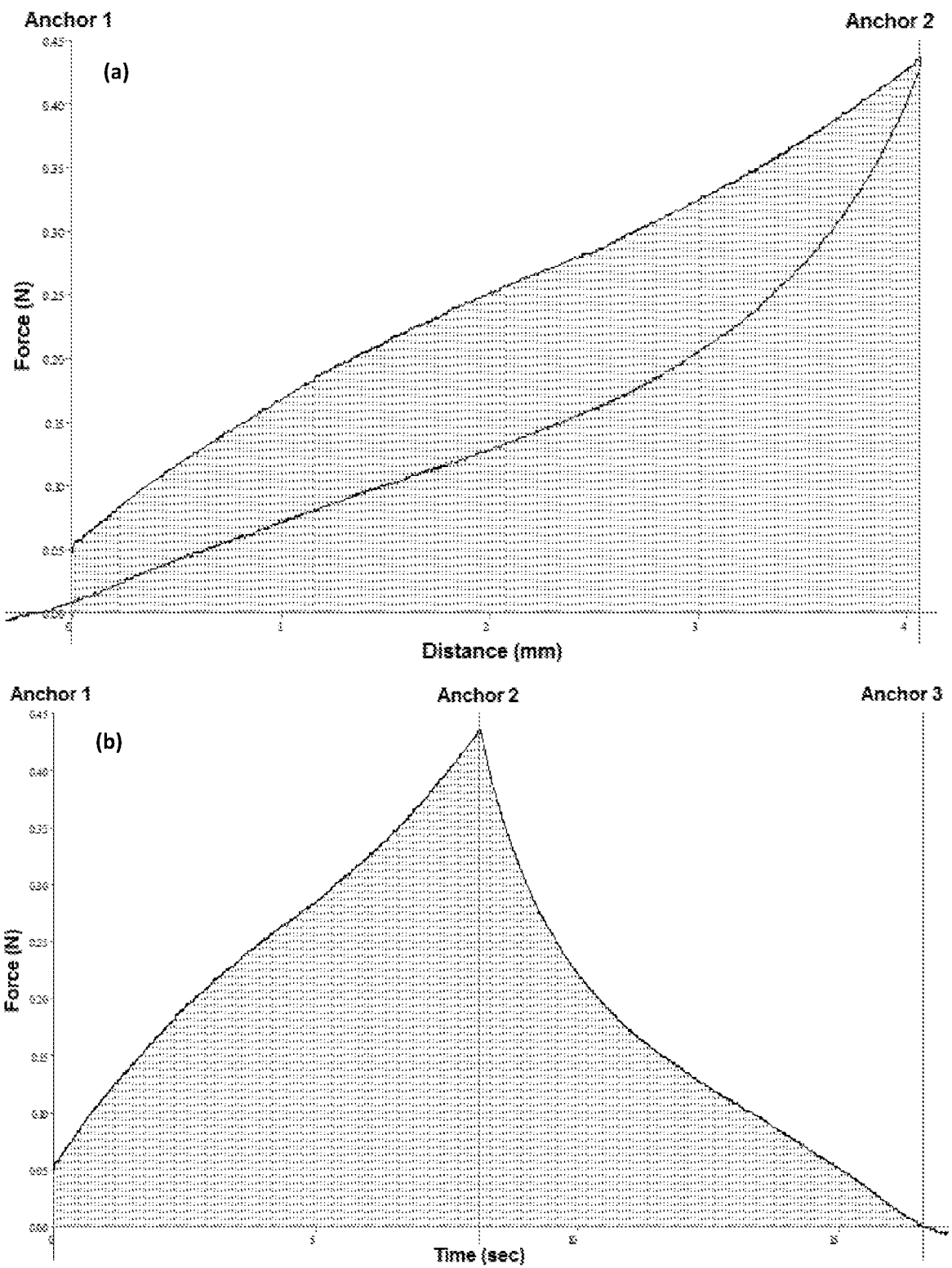

Physico-Mechanical Characterization of the Neurosponges Including the PANi Neurosponge, PANi-E Neurosponge, PANi-C Neurosponge, and the Xpi-PANi-E-C Neurosponge According to this Disclosure Textural Macroanalysis The micromechanical properties of the scaffold matrices may directly influence the ability of the axons to regenerate, proliferate and penetrate within the scaffold matrix. Textural profile analysis was therefore conducted at a micro-scale employing a Texture Analyzer (TA.XTplus Stable Microsystems, Surrey, UK) fitted with a 5 kg load cell. The scaffold matrices were cut into cylinders using a scalpel (10 mm diameter; 10 mm length) and were compressed under various strain values between 10 and 50%. The scaffold matrices were placed on an aluminium stage and were compressed using a flat probe. Serial Force–Time/Distance profiles were generated for various formulations using the parameters detailed in Table 2. Mechanical computations with respect to maximum load, deformation energy, rigidity gradient and % matrix resilience were carried out as displayed in FIG. 1.

TABLE 2

Textural parameter settings employed for physico-mechanical property analysis of the PANi neurosponge, PANi-E neurosponge, PANi-C neurosponge, and the xpi-PANi-E-C neurosponge according to this disclosure.

| | Settings | |
|---|---|---|
| Test parameters | Matrix deformation | Matrix resilience |
| Pre-test speed | 1 mm/sec | 1 mm/sec |
| Test speed | 1 mm/sec | 0.5 mm/sec |
| Post-test speed | 5 mm/sec | 0.5 mm/sec |
| Compressive strain (%) | 10, 15, 20, and 25 | 10, 15, 20, and 25 |
| Sensitivity of trigger force | 0.04903N | 0.04903N |

Xpi-PANi-EC-NS: Spinomimetic, Interpenetrating, Polymer-Peptide, Neurotunnels for Complete Functional Regeneration after Acute Spinal Cord Injury Molecular self-assembly, or simply self-assembly, can be defined as the spontaneous organization of individual entities such as molecules under thermodynamic equilibrium conditions into coherent, well-defined and stable arrangements without human interventions (Zhang, 2002). This self-assembly process mimics several naturally occurring multifunctional macromolecular assemblies such as haemoglobin, polymerases, ATP synthase, membrane channels, the spliceosome, proteosome and ribosome. These assemblies are primarily mediated by weak, non-covalent interactions at macroscopic and microscopic scales or even at nanoscale. The molecular building blocks for self-assembly are engineered and designed to undergo stepwise congregation through the formation of hydrogen bonds, electrostatic interactions (ionic bonds), hydrophobic interactions, van der Waals interactions and π-stacking (Zhang, 2002; Zhang, 2003). The collective strength of these weak interactions forms the basis for the production of very stable supramolecular architectures and bio-inspired nanomaterials with chemical complementarity and structural compatibility (Zhang, 2002). The understanding of such bio-related macromolecular assemblies along with progress in the design and characterization of such self-organization principles in molecular engineering lead to the fabrication of molecular assembling systems based on peptides (including peptide amphiphiles) and/or proteins (Hogashi and Koga, 2008). Peptides and proteins display the inherent ability to self-organize/self-assemble/self-fabricate/self-associate/self-contain hierarchically and precisely into well-defined two- and/or three-dimensional structures. These structures display a high level of regularity which can be developed and controlled to be employed in drug delivery and tissue engineering (Zhang, 2002; Zhang, 2003; Ulijn and Smith, 2008). It is not possible to accurately predict properties of supramolecular architectures when analysing chemical components making up said supramolecular architecture.

Self-assembling peptide (SAP) systems involve synthetic scaffolds capable of presenting multiple cell-interactive components in spatially resolved networks via supramolecular self-assembly. This self-assembly usually results from fibril-forming peptides peptides, peptidomimetics, and peptide derivatives. Self-assembled materials provide several advantages in form of multifunctionality, multivalency, synthetic definition, molecular specificity, and control over the nanoscale positioning of ligands and other biomolecular features. These peptides such as short fibrillizing peptides, β-hairpins, peptide-amphiphiles and peptide derivatives, self-assemble in stimuli-containing environments to form networks of β-sheet-rich nanofibers which further merge to form supramolecular architectures, macroscopically resulting in hydrogels. SAPs are also capable of displaying functional amino acid sequences or chemical groups on the surface of their self-assembled fibers and these peptides can also be conjugated to display precise combinations of different ligands.

Figure 2:
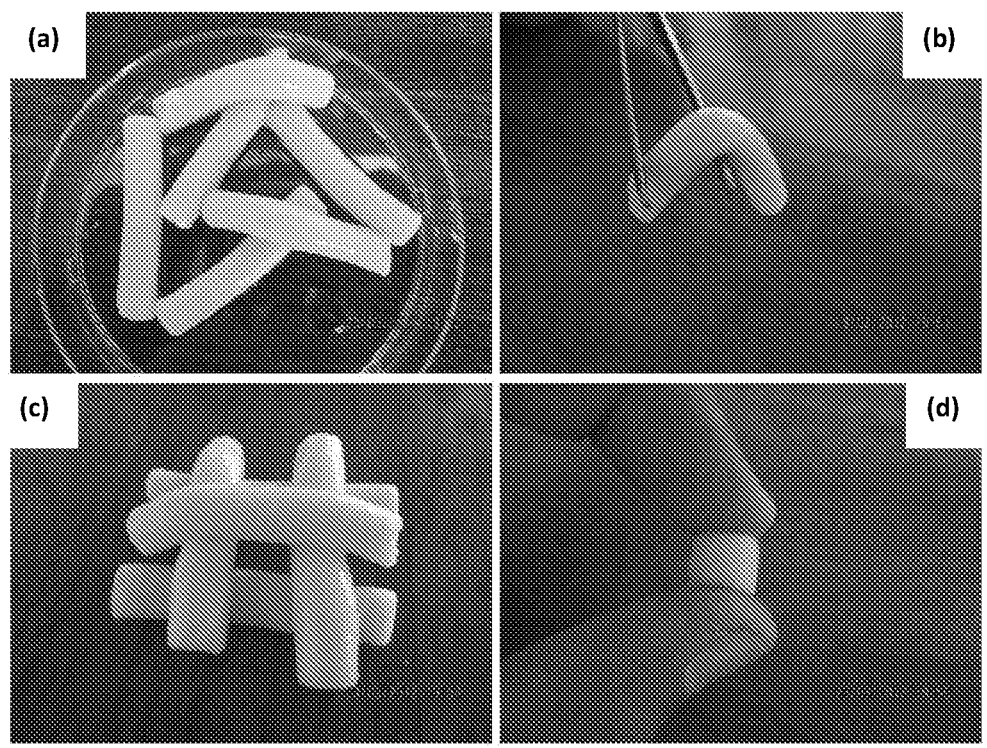
FIG. 2 shows photographs (a) to (d) displaying the easy handling, weight bearing ability, and flexibility of the hydrated xpi-PANi-E-C neurosponge according to this disclosure.

The PANi neurosponge, the PANi-E neurosponge, the PANi-C neurosponge, and the xpi-PANi-E-C neurosponge according to this disclosure and described herein were successfully synthesized and fabricated. xpi-PANi-E-C neurosponge is shown in FIG. 2. FIG. 2 shows photographs displaying the easy handling, weight bearing ability, and flexibility of the hydrated xpi-PANi-E-C-NS. Inter cilia, these chemico-physical properties allow for ready manipulation by a surgeon when in use, and mimics human or animal spinal cord.

The PANi-E neurosponge, the PANi-C neurosponge and the xpi-PANi-C-E neurosponge so formed can be described as a semi-interpenetrating polymer network or an interpenetrating polymer network wherein the crosslinked polyacrylonitrile polymer was interpenetrated by the extracellular matrix components (collagen and elastin) and vice versa. Without being limited to theory, Table 3 provides an indication of the specialized functions provided by the various components into the final tripolymeric xpi-PANi-EC scaffold/NS.

TABLE 3

Chemical components and their specific function(s)

| Component | Function(s) |
|---|---|
| Polyacrylonitrile | Reconstruction of highly functional and complex neuronal networks; provides low density, high strength and modulus of elasticity |
| Collagen | Component of extracellular neuronal matrix |
| Elastin | Component of extracellular neuronal matrix |
| xpi-PANi-E-C | Interpenetrating polymer network scaffold morphologically, physicochemically, and physicomechanically similar to neuronal tissue |

Figure 3:
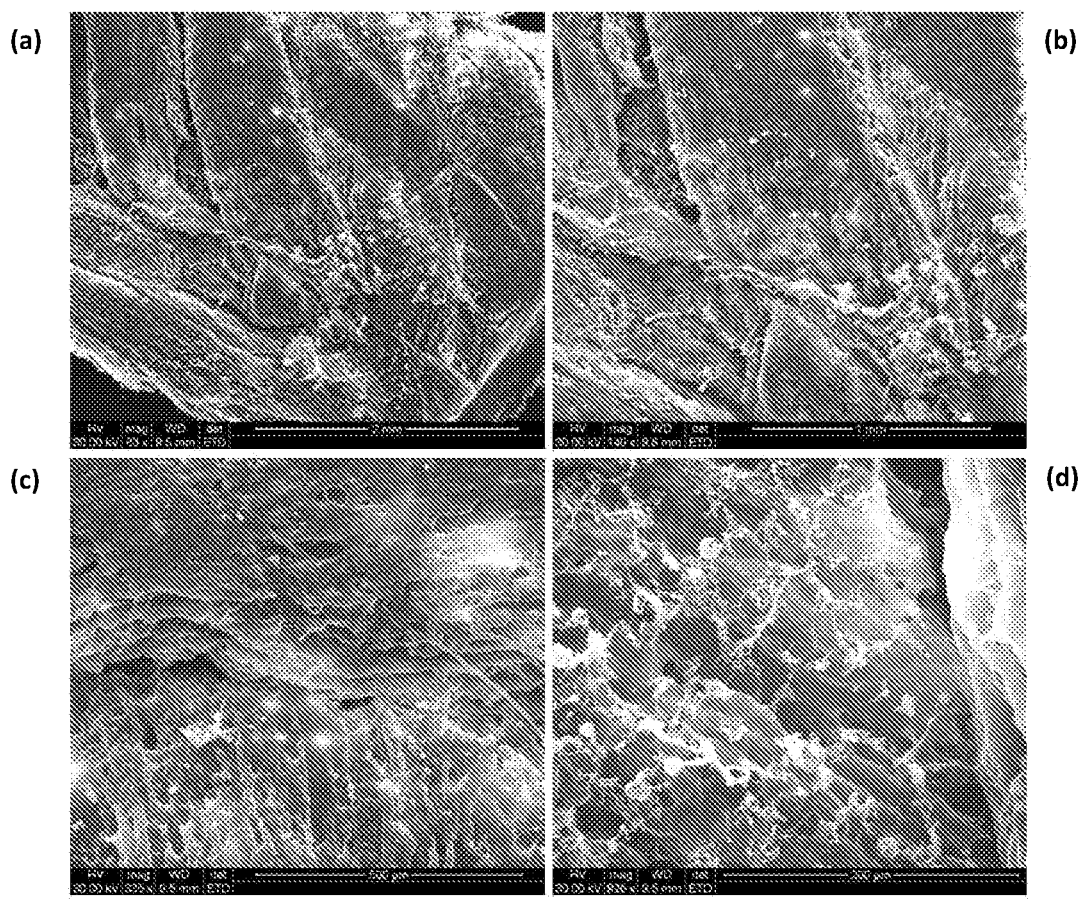
FIG. 3 shows scanning electron micrographs (a) to (d) of lyophilized rat spinal cord.
Figure 4:
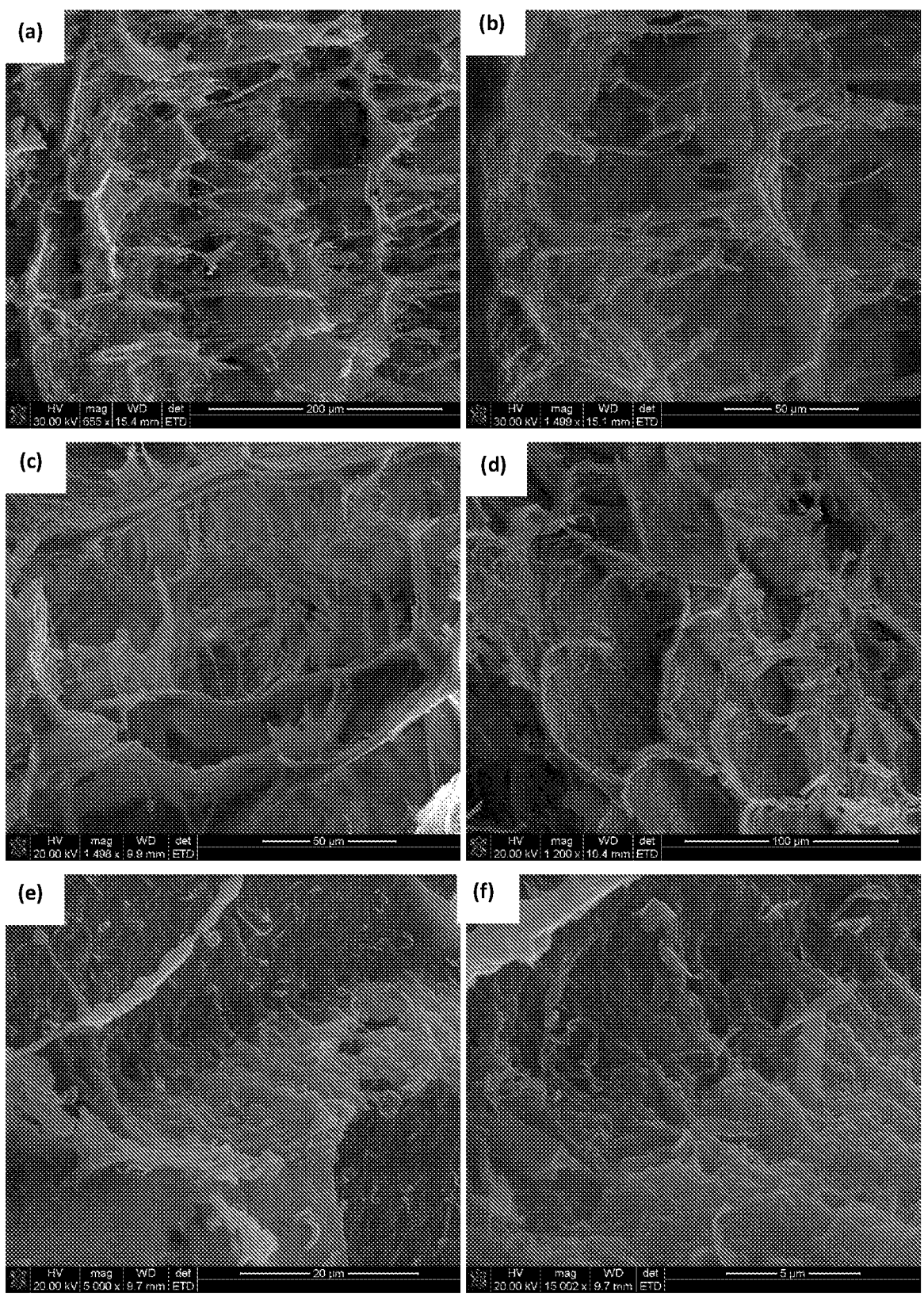
FIG. 4 shows scanning electron micrographs (a) to (f) showing the surface of the spinomimetic architecture of the xpi-PANi-E-C neurosponge according to this disclosure.
Figure 5:
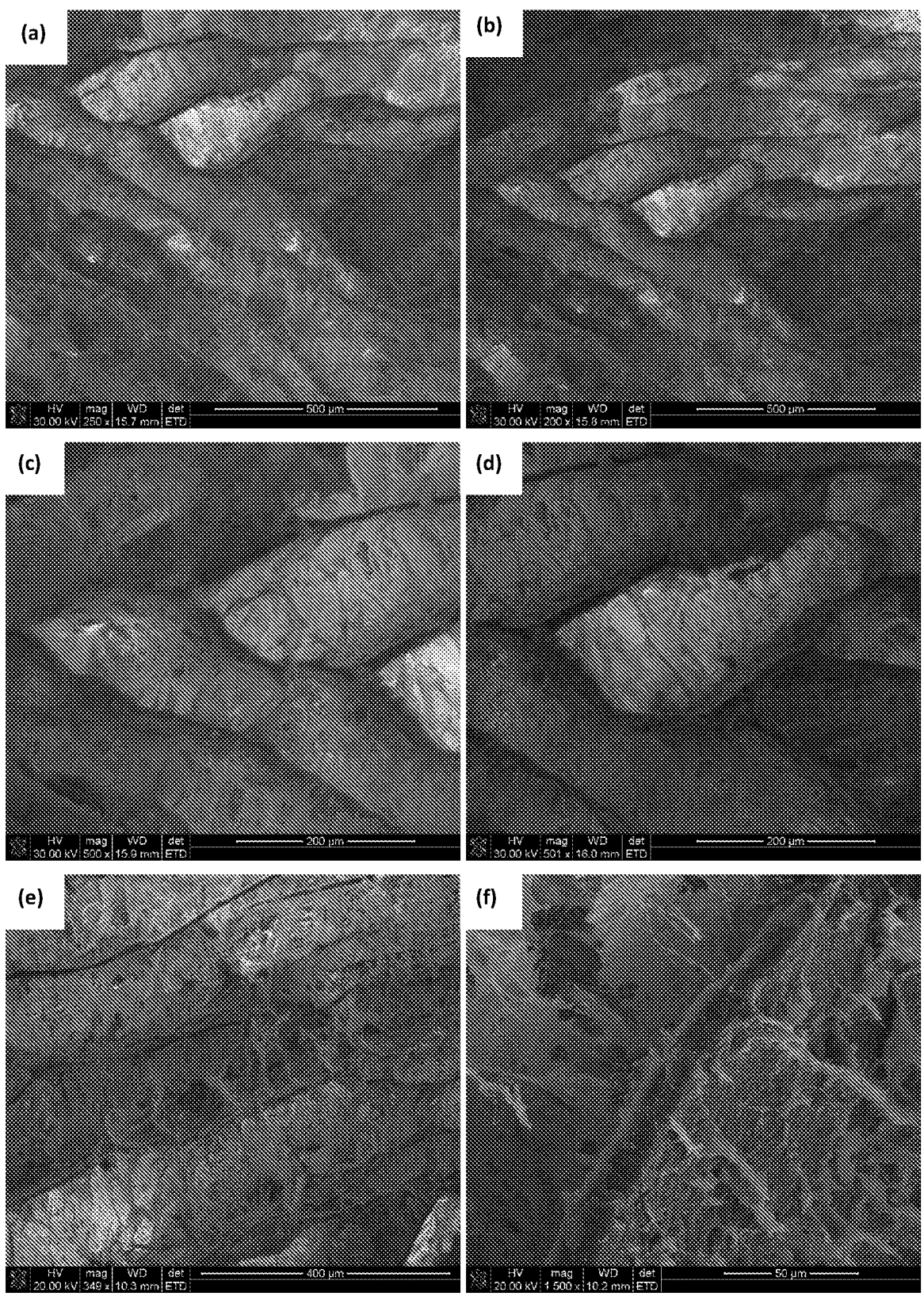
FIG. 5 shows scanning electron micrographs (a) to (f) showing channels or tunnels (the so-called "neurotunnels") within the spinomimetic architecture of the xpi-PANi-E-C neurosponge.
Figure 6:
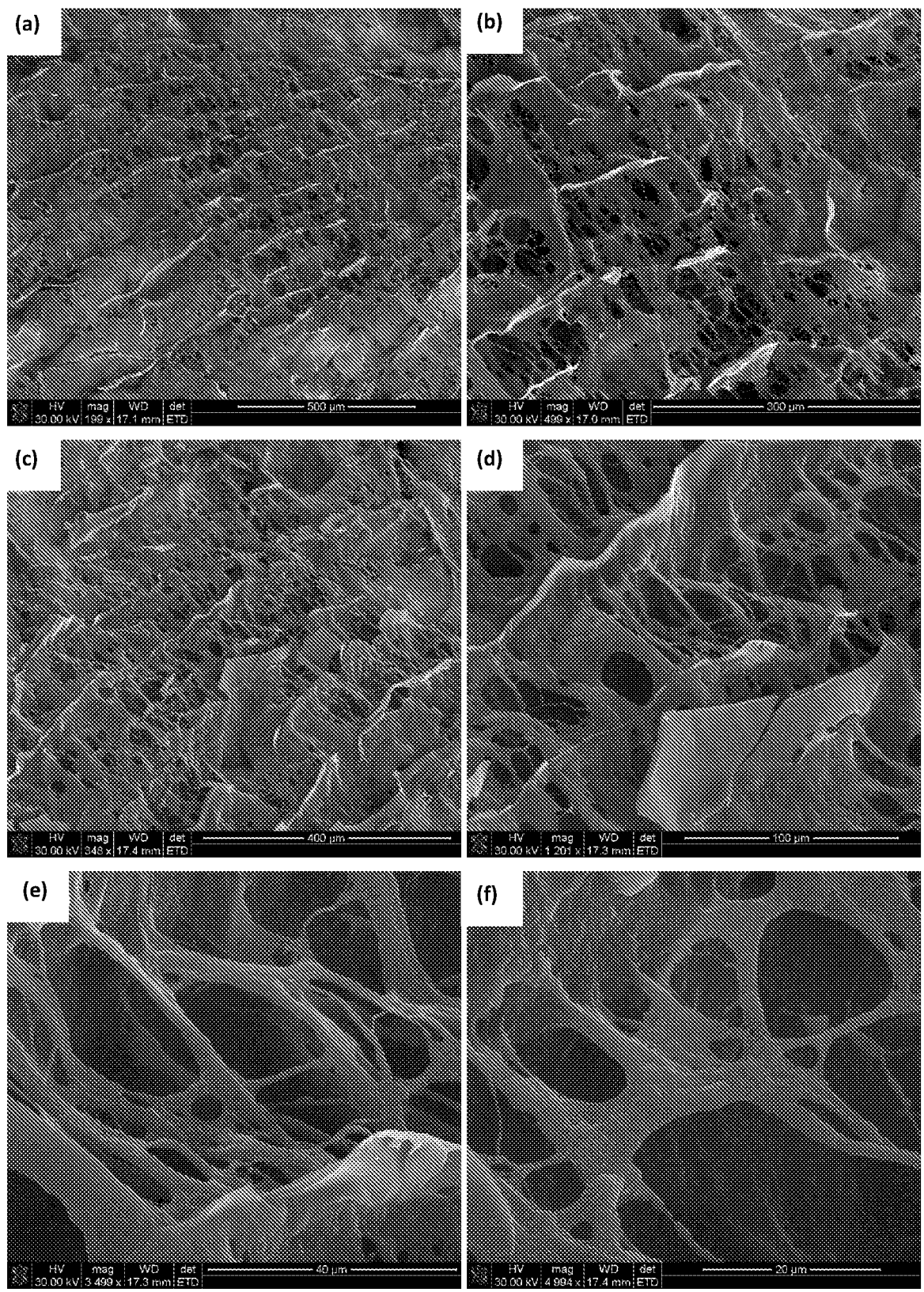
FIG. 6 shows scanning electron micrographs (a) to (f) showing the fibrous nature of the spinomimetic architecture of the xpi-PANi-E-C neurosponge.
Figure 7:
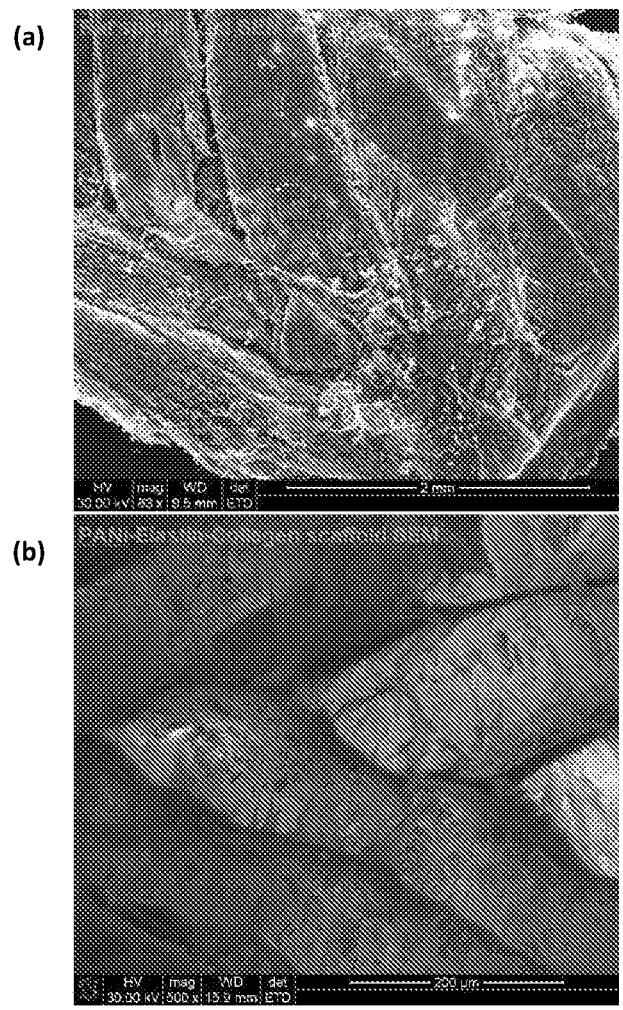
FIG. 7 shows scanning electron micrographs comparing and confirming the spinomimetic architecture of the xpi-PANi-E-C neurosponge, (a) shows rat spinal cord and (b) shows the xpi-PANi-E-C neurosponge.

Morphological Analysis of the PANi Neurosponge, the PANi-E Neurosponge, the PANi-C Neurosponge and the Xpi-PANi-C-E Neurosponge The scanning electron micrographs of the native rat spinal cord displayed a fibrous structure with unidirectional macroscopic fibers and grooves (FIG. 3). The corresponding scanning electron micrograph (SEM) images of xpi-PANi-E-C scaffold demonstrated a polymer matrix comprising of fibro-porous and poro-fibrous architecture (FIG. 4). Furthermore, the porous architecture was comprised of continuous longitudinal channels in the form of polymer tunnels which are hereby referred to as "neurotunnels". These polymer tunnels further diverged and/or converged into multidirectional and/or unidirectional polymer tunnel network (FIG. 5) capable of enhancing the neuronal growth and proliferation. The surface architecture of the scaffold depicted multi-laned longitudinal grooves lined with fibrous matrix (FIG. 6). FIG. 7 compares and confirms the spinomimetic nature of xpi-PANi-E-C via the formation of longitudinal fibrous tunnels.

Therefore, xpi-PANi-E-C can provide an artificial neuronal extracellular matrix conducive to growth of neuronal tissue and axons. The fibers present in these neurotunnels can provide axonal anchoring points while the rough surface providing conducive environment for axonal adhesion and neuronal movement. The tunnels were demarcated with thick PANi walls (15 μm) and were filled with self-assembled peptide fibrous structure with varied diameters ranging from nano- (500 nm) to micro- (10 um) thickness. The fibres were embedded into the PANi architecture (pore walls) forming a web-like network connecting the walls within the longitudinal tunnels. The thick fibers can be attributed to elastin fibers while the thin fibers representing collagen fibrils (Daamen et al., 2003).

However, in addition to fibers; short, thin and wide ribbon-like raised formations or outcrops protruding out from the scaffold wall were observed (further enhancing the roughness of the scaffold wall) which, without being limited to theory, can be attributed to PANi. In conclusion, the formation of a rope bridge-like architecture was observed within the "neurotunnels" wherein the elastin fibers formed the main chains while the collagen fibrils formed the short decks of the bridge. Each of the components complement the other's function and together provide the required strength and functionality.

Porositometric Analysis of the Spinomimetic Scaffolds

Figure 8:
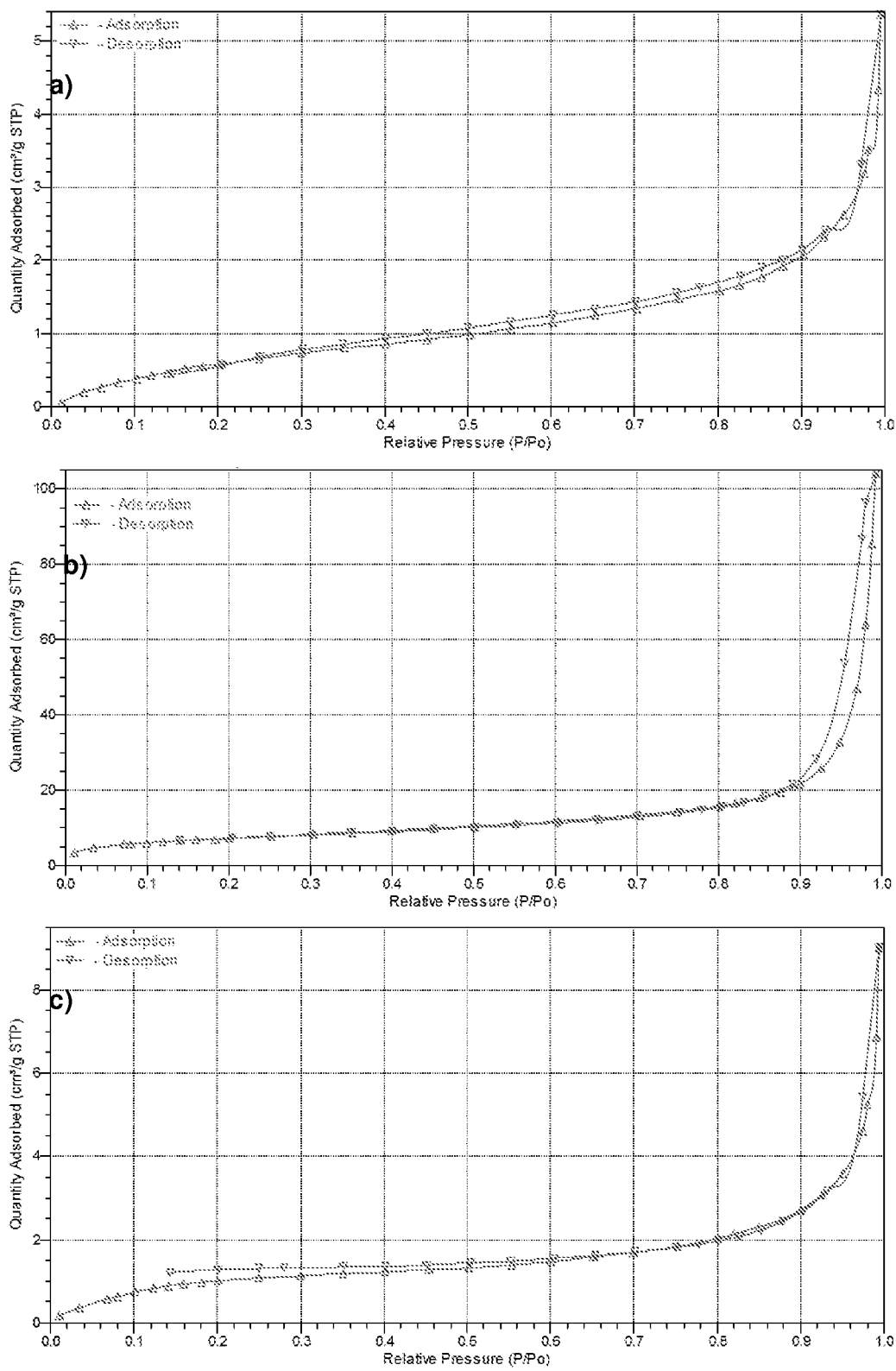
FIG. 8 shows linear isothermic plots of a) PANi-E neurosponge; b) PANi-C neurosponge; and xpi-PANi-E-C neurosponge according to this disclosure.

The synthesized PANi-neurosponge was very brittle and powdery, therefore the porosimetric analysis was carried out only for the PANi-E neurosponge, the PANi-C neurosponge and xpi-PANi-E-C neurosponge, and is shown in FIG. 8 and Table 4. FIG. 8 shows linear isothermic plots of a) PANi-E neurosponge; b) PANi-C neurosponge; and xpi-PANi-E-C neurosponge according to this disclosure. For the interpretation of porosity profiles, International Union for Pure and Applied Chemistry (IUPAC) recommendations proposed by the Subcommittee on Reporting Gas Adsorption Data were referred to (Sing et al., 1985) and the physisorption curves were compared with the isotherm types and hysteresis loops according to the IUPAC classification system. The physisorption curves for all the three scaffolds (neurosponges) corresponded to Type II isotherm thereby confirming the macroporous morphology of the scaffolds. The Brunauer-Emmett-Teller/Barrett-Joyner-Halenda (BET/BJH) surface areas, pore volume, and pore diameter were the lowest for PANi-E-NS and the highest for PANi-C-NS which can be assigned to the large diameter elastin fibres and small diameter collagen fibrils, respectively, as discussed and shown under scanning electron microscope (SEM) analysis.

In the case of xpi-PANi-E-C-NS/pharmaceutical composition, the porosity parameters lay within the PANi-E-NS and PANi-C-NS extremes which were attributed to the mix of large and small diameter fibres. Larger diameter fibres dominated the network as elastin was present in a much higher concentration than collagen (elastin:collagen::25:1).

Coming to the hysteresis loops observed in the isotherms; PANi-E-NS showed Type H3 loop which was defined by the IUPAC as "aggregates of plate-like particles giving rise to slit-shaped pores". Without being limited to theory, this was true in the case of elastin fibres as their diameter was large and these fibres form loosely coherent network leading to the formation of well-defined pore-within-a-pore. In the case of PANi-C-NS, Type H1 hysteresis loop was observed which was defined by the IUPAC as "associated with porous materials known to consist of agglomerates in fairly regular array and have narrow distributions of pore size." This appeared to be true for collagen fibers as they formed small diameter fibres which show relatively more consistent size distribution than larger diameter fibers. The agglomeration part also seemed correct as the fibers appeared to fuse together as shown in SEM.

Interestingly and unexpectedly, the xpi-PANi-E-C scaffold/NS/pharmaceutical composition demonstrated Type H1 loop up to relative pressure of 0.6 and thereafter formed an open loop. Several samples of xpi-PANi-E-C were tested to ascertain its open loop behaviour and similar loops were formed in all the samples tested for porosity. Although the concentration of collagen was minimal as compared to elastin; the presence of smaller fibers within the larger fibre network provided more aggregation to the combined network forming the H1 loop. Additionally, the open loop at lower pressure can be attributed to "a non-rigid porous structure" as per the IUPAC description of such behaviour.

TABLE 4

Surface area and porosity characteristics of PANi-E-, PANi-C- and xpi-PANi-E-C neurosponges.

| Parameter | PANi-E-NS | PANi-C-NS | xpi-PANi-E-C-NS |
| --- | --- | --- | --- |
| BET Surface Area (m$^2$/g) | 2.9107 | 26.8793 | 4.5151 |
| BJH Adsorption surface area of pores (m$^2$/g) | 2.632 | 26.322 | 3.507 |
| BJH Desorption surface area of pores (m$^2$/g) | 3.079 | 25.9760 | 2.1502 |
| BJH Adsorption volume of pores (cm$^3$/g) | 0.008183 | 0.162031 | 0.014213 |
| BJH Desorption volume of pores (cm$^3$/g) | 0.008148 | 0.161552 | 0.013033 |
| BJH Adsorption average pore diameter (Å) | 124.358 | 246.231 | 162.086 |
| BJH Desorption average pore diameter (Å) | 105.855 | 248.771 | 242.444 |

Figure 9:
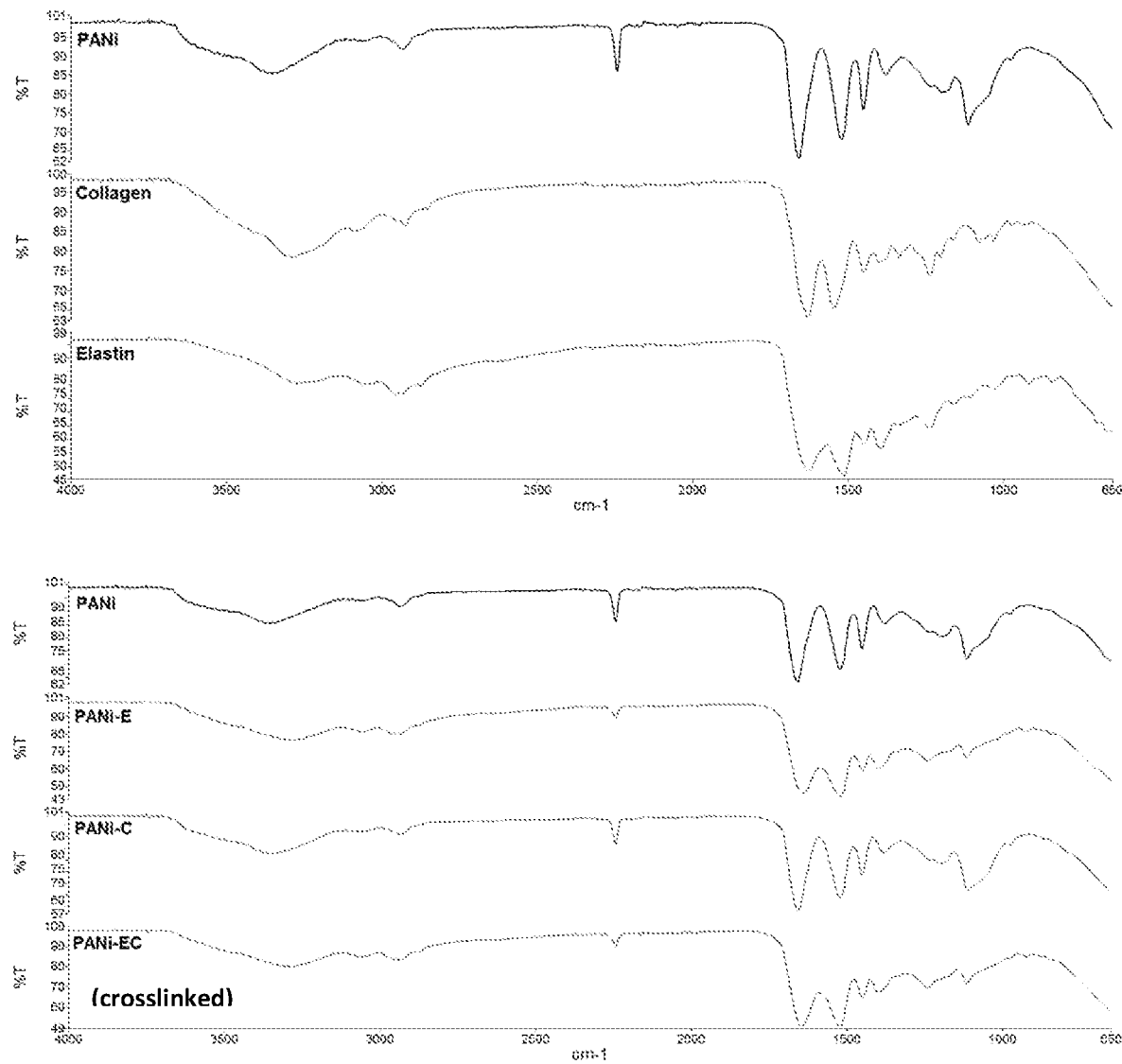
FIG. 9 shows FTIR spectra of PANi, elastin (E), collagen (C), the PANi neurosponge, the PANi-E neurosponge, the PANI-C neurosponge and the xpi-PANi-E-C neurosponge according to this disclosure.

FTIR Analysis for the Determination of the Peptide Secondary Structure within the Polymer-Peptide Neurosponge The FTIR spectrum of PANi (FIG. 9) showed characteristic wavenumber bands at 3650-3250 cm$^{-1}$ (water molecules interacting with PANi moieties (type I and II water)), 2937.56 cm$^{-1}$ (CH$_3$ symmetric stretching mode; vibrational C—H stretching), 2243.59 cm$^{-1}$ (C≡N stretching vibration), 1657.79 cm$^{-1}$ (δ C—H bending; hydrolysed acrylonitrile units formed during the polymerization process), 1519.34 cm$^{-1}$ (C—N stretching), 1450.70 cm$^{-1}$ (δ CH2 asymmetric), 1377.24 cm$^{-1}$ (N—C—H bending), 1193.87 cm$^{-1}$ (δ CH2 asymmetric), and 1113.28 cm$^{-1}$ (C—H vibration mode) (Cetiner et al., 2010; Moghadam and Bahrami, 2005; Moreno et al., 2010; Wan et al., 2007).

The characteristic amide bands in collagen appeared at 3306 cm-1 (amide A; N—H stretching vibration; hydrogen bonded N—H groups), 2964 cm$^{-1}$ (amide B; asymmetric stretch of CH2), 1640 cm-1 (amide I; C=O stretching vibrations), 1541 cm-1 (amide II; N—H bending vibrations), and 1235 cm-1 (amide III; C—H stretching). The elastin FTIR spectrum showed the corresponding amide bands at 3306 cm-1 (amide A), 2964 cm-1 (amide B), 1640 cm-1 (amide I), 1541 cm-1 (amide II), and 1235 cm-1 (amide III) (Nagai, 2010).

Figure 10:
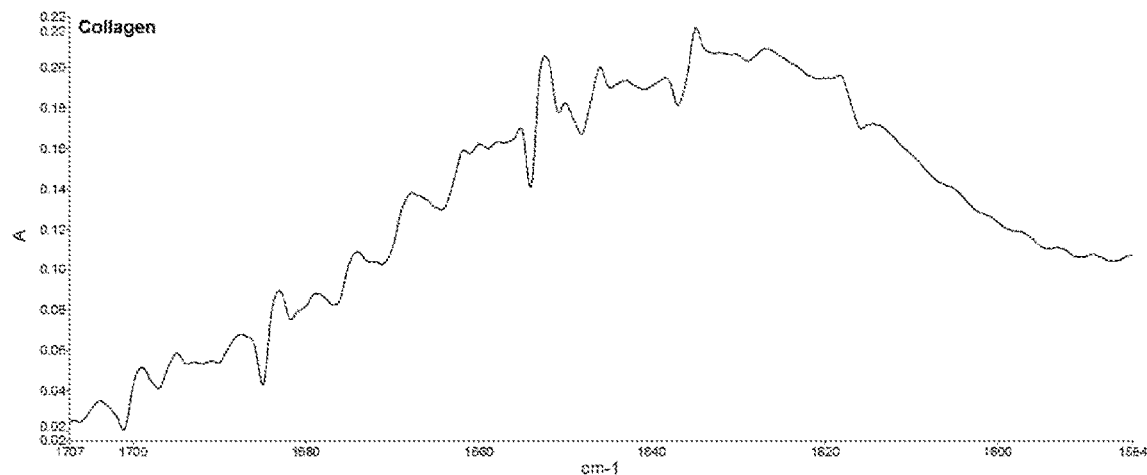
FIG. 10 shows Fourier-deconvoluted Fourier Transform/ Infra-Red (FT/IR) attenuated total reflectance (ATR) spectra corresponding to amide I peak of pristine polymers (a) elastin (E), (b) collagen (C), and (c) the PANi-E neurosponge, (d) the PANi-C neurosponge and (e) the xpi-PANi-E-C neurosponge.
Figure 10:
Figure 10:
Figure 10:
Figure 10:
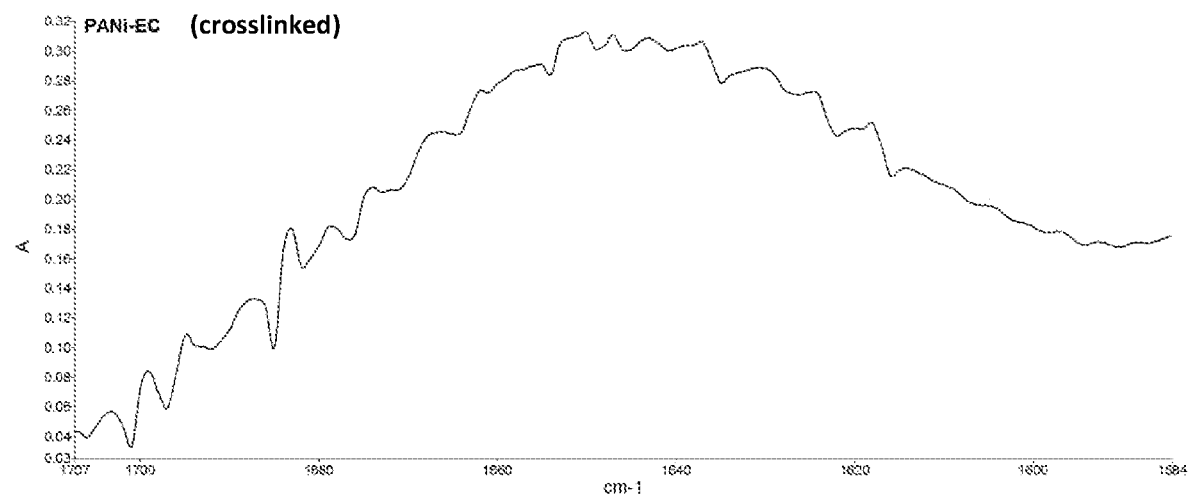

To assess the effect of PANi on the secondary structure of the constituent proteins, deconvolution of the amide I peak was carried out between 1705 and 1585 cm$^{-1}$ (FIG. 10). The following wavenumber bands were used as reference for assigning the secondary structure: 1620-1640 cm$^{-1}$≈β-sheets; 1640-1650 cm$^{-1}$=random coils; 1650-1658 cm$^1$=α-helix; 1660-1680 cm$^{-1}$=β-turns; and 1680-1695 cm$^{-1}$=β-sheets (Yang et al., 2015). FIG. 10 shows Fourier-deconvoluted Fourier Transform/Infra-Red (FT/IR) attenuated total reflectance (ATR) spectra corresponding to amide I peak of pristine polymers elastin (E), collagen (C), the PANi-E neurosponge, the PANi-C neurosponge and the xpi-PANi-E-C neurosponge.

1. PANi-E-NS: Native elastin obtained from the supplier showed characteristic amide I component peaks with β-sheets>random coils>α-helix>β-turns. However within PANi-E-NS, the elastin peptides self-assembled into random coils>β-sheets>α-helix>β-turns. Given the "intrinsically disordered domains" characteristic of elastin in vivo, the deconvolution results confirmed the formation of an ECM-mimetic scaffold (Roberts et al., 2015).
2. PANi-C-NS: Native collagen obtained from the supplier showed characteristic amide I component peaks with β-sheets>α-helix>random coils>β-turns. However within PANi-C-NS, the collagen peptides self-assembled into α-helix>random coils>β-turns>β-sheets. Collagen chains exist as triple helices in vivo. It is worth noting that the secondary structure of collagen was significantly altered in the presence of PANi as compared to elastin in the PANi-E neurosponge.
3. xpi-PANi-E-C-NS: The deconvolution of the elastin/collagen scaffold showed concentration dependent secondary structure conformation with random coils>α-helix>β-sheets>β-turns as elastin formed the majority of the peptide content in the final scaffold. The final conformation can be assigned as elastin coiled-coils intervened by collagen helices thereby perfectly mimicking the extra cellular matrix environment (Silver, 2006).

Figure 11:
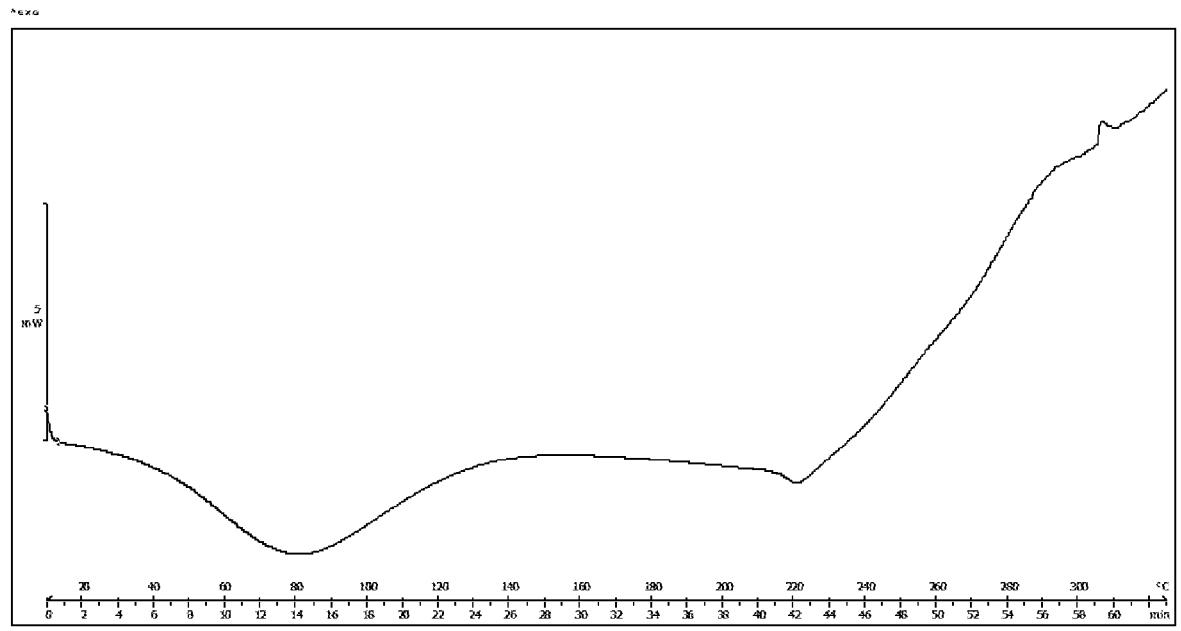
FIG. 11 shows differential scanning calorimetry (DSC) thermograms of pristine (a) collagen and (b) elastin.
Figure 11:
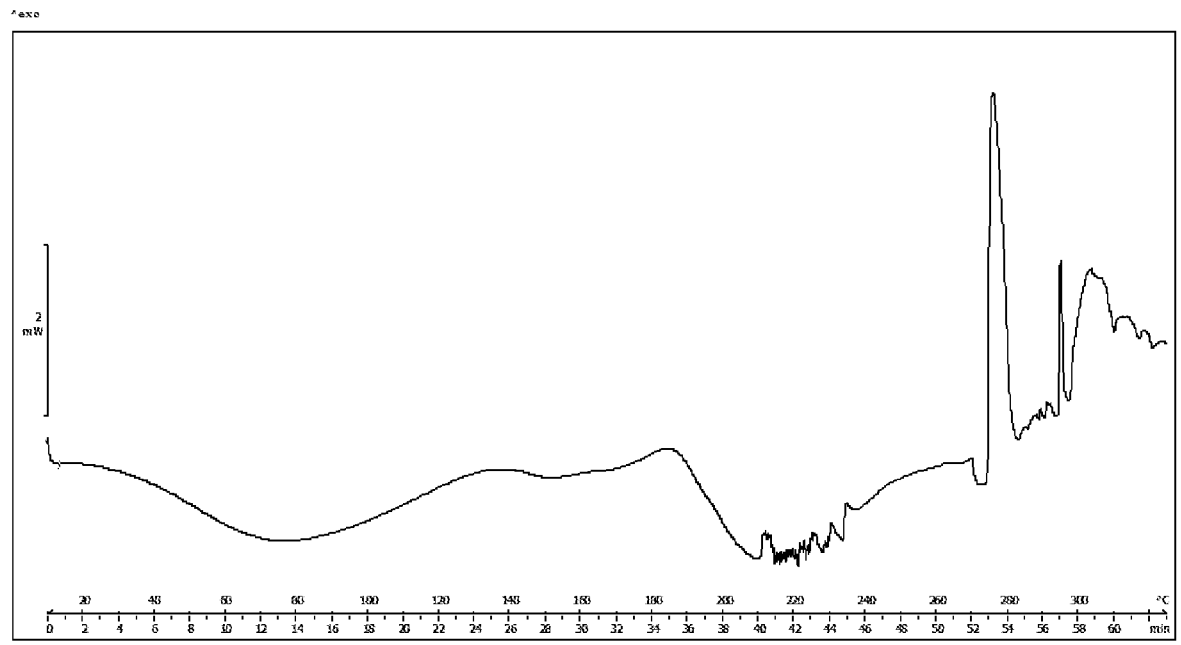
Figure 12:
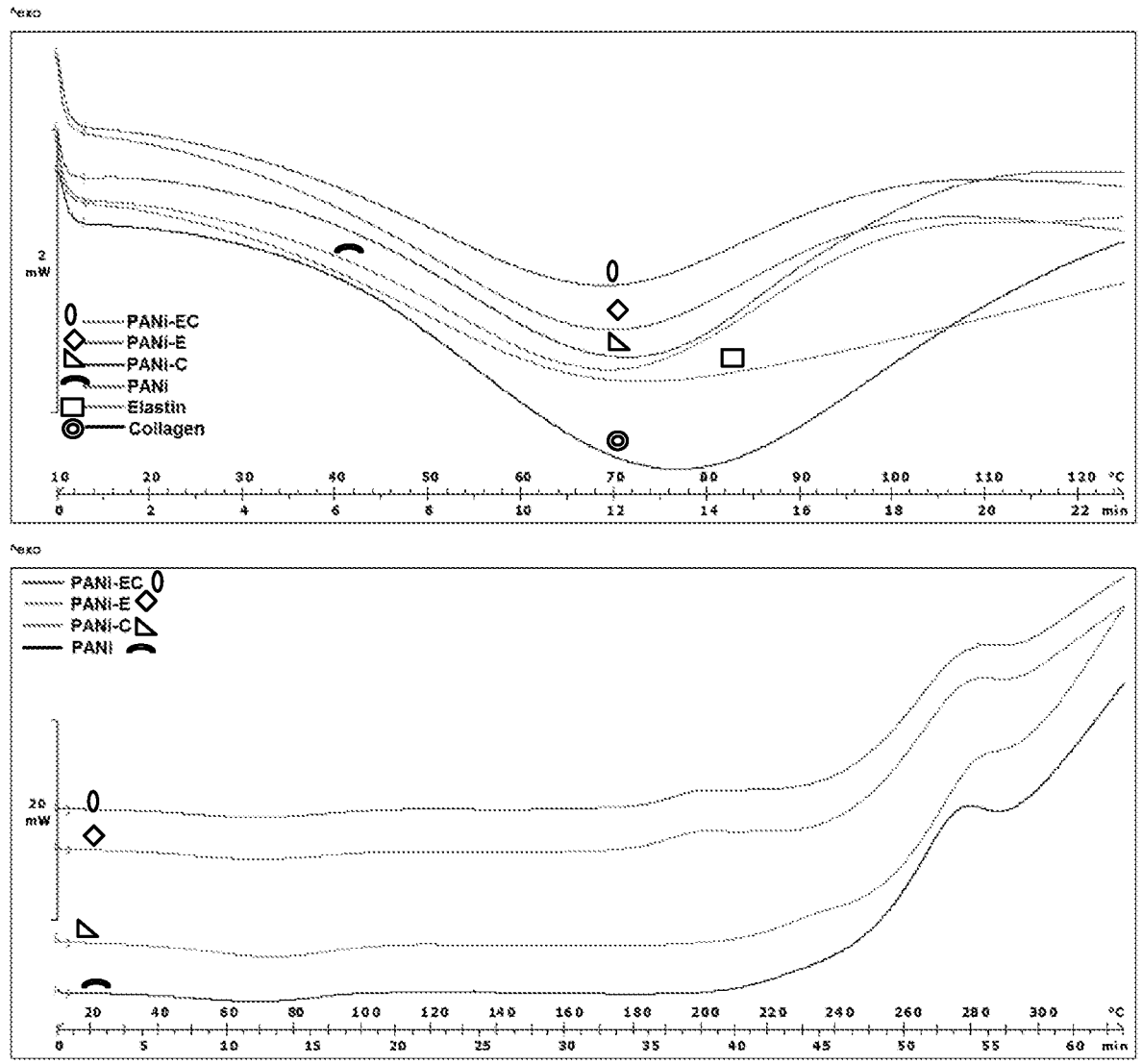
FIG. 12 shows DSC thermograms of PANi, elastin (E), collagen (C), the PANi neurosponge, the PANi-E neurosponge, the PANi-C neurosponge and the xpi-PANi-E-C neurosponge according to this disclosure.

Thermal Analysis to Ascertain Peptidic Structural Variations in the Neurosponges The DSC scans for pristine collagen, pristine elastin, PANi neurosponge, PANi-E neurosponge, PANi-C neurosponge and xpi-PANi-E-C neurosponge over 10-125 degrees showed a very broad endothermic peaks corresponding to temperature of dehydration at 76.79° C. (−200.98 J/g), 72.79° C. (−104.44 J/g), 69.42° C. (−89.19 J/g), 69.51° C. (−78.60 J/g), 71.17° C. (−122.75 J/g) and 68.91° C. (−77.35), respectively (FIG. 11 and FIG. 12). FIG. 11 shows differential scanning calorimetry (DSC) thermograms of pristine (a) collagen and (b) elastin. FIG. 12 shows DSC thermograms of PANi, elastin (E), collagen (C), the PANi neurosponge, the PANi-E neurosponge, the PANI-C neurosponge and the xpi-PANi-E-C neurosponge according to this disclosure at various temperature ranges. The second from 10-325° C. still contained the dehydration endothermic peak representing the bound water in the biomolecules and the PANi blends. To assess the thermal transitions in the blend scaffolds, one characteristic and defining peak from each of the pristine components was chosen. In pristine peptide samples, the endothermic peak at 220° C. for collagen can be attributed to the temperature of denaturation while the exothermic peak at 185° C. for elastin can be ascribed to the amorphous glass transition. The DSC curve of PANi showed a clearly distinguishable exothermic decomposition peak at 280° C. In the case of PANi-E-NS, the exothermic transition of elastin formed a plateau between 175-200° C. confirming the presence of an unordered structure (random coils) as compared to β-sheets which formed a well-defined exotherm. The decomposition exotherm corresponding to PANi shifted from 280 to 285° C. thereby attesting the improved stability of the scaffold structure.

In the case of PANi-C-NS, the denaturation temperature of collagen appeared as a broad band between 187 and 234° C. with a peak at 213° C. This could be attributed to the transition of a more stable β-sheet (pristine elastin) to a less stable α-helix in PANi-C-NS thereby reducing the protein denaturation temperature (Henzler Wildman et al., 2002). Likewise PANi-E-NS, the decomposition temperature corresponding to PANi shifted to a higher temperature (284° C.) in PANi-C-NS further substantiating the stabilizing effect of proteins on the PANi-NS scaffold. The endothermic denaturation peak of collagen disappeared or merged with the glass transition endotherm plateau in xpi-PANi-E-C-NS. Without being limited to theory, this could be due to the very low concentration of collagen in xpi-PANi-E-C scaffold (2% w/w). The PANi decomposition peak remained unchanged at 285° C. in xpi-PANi-E-C as compared to PANi-E and PANi-C.

In conclusion, the DSC analysis successfully corroborated the FTIR analysis with respect to the secondary structure transitions of the component peptides (elastin and collagen) within the scaffold structure as well as provided confirmation of the enhanced stability of the scaffold.

Texture Analysis Proving the Unique Collagen-Elastin Mechano-Synergism

For the texture profiling of the peptide based scaffolds (PANi-E-NS, PANi-C-NS and xpi-PANi-E-C-NS), the hypothesis was based on the following statement "amorphous polymers such as elastin behave as rubber-like materials whereas force-transmitting rigid proteins such as collagen exist as extended conformations and behave as do stiff ropes" (Silver, 2006).

The textural analysis was conducted on hydrated samples and the PANi only neurosponges and the PANi-E neurosponges were too soft and brittle when dry and crumbled into powdery mass when lifted with forceps. Even in hydrated state, PANi- and PANi-E neurosponges were too soft to be lifted with steel forceps, therefore flat-end plastic forceps were used to lift and place these scaffolds on the stage. The scaffolds were cut using a razor blade in hydrated state. For texture analysis, compressive strain was applied at 10 to 25% with identical test and post-test speeds and data was analysed to obtain maximum strength, deformation energy, rigidity gradient, % matrix resilience (FIG. 13). FIG. 13 shows physico-mechanical properties of the PANi neurosponge, the PANi-E neurosponge, the PANI-C neurosponge and the xpi-PANi-E-C neurosponge according to this disclosure under partial applied strain values of 10-25% ($SD_{(ML)}$≤0.04; $SD_{(DE)}$≤0.05; $SD_{(RG)}$≤0.08; $SD_{(MR)}$≤9.2; n=3). The scaffold contained PANi as the common component and hence the scaffolds were compared with respect to the peptide content. Among the bicomponent systems, PANi-E-NS and PANi-C-NS, PANi-E-NS provided the highest resilience due to its rubbery nature while collagen provided the lowest values due to its rigid nature, at higher applied strains. Conversely, the matrix strength and deformation energy values were higher for PANi-C-NS than PANi-E-NS. With an increase in matrix strength, deformation energy and rigidity gradient, the resilience of the matrix decreased and vice versa. Addition of elastin to PANi although increased the solid content (PANi:elastin≈1:1), a decrease in matrix strength and deformation energy were observed. Although collagen was added at a very low concentration (0.4% w/v in the formulation mixture); the matrix strength, deformation energy and rigidity gradient of PANi-C-NS were relatively higher than that of PANi at higher applied strain. At lowest applied strain (10%), the effect of peptide addition on mechanical parameters was not much evident. It can thus be implied, without being limited to theory, that PANi acted as a physicomechanically neutral polymer and performed as per the nature of the added peptide biomaterial with no additive results obtained. This further implied the efficient formation of an interpenetrating network between the polymer and the peptide biomaterial wherein the biomaterials are blended well together while still reflecting individual properties. Matrix resilience, as well as rigidity, are very important mechanical properties inherent to scaffolds as these parameters directly affect the cellular response after implantation (Lo et al., 2000). However, increasing either of the parameters decreases the other parameter making it very difficult to maintain the required resilience-rigidity balance or simply the softness-stiffness balance.

In the case of xpi-PANi-E-C-NS, elastin and collagen formed a mechanically optimized scaffold with PANi with the highest matrix strength capable of being handled with steel forceps.

The cylindrical xpi-PANi-E-C neurosponge/pharmaceutical compositions were capable of holding their own weight up to three layers (FIG. 2). Remarkably and unexpectedly, the xpi-PANi-EC neurosponge showed significantly higher matrix strength (force required to cause deformation), deformation energy (firmness) and rigidity gradient (stiffness) as compared to PANi-NS, PANi-E-NS, and PANi-EC-NS.

More remarkably and unexpectedly, even after the almost two-fold increase in stiffness and firmness, the resilience remained within the range of PANi-E-NS and higher than PANi-NS and PANi-C-NS at higher applied strains. Together with PANi, the first such spinomimicking scaffold is disclosed wherein PANi acted as a chemically neutral polymer but affected the orientation of both collagen and elastin to their natural form together forming the much proclaimed "reinforced composite of collagen and elastin" (Miranda-Nieves and Chaikof, 2016; Oxlund and Andreassen, 1980; Muiznieks and Keeley, 2013).

The unique and advantageous physico-chemical properties of the xpi-PANi-E-C neurosponge/pharmaceutical composition could not have been predicted based on an analyses of its component chemical compounds [polyacrylonitrile (PANi), elastin (E), and collagen], nor from an analyses of PANi-NS, PANi-E-NS and PANi-C-NS. Without being limited to theory, the unique interactions between crosslinked PANi, elastin (E) and collagen (C) provide an interpenetrating polymer network having spinomimetic qualities. By mimicking human and/or animal spinal cord tissue and by providing channels and/or tunnels and/or protrusions within the channels and/or tunnels, the pharmaceutical composition according to this disclosure facilitated nerve tissue and/or axonal growth and/or repair.

Matrix Hydration and Degradation Profile of Spinomimetic Neurosponges

To assess the response of lyophilized scaffolds (the PANi neurosponge, the PANi-E neurosponge, the PANi-C neurosponge and the PANi-E-C neurosponge) towards neuronal aqueous medium (pH 7.4), the scaffold was tested for their ability to hold water (% water holding capacity; WHC), wet weight (% matrix hydration; MH), and physical degradation (PD) (FIG. 14). FIG. 14 shows a bar chart depicting matrix hydration and degradation profiles of the PANi-E neurosponge, the PAM-C neurosponge and the xpi-PANi-E-C neurosponge ($SD_{(WR)}$≤202; $SD_{(MH)}$≤118; $SD_{(MD)}$≤6; n=3). WHC referred to the maximum water a scaffold can hold within the matrix network as well as in the matrix pores and effectively is the aqueous medium present in the scaffold at a given time (before draining out the aqueous medium). WHC represented the media available for the cells to grow and proliferate within the scaffold. MH was calculated by draining out the excess scaffold surface water as well as the water within the pores by absorbing the water onto a filter paper until an equilibrium weight is reached. MH should not be confused with % swelling as the scaffolds used were previously lyophilized in their fully hydrated state and therefore showed no increase in size. Physical degradation referred to as the degradation of the scaffold in aqueous medium and represented the ability of the scaffold to hold-together its matrix.

PANi-E-NS showed very low % WHC and % MH as almost 50% of scaffold was degraded within 24-hours. This was due to the very weak mechanical strength of the scaffold. This was evident by the presence of scaffold particles in the hydration tube and the colour of the hydration medium turned greenish-yellow due to the presence of elastin in the medium. Once the loose structure was degraded, the scaffold architecture reached equilibrium at 40-45% matrix remaining in the aqueous medium which was very soft and brittle. Such scaffolds are not suitable for tissue engineering applications as they lose significant amount of matric and hence lose their matrix integrity within a very short time after implantation.

In contrast, PANi-C-NS formed a rigid scaffold with no degraded particles being visible throughout the study period. The % WHC values reached ≈1000% and only equilibrated by day 4. Most of the aqueous medium retained in the matrix structure as the % MH was close to ≈700% on day 1. The physical degradation data complemented WHC and MH and showed a minimal degradation of ≈15% by day 28. This may be explained owing to the least resilient nature of PANi-C-NS which delayed the entry of water molecules into the matrix and hence delayed the hydration of the scaffold. The significantly higher % WHC in PANi-C-NS as compared to PANi-E-NS can be attributed to significantly higher porosity of PANi-C-NS (Table 4) capable of holding higher amount of aqueous medium within the scaffold. Furthermore, the nano-web formed by the collagen fibrils retained significantly higher amount of water while draining giving higher % MH values. Similarly, due to less resilient nature the water molecules were unable to affect enough network movements leading to almost negligible physical degradation of the scaffold. Such scaffold are also not suitable and non-conducive for tissue regeneration as they form rigid structures, degrading very slowly, and hence developing space constraints for the proliferating and growing tissue.

In the case of xpi-PANi-E-C-NS, intermediate values for % WHC and % MH were observed for initial 4 days and thereafter showed lowest values for % WHC and % MH. A closer look at the three bar charts revealed that % WHC and % MH for xpi-PANi-E-C-NS inversely followed its physical degradation profile. Although, no loose particles were visibly evident, the hydration vessel showed a greenish-yellow tinge during the degradation period confirming the leaching of elastin from the scaffold. No shape distortion was observed over the 4-weeks period confirming the maintenance of matrix structure throughout. The unique stiffness-softness paradigm of xpi-PANi-EC-NS produced an almost linear degradation profile over the 4-weeks period ($R^2=0.9802$) with ≈50% matrix degradation at day 28. Most importantly, due to porosity profile closer to PANi-E-NS, the MH was only 25% less than WHC for xpi-PANi-E-C-NS, thereby confirming a most optimum solid-liquid balance among the three formulations. With first order degradation profile and comparatively higher solid-liquid ratio, xpi-PANi-E-C-NS appeared most suited for neural tissue regeneration.

Bioactive Release from the Spinomimetic Neurosponges

The drug release profiles for the three core scaffolds (the PANi-E neurosponge, the PANi-C neurosponge and the PANi-E-C neurosponge) closely followed the porosity, texture analysis, and hydration/degradation data.

In contrast to other polymeric archetypes, the release profiles for dexamethasone and curcumin were relatively superimposable in PANi-based scaffolds (FIG. 15).

PANi-E-NS showed a rapid release of the bioactives with ≈90% released within 3 to 8 hours and a complete release of bioactives within 24 hours. This would be undesirable in the case of a spinal implant where one would require release of a drug active over a longer period of time. The rapid release can be easily attributed to weak mechanical strength and hence rapid degradation of the polymer-peptide matrix—a typical example of dose dumping behaviour.

Dex release from PANi-C-NS was relatively rapid as compared to curcumin with both the bioactives released completely within 72 hours. Although, the % WHC and % MH values were higher in PANi-C-NS (as compared to PANi-E-NS), the higher matrix strength and intact scaffold architecture delayed the release of drugs. However, the high porosity and large pores in PANi-C-NS led to the complete release of bioactives within 3 days.

One would expect xpi-PANi-E-C to show a release profile in between PANi-E-NS and PANi-C-NS. However, contrary to what might be expected, this is not what is observed. The xpi-PANi-E-C-NS shows the slowest drug release profile, and is considered to most desirable for application as a spinal implant for treating a spinal cord related injury.

xpi-PANi-E-C-NS did not show intermediate release behaviour. The more sustained and delayed release in the case of xpi-PANi-E-C-NS as compared to PANi-E-NS and PANi-C-NS may, without being limited to theory, be attributed to its relatively higher mechanical strength, highest matrix content (or highest density) as both elastin and collagen were incorporated into the scaffold, and lower hydration characteristics. The drug release profile of this scaffolds conform to the therapeutic regimen followed for acute spinal cord injuries with at least 75% of drug released within first 24 hours (xpi-PANi-E-C-NS). This attests the applicability of hydrated, drug-loaded, multi-macroporous, nano-to-microfibrous, stiff-and-soft, polymer-peptide platforms towards spinal cord injury intervention.

Interpretation of Geometrical Assimilation of Molecular Complex Via Molecular Mechanics Simulations While performing molecular simulations in vacuum, it was observed that the —C≡N functionality of PANi formed no H-bonding with the —NH$_2$, —COOH, or —OH functional groups of the peptide molecules—collagen and elastin. However, the PANi molecule did undergo certain geometrical variations which can be attributed to the non-bonding interactions arising from the stretching, bending and torsional strain experienced by the PANi molecule in close vicinity of peptide molecules and vice versa. To visualize the variations in the geometry of PANi, the inertial axis of the molecule in its native state (PANi) as well as after the energy minimization of molecular complexes (PANi-E, PANi-C, and xpi-PANi-EC) was captured. Interestingly, when compared at similar positions of the inertial axes, the geometry of the PANi molecule traversed from a semicircle (PANi alone) through a question mark shape (PANi-E) and reverse question mark shape (PANi-C) to an S-shape of xi-PANi-E-C as shown in FIG. 16. Furthermore, the H-bonding among the collagen-elastin molecular complex (FIG. 17a) significantly increased in the close vicinity with PANi (FIG. 17b). These geometrical and H-bonding transitions further confirmed our propositions regarding the change in secondary structure of peptide molecules in polymer-peptide blends (see FTIR and DSC analyses discussion for details).

Concluding Remarks

PANi-NS, PANi-E-NS, PANi-C-NS and xpi-PANi-E-C-NS were synthesized. The unique feature of the xpi-PANi-E-C neurosponge included the formation of a fibrous neurotunnel architecture mimicking the native spinal cord. The physicochemical characterization revealed that the secondary structure of the peptide molecules rearranged in the presence of PANi to their native extra cellular matrix form confirming the self-assembling nature of the polymer-peptide architecture. Furthermore, the xpi-PANi-E-C neurosponge provided a perfect balance of matrix resilience and matrix hardness similar to the native collagen-elastin complex in vivo. Given the spinomimetic nature of xpi-PANi-E-C as an artificial neuronal extracellular matrix conducive to growth of neuronal tissue and axons, xpi-PANi-E-C was further tested in vivo for its ability to regenerate and support the neuronal tissue in a complete transaction spinal cord injury model.

REFERENCES

Cetiner S, Karakas H, Ciobanu R et al 2010. Polymerization of pyrrole derivatives on polyacrylonitrile matrix, FTIR-ATR and dielectric spectroscopic characterization of composite thin films. Synthetic Metals 160:1189-1196.

Daamen W F, van Moerkerk H T B, Hafmans T, Buttafoco L, Poot A A, Veerkamp J H, van Kuppevelt T H 2003. Preparation and evaluation of molecularly-defined collagen-elastin-glycosaminoglycan scaffolds for tissue engineering. Biomaterials 24:4001-4009.

Henzler Wildman K A, Lee D K, Ramamoorthy A 2002. Determination of α-helix and β-sheet stability in the solid state: A solid-state NMR investigation of poly(L-alanine). Biopolymers 64:246-254.

Miranda-Nieves D, Chaikof E L 2016. Collagen and elastin biomaterials for the fabrication of engineered living tissues. ACS Biomater Sci Eng (In press). DOI: 10.1021/acsbiomaterials.6b00250.

Moghadam S S, Bahrami S H 2005. Copolymerization of acrylonitrile-acrylic acid in DMF-water mixture. Iran Polym J 14:1032-1041.

Moore M J, Friedman J A, Lewellyn E B et al 2006. Multiple-channel scaffolds to promote spinal cord axon regeneration. Biomaterials 27:419-29.

Moreno M, Ana M A S, Gonzalez G, Benavente E 2010. Poly(acrylonitrile)-montmorillonite nanocomposites: Effects of the intercalation of the filler on the conductivity of composite polymer electrolytes. Electrochimica Acta 55:1323-1327.

Muiznieks L D, Keeley F W 2013. Molecular assembly and mechanical properties of the extracellular matrix: A fibrous protein perspective. Biochim Biophys Acta 1832: 866-875.

Nagai T 2010. Characterization of Acid-Soluble Collagen from Skins of Surf Smelt (*Hypomesus pretiosus japonicus* Brevoort). Food Nutrition Sci 1:59-66.

Oxlund H, Andreassen T T 1980. The roles of hyaluronic acid, collagen and elastin in the mechanical properties of connective tissues. J Anat 131:611-620.

Roberts S, Dzuricky M, Chilkoti A 2015. Elastin-like polypeptides as models of intrinsically disordered proteins. FEBS Lett 589:2477-2486.

Silver F H 2006. Macromolecular Structures in Tissues. Chapter 2 in Mechanosensing and Mechanochemical Transduction in Extracellular Matrix. Edited by: Frederick H. Silver. Springer US. Pp 28-75. DOI: 10.1007/978-0-387-28176-6_2.

Ulijn R V, Smith A M 2008. Designing peptide based nanomaterials. Chem Soc Rev 37:664-75. van Vlierberghe S, Dubruel P, Schacht E 2011. Biopolymer-based hydrogels as scaffold for tissue engineering applications: A review. Biomacromolecules 12:1387-1408.

Zhang S 2002. Emerging biological materials through molecular self-assembly. Biotech Adv 20: 321-39.

Zhang S 2003. Fabrication of novel biomaterials through molecular self-assembly. Nat Biotechnol 21:1171-8.

EXAMPLES—ANIMAL STUDIES

The animal studies presented here below include in vivo evaluation of the xpi-PANi-E-C pharmaceutical composition/NS according to a first aspect of this disclosure conducted in a complete transection spinal cord injury model.

Methods

PC12 Cell Culture and MTT Proliferation Assay

Rat adrenal gland pheochromocytoma PC12 mixed adherent/suspension cell line from Cellonex (Separations, South Africa) was cultured in tissue culture treated (TPP) T-75 flasks using DMEM supplemented with 10% v/v DES, 5% v/v FBS and 1% v/v, P/S/AB solution in a humid 5% $CO_2$ atmosphere at 37° C. The culture medium was replaced at 75% every 2 days. For the detection of cell proliferation and cyto-compatibility of the electrospun fibers, the MTT-based Roche Cell Proliferation Kit I was utilised. xpi-PANi-E-C pharmaceutical composition samples were sterilized under UV light for 12 hours before overnight incubation in 400 μL culture medium containing 10% v/v DES, 5% v/v FBS and 1% v/v P/S/AB in a 48-well plate maintained at 37° C. at 5% $CO_2$. PC12 cells were seeded onto the xpi-PANi-E-C pharmaceutical composition samples at a density of $2 \times 10^4$ cells/well and incubated for 72 hours. Thereafter, 40 μL MTT solution was added to each well followed by a further 4-hour incubation period after which 400 μL solubilising agent was added to dissolve the formazan crystals. The entire well contents were aspirated off, placed into 2 mL Eppendorf tubes and centrifuged at 2000 rpm for 5 minutes to separate suspended cells. The resulting supernatant was transferred into a 96-well plate and measured for absorbance at 550 nm using a multi-plate reader (BioTek, USA). Relative cell proliferation was measured by using the following equation:

$$\%R_p = (A_{test}/A_{control}) \times 100 \quad \text{Equation 1}$$

where, $R_p$=Relative cell proliferation; $A_{test}$=Absorbance of the hydrogel membrane containing sample; $A_{control}$=Absorbance of the control (Ray et al., 2010).

Pilot Study to Evaluate the In Vivo Implantation of the Xpi-PANi-E-C-NS

Adult female Sprague-Dawley rats were used for the in vivo testing of the performance of xpi-PANi-E-C-NS. The rats were divided into two groups:

Group 0: Control group with spinal cord injury.
Group II: Injured rats+xpi-PANi-E-C-NS The groups had 4 animals each. The rats were anesthetized (65 mg/kg ketamine i.p./7.5 mg/kg xylazine i.p.) before shaving the back of the rats. After placing the rat on the operating table, a small incision was made (≤2 cm) along the dorsal midline. The paraspinal muscles attached to the spinous processes and laminae were subperiosteally dissected to reach the dura. Using curved, sharp scissors, a laminectomy was performed at previously determined and marked positions corresponding levels T8-T10. Violation of facet joints was carefully avoided. Once the dura was exposed, sharp micro-forceps and -scissors were used to cut the dura and a 1 mm segment of the spinal cord was removed (level T9). The stumps were then retracted making a 2 mm gap in the spinal cord for implantation of the xpi-PANi-E-C sponge/scaffold. The transacted site was irrigated with Ringer's solution to visualize the bottom of the canal as a confirmation of complete transection. The xpi-PANi-E-C sponge/scaffold was implanted, placed or injected within the 2 mm gap. The skin was sutured after the surgical process (Moore et al., 2006, Meiners et al., 2007, Tysseling-Mattiace et al., 2008). All procedures were performed in accordance with the Animal Ethics Screening Committee guidelines of the University of the Witwatersrand, Johannesburg.

Post-Operative Animal Care

Post-operatively, animals were kept in their cages over a previously warmed sack to maintain their body temperature. In certain cases, the animals were kept in an incubator. Lactated Ringer's solution (subcutaneously) and baytril (33 mg/kg, subcutaneously) were administered immediately after surgery and for 3 days to maintain initial hydration and control infection, respectively. Bladders were manually emptied thrice daily throughout the duration of the study or until the bladder function was restored. In the event of discomfort, curatex (subcutaneously, twice daily) was administered at prescribed dosage. Rats exhibiting any hindlimb movement 24 hours after the injury were excluded from the study (Tysseling-Mattiace et al., 2008).

Immunohistochemical Analysis of the Spinal Cord Tissue Samples

On day 28 after spinal cord injury, animals were euthanized with pentobarbital (50 mg/kg, i.p.) and perfused with 0.01M phosphate-buffered saline, followed by 4% paraformaldehyde (PFD). The spinal cord was dissected and post-fixed overnight in 4% paraformaldehyde. The spinal cords were then embedded in paraffin wax blocks and were sectioned horizontally with a microtome and mounted on to superfrost plus slides. The aim of this study was to assess the extent of degeneration/regeneration within injured rat spinal cord, incorporating Hematoxylin and Eosin (H&E) and immunohistochemistry (IHC) assays. 4-5 μm sections were taken from 3 levels throughout each block, ensuring the full inclusion of each lesion.

In the first instance, H&E staining was used to characterise the morphological features present on each slide. Secondly, a range of immunohistochemical (IHC) stains were applied, in order to further classify the structural and molecular processes present, as follows:

ED1 (CD68): To determine the extent/quantity of glial/histiocytic infiltrate (chronic inflammation (myelitis)).

Calpain/inducible form Nitric Oxide Synthase (iNOS): To determine the extent of ongoing proteolysis (myelin and cytoskeletal) and assess the extent to which NO is expressed within the pathogenesis (degeneration) of spinal cord injury/lesion progression, respectively.

Glial Fibrillary Acidic protein (GFAP)/Neurofilament 200 (NF-200): To determine the extent of structural neuroglial/axonal disorganisation.

The H&E-stained sections were graded as follows:

NAD: No abnormality detected. Morphology within the parameters of control specimens, an absence of demyelination/nerve fibre degeneration.

1: Minimal lesion. Scattered and individualised foci of nerve fibre demyelination, characterised by the presence of dilated myelin sheaths and condensation of axoplasm (inclusive of "digestion chambers"), with or without a minimal infiltrate of microglial/gitter cells.

2: Slight lesion. Multi-focal-to-coalescing areas of nerve fibre degeneration, minimal inflammatory cell infiltration.

3: Moderate lesion. Diffuse demyelination with focally-extensive areas of total nerve fibre loss and replacement by myriad vacuolated gitter cells, with reactive and hypertrophic endothelial cells and early fibrous tissue deposition (granulation tissue; chronic-active myelitis).

4: Marked lesion. As 3, with total transection of the nerve and replacement by inflammatory cell inflammation and early-stage repair.

5: "Reparative phenotype". Focally-extensive areas of spinal cord replacement by large numbers of multinucleate cells, intermixed with fibrillar and homogeneous deposits of extra-cellular matrix (a mix of multinucleate glial cells admixed with degenerate and presumptive regenerate neuroblasts). Peripheral areas representative of grade 4 change.

The ED1-stained sections were graded as follows, based upon an average number of positive cells, per 40× high-power-field objective (approximately 60 cells in total):

0: An average of 1-2 cells per 40× high-power field.
1: An average of 2-10 cells per 40× high power field.
2: An average of 10-20 cells per 40× high power field.
3: An average of 20-30 cells per 40× high power field.
4: An average of >30 cells per 40× high power field.

The iNOS-stained sections were graded as follows, based upon an average intensity of staining over each specimen, generally observable at lower microscope objectives:

0: Slight staining; considered to be within a control ("normal") range.
1: Minimally increased staining intensity.
2: Slight-moderately increased staining intensity; generally correlated with more severe change.

The GFAP-stained sections were graded as follows, based upon an overall pan-structural (or lesional) analysis of staining, taken across approximately ten 60× high-power-field objectives (approximately 20-40 cells per field):

0: Within normal limits; structural integrity retained across grey/white matter tracts. Fine reticular network intact.
1: Minimal disruption of linear fibre alignment; no discernable loss of protein/staining quantity/intensity.
2: Slight loss of linear fibre alignment; notable decrease in protein/staining quantity/intensity.
3: Major disruption of linear fibre alignment; marked loss of protein/staining quantity/intensity (characteristic of transected areas).
4: Marked loss of reticular network with replacement by homogeneous GFAP-positive matrix. Marginal zone areas display branching and thickening of fibres (characteristic of the "reparative phenotype").

The NF-200-stained sections were graded as follows, based upon an overall pan-structural (or lesional) analysis of staining, taken across approximately ten 60× high-power-field objectives (approximately 20-40 cells per field):

0: Within normal limits; structural integrity retained across grey/white matter tracts. Tubular network intact.
1: Minimal disruption of linear tubular alignment with minimal variation in tubular diameter; no discernable loss of protein/staining quantity/intensity.
2: Slight disruption of linear tubular alignment with variation in tubular diameter; notable decrease in protein/staining quantity/intensity.
3: Major disruption of linear tubular alignment with marked rounding of retained tracts; marked loss of protein/staining quantity/intensity (characteristic of transected areas).
4: Total or near-total loss of tubular structures; virtual absence of protein, with occasional rounded residual foci. Marginal zones areas display grade 3 loss of tubular structures (characteristic of the "reparative phenotype").

Behavioural Testing—Functional Outcome (BBB Score)

The behavioural testing was carried out by using the open field method proposed by Basso et al., 1995 and the functional outcomes of various neurosponges tested were quantified by using the respective, famously known, 21-point Basso, Beattie, Bresnahan (BBB) locomotor rating scale (Table 5). The method was slightly modified by using the rat cage tray (without the lid) so as to provide a height function to the functional outcome as well as to qualitatively determine the extent of hind limb stretch in the rat.

TABLE 5

The 21-point Basso, Beattie, Bresnahan (BBB) locomotor rating scale and operational definitions of categories and attributes (Basso et al., 1995).

| Score | Functional outcome |
|---|---|
| 0 | No observable hindlimb (HL) movement |
| 1 | Slight movement of one or two joints, usually the hip and/or knee |
| 2 | Extensive movement of one joint or extensive movement of one joint and slight movement of one other joint |
| 3 | Extensive movement of two joints |
| 4 | Slight movement of all three joints of the HL |
| 5 | Slight movement of two joints and extensive movement of the third |
| 6 | Extensive movement of two joints and slight movement of the third |
| 7 | Extensive movement of all three joints of the HL |

TABLE 5-continued

The 21-point Basso, Beattie, Bresnahan (BBB) locomotor rating scale and operational definitions of categories and attributes (Basso et al., 1995).

| Score | Functional outcome |
|---|---|
| 8 | Sweeping with no weight support<br>or<br>plantar placement of the paw with no weight support |
| 9 | Plantar placement of the paw with weight support in stance only (i.e., when stationary)<br>or<br>occasional, frequent, or consistent weight supported dorsal stepping and no plantar stepping |
| 10 | Occasional weight supported plantar steps, no forelimb (FL)-HL coordination |
| 11 | Frequent to consistent weight supported plantar steps and no FL-HL coordination |
| 12 | Frequent to consistent weight supported plantar steps and occasional FL-HL coordination |
| 13 | Frequent to consistent weight supported plantar steps and frequent FL-HL coordination |
| 14 | Consistent weight supported plantar steps, consistent FL-HL coordination; and predominant paw position during locomotion is rotated (internally or externally) when it makes initial contact with the surface as well as just before it is lifted off at the end of stance<br>or<br>frequent plantar stepping, consistent FL-HL coordination, and occasional dorsal stepping |
| 15 | Consistent plantar stepping and consistent FL-HL coordination; and<br>no toe clearance or occasional toe clearance during forward limb advancement;<br>predominant paw position is parallel to the body at initial contact |
| 16 | Consistent plantar stepping and consistent FL-HL coordination during gait; and<br>toe clearance occurs frequently during forward limb advancement;<br>predominant paw position is parallel at initial contact and rotated at lift off |
| 17 | Consistent plantar stepping and consistent FL-HL coordination during gait; and<br>toe clearance occurs frequently during forward limb advancement;<br>predominant paw position is parallel at initial contact and lift off |
| 18 | Consistent plantar stepping and consistent FL-HL coordination during gait; and<br>toe clearance occurs consistently during forward limb advancement;<br>predominant paw position is parallel at initial contact and rotated at lift off |
| 19 | Consistent plantar stepping and consistent FL-HL coordination during gait; and<br>toe clearance occurs consistently during forward limb advancement;<br>predominant paw position is parallel at initial contact and lift off; and<br>tail is down part or all of the time |
| 20 | Consistent plantar stepping and consistent coordinated gait; consistent toe clearance;<br>predominant paw position is parallel at initial contact and lift off; tail consistently up;<br>and trunk instability |
| 21 | Consistent plantar stepping and coordinated gait, consistent toe clearance,<br>predominant paw position is parallel throughout stance, consistent trunk stability, tail consistently up |

Definitions

Slight: partial joint movement through less than half the range of joint motion

Extensive: movement through more than half of the range of joint motion

Sweeping: rhythmic movement of HL in which all three joints are extended, then fully flex and extend again; animal is usually sidelying, the plantar surface of paw may or may not contact the ground; no weight support across the HL is evident No Weight Support: no contraction of the extensor muscles of the HL during plantar placement of the paw; or no elevation of the hindquarter Weight Support: contraction of the extensor muscles of the HL during plantar placement of the paw, or elevation of the hindquarter Plantar Stepping: The paw is in plantar contact with weight support then the HL is advanced forward and plantar contact with weight support is re-established Dorsal Stepping: weight is supported through the dorsal surface of the paw at some point in the step cycle FL-HL Coordination: for every FL step an HL step is taken and the HLs alternate Occasional: less than or equal to half; <50%

Frequent: more than half but not always; 51-94%

Consistent: nearly always or always; 95-100%

Trunk Instability: lateral weight shifts that cause waddling from side to side or a partial collapse of the trunk Results and Discussion Determination of Neurocompatibility and Neuronal Cell Proliferation The MTT proliferation studies indicated that the PANi neurosponge, PANi-E neurosponge, the PANi-C neurosponge and the xpi-PANi-E-C neurosponge were capable of efficiently supporting the growth of PC12 cells compared to the control over a period of 72 hours. This confirmed the neurocompatibility of the PANi neurosponge, the PANi-E neurosponge, the PANi-C neurosponge and the xpi-PANi-E-C neurosponge (labelled as PANi-EC) as displayed in FIG. 18. The xpi-PANi-E-C neurosponge (labelled as PANi-EC) displayed better neuronal proliferation as compared to the PANi neurosponge, the PANi-E neurosponge, and the PANi-C neurosponge. Without being limited to theory, this may be attributed to the close resemblance of the xpi-PANi-E-C neurosponge with the spinal cord architecture and extra cellular matrix (ECM) morphology.

Functional and Behavioural Outcome after the Xpi-PANi-E-C Neurosponge Implantation Post-SCI A lesion-control group was also observed to obtain functional recovery data post-SCI with no intervention. Only drug-free scaffolds were tested in vivo for the proof-of-concept. In addition to the assessment of functional locomotor outcome, the recovery of bladder function in the SCI rats post-implantation. The BBB functional locomotor outcome analysis was performed on the animals showing highest motor functioning and bladder function recovery (FIG. 19).

Control Group with Spinal Cord Injury (Group 0)

This group was the most challenging group in terms of post-operative care as the bladder function recovered in these animals only after 2 weeks and in one case no bladder recovery was observed throughout the study period. In latter case, the animal also showed signs of autophagy and severe (inconsistent) discomfort. Bladder infection was also observed in 2 cases. A maximum BBB score of 7 was achieved on day 28 post-injury and the study was terminated after this. Although some sensation in the hind limbs was observed after day 7; no sensation was observed in the tail throughout the study period. The injured site on day 28 showed substantial scar formation and the extracted tissue appeared to be very stiff. FIG. 20 A-H shows a sequential presentation of the extent of functional recovery over a 28-day duration post-SCI in the control group (Group 0).

Xpi-PANi-E-C Neurosponge (Group II)

xpi-PANi-E-C neurosponge provided the significant motor functional results post-SCI/post-implantation. Significant motor functions were recovered as early as 4 days with bladder function recovery observed within 72 hours. By day 7, the animals were able to hold the full body weight on the hind limbs and conformably stretched their bodies against the cage edge. No autophagy was observed among the animals in this group. The maximum BBB score obtained for the animals was 19 with slight trunk instability due to the tail not being consistently up. The injured site post-28 days displayed complete rejoining of the spinal cord stumps with "resilience resembling" the native spinal cord tissue. No scar formation was observed over the transected tissue. FIG. 21 shows sequential presentation (A) to (I) of the extent of functional recovery over a 28-day duration post-SCI in the xpi-PANi-E-C group.

Histological, Immunohistochemistry and Immunofluorescence Analysis

The H&E-stained sections displayed a spectrum of lesions. These ranged from minimally-disrupted nerve fibre tracts, predominantly within white matter, through progressive stages of nerve/axon degeneration/loss, to total nerve transection. Finally, a number of specimens were characterised by attempted/abortive reparative and regenerative changes, with total transverse replacement of the cord by a localised mass of multinucleate cells and liberated extracellular matrix ("reparative phenotype"). Examples of sample numbers include the baseline group (NAD; FIG. 22, xpi-PANi-E-C-B (Grade 2; FIG. 23), control group (Grade 4; FIG. 24) and xpi-PANi-E-C-A (Grade 5; FIGS. 25-26).

The ED1-stained sections also displayed a range of changes. Examples of all grades of lesion were present throughout the specimen group. In addition to the expression of ED1 amongst the glial/histiocytic/gitter cell population, scattered endothelial cells also displayed variably-positive staining, as did the multinucleate aggregates of presumptive regenerating neuroblasts. H&E-stained lesion grades were correlated to increased levels of ED1-positive cellular infiltrates. Examples of samples included baseline specimen (Grade 0; FIG. 27), xpi-PANi-E-C-B (Grade 2; FIG. 28), and xpi-PANi-E-C-A (Grade 4; FIG. 29).

The iNOS-stained sections displayed diffuse intra- (neuronal, glial, histiocytic and neuroblastic) and extra-cellular production/liberation of the enzyme, throughout both the grey and white matter of the spinal cord. Staining intensity tended to correlate with the severity of lesion present and was predominantly uniform in distribution, with occasional foci of more intense staining within regions of spinal cord adjacent to a lesion. Examples of samples included baseline specimen (Grade 0; FIG. 30), and xpi-PANi-E-C-C (Grade 2; FIG. 31).

The Calpain-stained sections were variable. There was some minimally-increased (Grade 1) staining within both intra-lesional areas and white matter tracts of affected specimens. Intra-lesional staining was noted intra-cellularly within (presumptive) regenerative neuroblasts (xpi-PANi-E-C-A, FIG. 32), and also within white matter tracts, in a small number of specimens (Control, FIG. 33). Given the inconsistent and sporadic observation of staining, the significance of this finding was uncertain.

The GFAP-stained fluorescent sections displayed a spectrum of changes, which correlated with the structural findings as noted within the H&E-stained sections. There was a strong correlation between H&E-stained lesion severity and the gradual loss of structural reticular architecture with this protein. Reparative phenotypic changes revealed a complete loss of fibre alignment, with replacement by a homogeneous and diffuse deposition of GFAP-positive material, of light intensity. NF-200-stained sections were likewise correlated with the findings as noted within H&E-stained sections, with a gradual loss of tubular structure as the lesion progressed in terms of severity. Reparative lesions displayed a total loss of protein at the site of the transaction, marginal areas within these samples displaying a branching of GFAP-positive protein (early repair ("scarring")). Examples included baseline specimen (Grade 0; FIG. 34), and xpi-PANi-E-C-A (Grade 4; FIGS. 35 and 36).

TABLE 6

Sample numbers and associated severity grades (please see above for textual context).

| Sample Number: | H & E: | ED1: | iNOS: | Calpain: | GFAP: | NF-200: |
| --- | --- | --- | --- | --- | --- | --- |
| Baseline-L1 | NAD | 0 | 0 | 0 | 0 | 0 |
| Baseline-L2 | NAD | 0 | 0 | 0 | 0 | 0 |
| Baseline-L3 | NAD | 0 | 0 | 0 | 0 | 0 |
| Control-L1 | 3 | 2 | 1 | 1 | 2 | 2 |
| Control-L2 | 3 | 2 | 1 | 1 | 3 | 3 |
| Control-L3 | 4 | 2 | 1 | 1 | 3 | 3 |
| xpi-PANi-E-C I-A | 5 | 4 | 2 | 1 | 4 | 4 |
| xpi-PANi-E-C-A- | 5 | 4 | 2 | 1 | 4 | 4 |
| xpi-PANi-E-C-A- | 5 | 3 | 2 | 1 | 4 | 4 |
| xpi-PANi-E-C-B- | 2 | 2 | 1 | 0 | 2 | 2 |
| xpi-PANi-E-C-B- | 2 | 2 | 2 | 0 | 1 | 2 |
| xpi-PANi-E-C-B- | 2 | 1 | 1 | 0 | 2 | 1 |
| xpi-PANi-E-C-C- | 5 | 4 | 2 | 0 | 4 | 4 |
| xpi-PANi-E-C-C- | 5 | 4 | 2 | 1 | 4 | 4 |
| xpi-PANi-E-C-C- | 5 | 4 | 2 | 0 | 4 | 4 |

FIG. 22 shows a hematoxylin & eosin (H&E) specimen baseline; L2. 5× Objective: NAD, highlighting the morphologically unremarkable spinal cord specimen.

FIG. 23 shows an H&E specimen—xpi-PANi-E-C-B; L2. 30× Objective: Grade 2, highlighting numerous degenerate nerve fibres (arrows).

FIG. 24 shows an H&E specimen—control; L3. 8× Objective: Grade 4. Note the total transverse transection of nerve, with numerous degenerate nerve fibres, area of total architectural disruption/loss (stars) and replacement by vacuolated gitter cells (arrows).

FIG. 25 shows an H&E specimen xpi-PANi-E-C-A; L3. 3× Objective: Grade 5. Note the total transverse transection of nerve and replacement by a mass of (presumptive) regenerating neuroblasts (thick arrow).

FIG. 26 shows an H&E specimen xpi-PANi-E-C-A; L3. 16× Objective: Grade 5. Note the total transverse transection of nerve, with numerous degenerate nerve fibres, area of total architectural disruption/loss (stars), and replacement by eosinophilic extracellular matrix (arrows) and multinucleate (presumptive) regenerate neuroblasts (large arrows).

FIG. 27 shows an ED1 specimen Baseline; L2. 40× Objective: Grade 0. Note the low number of scattered positive glial cells (arrow).

FIG. 28 shows an ED1 specimen xpi-PANi-E-C-B; L1. 40× Objective: Grade 2. Note the positive glial cells (arrows) and endothelial cell (thick arrow).

FIG. 29 shows an ED1 specimen xpi-PANi-E-C-A; L1. 40× Objective: Grade 4. Note the myriad and often degenerate/degenerating positive glial cells (arrows), in addition to the presence of positive multinucleate cells (star), indicating the presence of histiocytic marker expression within multinucleate gitter cells and/or primitive neuroblasts.

FIG. 30 shows an inducible nitric oxide synthase (iNOS) specimen Baseline; L2. 5× Objective: Grade 0. Note the baseline level of staining throughout intra- and extra-cellular components of the white (arrow) and grey (star) matter.

FIG. 31 shows an iNOS specimen xpi-PANi-E-C-C; L2. 5× Objective: Grade 2. Note the increased intensity of staining within intact and extra-lesional white matter (arrow).

FIG. 32 shows a calcium-activated nonlysosomal neutral proteases (calpain) specimen xpi-PANi-E-C-A; L1. 10× Objective: Grade 1. Note the minimal presence of intra-cellular staining (red) within multinucleate giant cells (arrows).

FIG. 33 shows a calpain specimen Control; L. 15× Objective: Grade 1. Note the minimal presence of intra-/extra cellular staining (red) within damaged cord (arrows).

FIG. 34 shows a glial fibrillary acidic protein/neurofilament-200 (GFAP/NF-200) specimen Baseline; 60× Objective: Grade 0. Note the diffuse and fine reticular GFAP-positive structural network (red) and variably-sized, linear, NF-200-positive tubular network (green). Note—nuclei stain blue.

FIG. 35 shows a GFAP/NF-200 specimen xpi-PANi-E-C-A; L1. 60× Objective: Grade 4. Note the total loss of the fine reticular GFAP-positive structural network with replacement by a diffuse and homogeneous GFAP-positive protein deposit (stars). Residual and scant NF-200-positive material is represented by condensed globular deposits (arrow).

FIG. 36 shows a GFAP/NF-200 specimen xpi-PANi-E-C-A; L1. 60× Objective: Grade 4; marginal zone. Note the marginal rounding and thickening of GFAP-positive protein at the margin of the reparative lesion (arrow).

Concluding Remarks

Control and treated specimens displayed a range of changes. These were best demonstrated via H&E-staining, which characterised the lesion into progressively transected/degenerative presentations, and reparative phenotypes. ED1-stained specimens demonstrated a progressive influx of cells of histiocytic/microglial lineage into the lesions, increasing in number as the severity progressed. The injuries were accompanied by a progressive upregulation of iNOS expression, with increases in the expression/release of Calpain. GFAP and NF-200 structural integrity was progressively lost as the severity of the lesion progressed. Reparative changes were accompanied by marked upregulation of iNOS, a notable influx of ED1-positive chronic inflammatory cells, the appearance of multinucleate cells characteristic of presumptive regenerative neuroblasts and near-complete loss of GFAP and NF-200 protein/structural integrity.

REFERENCES

Ray M, Pal K, Anis A, Banthia A K 2010. Development and characterization of chitosan-based polymeric hydrogel membranes. Des Monomers Polym 13:193-206.

Yang L, Zhang L, Webster T J 2011. Nanobiomaterials: state of the art and future trends. Adv Eng Mater 13(6):B197-217.

Zhang S 2003. Fabrication of novel biomaterials through molecular self-assembly. Nat Biotechnol 21(10):1171-8.

The invention claimed is:

1. A method of treating a spinal cord injury comprising implantation of a pharmaceutical composition into a human or animal body at, near, adjacent to, or in connection with, a spinal cord of said human or animal body,
wherein the pharmaceutical composition comprises polyacrylonitrile (PANi), elastin (E), and collagen (C) together forming a polyacrylonitrile (PANi), elastin (E), collagen (C) polymer network (PANi-E-C), wherein the polyacrylonitrile (PANi) is crosslinked via a crosslinking agent to form a crosslinked, porous, semi-interpenetrating or interpenetrating polyacrylonitrile (PANi), elastin (E) and collagen (C) polymer network (xpi-PANi-E-C), wherein the crosslinked polyacrylonitrile (PANi) associates and/or bonds and/or connects with the elastin (E) and collagen (C) facilitating reorientation of secondary structure of proteins elastin (E) and collagen (C);
wherein the reorientation of the secondary structure of proteins elastin (E) and collagen (C) within xpi-PANi-E-C results in the concentration dependent secondary structure of proteins elastin (E) and collagen (C) being such that the concentration of random coils>a-helix>b-sheets>b-turns;
and wherein reorientation of both elastin (E) and collagen (C) provides for the reorientated secondary structure of proteins elastin (E) and collagen (C) to approximate, or to be in, their native or natural form as naturally found in the extra cellular matrix (ECM) of a human or animal such that the pharmaceutical composition mimics human or animal spinal cord tissue.

2. The method of claim 1, wherein the xpi-PANi-E-C further comprises a network of channels and/or tunnels imparting sponge-like characteristics thereto and wherein the channels and/or tunnels include along their inner surfaces protrusions, such that in use, when the pharmaceutical composition is implanted into a human or animal body at, near, adjacent to, or in connection with, a spinal cord of said human or animal body, the channels and/or tunnels provide a pathway for nerve tissue and/or axonal growth and/or repair, and the protrusions provide an anchoring means for nerve tissue or neuronal tissue facilitating growth and/or repair.

3. The method of claim 1, wherein the crosslinking agent is methylenebisacrylamide (MBAAm).

4. The method of claim 1, wherein the pharmaceutical composition is produced by the following steps:
   (i) dissolving elastin (E) and collagen (C) in an acidic aqueous medium to form a first solution;
   (ii) adding acrylonitrile to the first solution and mixing to form a second solution, which second solution is agitated/mixed until homogenous;
   (iii) adding an initiator to the homogenous second solution, wherein the initiator initiates free radical polymerization of the acrylonitrile to form an interpenetrating polyacrylonitrile (PANi), elastin (E) and collagen (C) polymer network (iPANi-E-C); and
   (iv) adding a crosslinking agent,
wherein the crosslinking agent crosslinks the polyacrylonitrile (PANi) to form a crosslinked, porous, interpenetrating polyacrylonitrile (PANi), elastin (E) and collagen (C) polymer network (xpi-PANi-E-C), and wherein the method facilitates and provides for the reorientated secondary structure of the elastin (E) and collagen (C) proteins.

\* \* \* \* \*